US010835312B2

(12) United States Patent
Vetter

(10) Patent No.: US 10,835,312 B2
(45) Date of Patent: Nov. 17, 2020

(54) METHODS, DEVICES AND THERAPEUTIC PLATFORM FOR AUTOMATED, SELECTABLE, SOFT TISSUE RESECTION

(71) Applicant: TRANSMED7, LLC, Portola Valley, CA (US)

(72) Inventor: James W Vetter, Portola Valley, CA (US)

(73) Assignee: Transmed7, LLC, Portola Valley, CA (US)

(*) Notice: Subject to any disclaimer, the term of this patent is extended or adjusted under 35 U.S.C. 154(b) by 1298 days.

(21) Appl. No.: 14/615,750

(22) Filed: Feb. 6, 2015

(65) Prior Publication Data

US 2015/0201994 A1    Jul. 23, 2015

Related U.S. Application Data

(63) Continuation of application No. 14/253,793, filed on Apr. 15, 2014, now abandoned.

(Continued)

(51) Int. Cl.
*A61B 18/14* (2006.01)
*A61B 10/02* (2006.01)
(Continued)

(52) U.S. Cl.
CPC .......... *A61B 18/148* (2013.01); *A61B 8/0841* (2013.01); *A61B 10/0266* (2013.01);
(Continued)

(58) Field of Classification Search
CPC .......... A61B 17/320758; A61B 2017/320004; A61B 2017/320766; Y10T 29/49863
See application file for complete search history.

(56) References Cited

U.S. PATENT DOCUMENTS

| 1,813,902 A | 7/1931 | Bovie |
| 2,816,552 A | 12/1957 | Hoffman |

(Continued)

FOREIGN PATENT DOCUMENTS

| DE | 19528440 A1 | 2/1997 |
| WO | 9502370 | 1/1995 |

(Continued)

OTHER PUBLICATIONS

International Search Report dated Jan. 22, 2015 in related PCT application PCT/US14/34252.

(Continued)

*Primary Examiner* — Elmer M Chao
(74) *Attorney, Agent, or Firm* — Young Law Firm, P.C.

(57) ABSTRACT

An excisional device may comprise an introducer comprising a distal trough portion and a cutting assembly. The cutting assembly may comprise an axial hand element configured to selectively bow out of and away from the distal trough portion and to retract into the distal trough portion and a helical cutting element wound around the axial band element. A rotating drum may be provided to cause the cutting assembly to selectively rotate, bow and retract according to a mechanically-driven first cutting profile that is defined by a shape of a channel formed in the drum. An optical guidance projector assembly may be coupled to the excisional device and may be configured to visually indicate when a distal portion of the excisional device is aligned with an imaging plane of an imaging probe and in a desired position.

32 Claims, 33 Drawing Sheets

Related U.S. Application Data

(60) Provisional application No. 61/812,637, filed on Apr. 16, 2013.

(51) Int. Cl.
*A61B 10/04* (2006.01)
*A61B 8/08* (2006.01)
*A61B 34/20* (2016.01)
*A61B 18/00* (2006.01)
*A61B 90/00* (2016.01)

(52) U.S. Cl.
CPC ............ *A61B 10/04* (2013.01); *A61B 18/149* (2013.01); *A61B 34/20* (2016.02); *A61B 2010/045* (2013.01); *A61B 2018/00202* (2013.01); *A61B 2018/00208* (2013.01); *A61B 2018/00333* (2013.01); *A61B 2018/00601* (2013.01); *A61B 2018/00982* (2013.01); *A61B 2018/141* (2013.01); *A61B 2018/144* (2013.01); *A61B 2018/1407* (2013.01); *A61B 2018/1435* (2013.01); *A61B 2018/1465* (2013.01); *A61B 2018/1475* (2013.01); *A61B 2034/2055* (2016.02); *A61B 2034/2063* (2016.02); *A61B 2034/2068* (2016.02); *A61B 2090/378* (2016.02); *A61B 2218/002* (2013.01); *A61B 2218/007* (2013.01)

(56) References Cited

U.S. PATENT DOCUMENTS

| | | |
|---|---|---|
| 3,320,957 A | 5/1967 | Sokolik |
| 3,732,858 A | 5/1973 | Banko |
| 3,749,085 A | 7/1973 | Willsan |
| 3,910,279 A | 10/1975 | Okada et al. |
| 3,955,578 A | 5/1976 | Chamness et al. |
| 4,099,518 A | 7/1978 | Baylis et al. |
| 4,245,653 A | 1/1981 | Weaver |
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |
| 4,903,696 A | 2/1990 | Stasz et al. |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,174,296 A | 12/1992 | Watanabe et al. |
| 5,176,688 A | 1/1993 | Narayan |
| 5,192,291 A | 3/1993 | Pannek |
| 5,211,651 A | 5/1993 | Reger |
| 5,217,479 A | 5/1993 | Shuler |
| 5,224,488 A | 7/1993 | Neuffer |
| 5,224,945 A | 7/1993 | Pannek et al. |
| 5,282,484 A | 2/1994 | Reger |
| 5,292,310 A | 3/1994 | Yoon |
| 5,308,321 A | 5/1994 | Castro |
| 5,318,576 A | 6/1994 | Plassche |
| 5,325,860 A | 7/1994 | Seward et al. |
| 5,415,656 A | 5/1995 | Tihon et al. |
| 5,441,510 A | 8/1995 | Simpson et al. |
| 5,527,326 A | 6/1996 | Hermann |
| 5,554,163 A | 9/1996 | Shturman |
| 5,630,426 A | 5/1997 | Eggers et al. |
| 5,632,754 A | 5/1997 | Farley et al. |
| 5,672,172 A | 9/1997 | Zupkas |
| 5,709,697 A | 1/1998 | Ratcliff |
| 5,766,191 A | 6/1998 | Trerotola |
| 5,794,626 A | 8/1998 | Kieturakis |
| 5,827,305 A | 10/1998 | Gordon |
| 5,895,399 A | 4/1999 | Barbut et al. |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Seiver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,139,508 A | 10/2000 | Simpson |
| 6,179,860 B1 | 1/2001 | Fulton, III et al. |
| 6,221,006 B1 | 4/2001 | Dubrul et al. |
| 6,238,389 B1 | 5/2001 | Paddock et al. |
| 6,280,450 B1 | 8/2001 | McGuckin, Jr. |
| 6,331,166 B1 | 12/2001 | Burbank et al. |
| 6,387,056 B1 | 5/2002 | Kieturakis |
| 6,423,081 B1 | 7/2002 | Lee et al. |
| 6,440,147 B1 | 8/2002 | Lee et al. |
| 6,514,248 B1 | 2/2003 | Eggers et al. |
| 6,602,204 B2 | 8/2003 | Dubrul et al. |
| 6,605,047 B2 | 8/2003 | Zarins et al. |
| 6,626,903 B2 | 9/2003 | McGuckin et al. |
| 6,689,145 B2 | 2/2004 | Lee et al. |
| 6,702,831 B2 | 3/2004 | Lee et al. |
| 6,764,495 B2 | 7/2004 | Lee et al. |
| 6,849,080 B2 | 2/2005 | Lee et al. |
| 6,863,676 B2 | 3/2005 | Lee et al. |
| 2002/0058885 A1 | 5/2002 | Burbank et al. |
| 2002/0099398 A1 | 7/2002 | Lee et al. |
| 2004/0087872 A1 | 5/2004 | Anderson et al. |
| 2007/0198010 A1 | 8/2007 | Lee et al. |
| 2008/0249552 A1 | 10/2008 | Eliachar et al. |
| 2010/0121361 A1* | 5/2010 | Plowe ............ A61B 17/320758 606/159 |
| 2011/0313529 A1* | 12/2011 | Schaller ........... A61B 17/32002 623/17.16 |
| 2013/0190651 A1 | 7/2013 | Vetter |

FOREIGN PATENT DOCUMENTS

| | | |
|---|---|---|
| WO | 9502371 | 1/1995 |
| WO | 0010471 | 3/2000 |
| WO | 0012009 | 3/2000 |
| WO | 0016697 | 3/2000 |
| WO | 0030531 | 6/2000 |
| WO | 0033743 | 6/2000 |
| WO | 0044295 | 8/2000 |

OTHER PUBLICATIONS

Written Opinion of the International Searching Authority dated Jan. 22, 2015 in elated PCT application PCT/US14/34252.
EPO Extended Search Report dated Jun. 8, 2017 in EPO Appln 14837735.1.

* cited by examiner

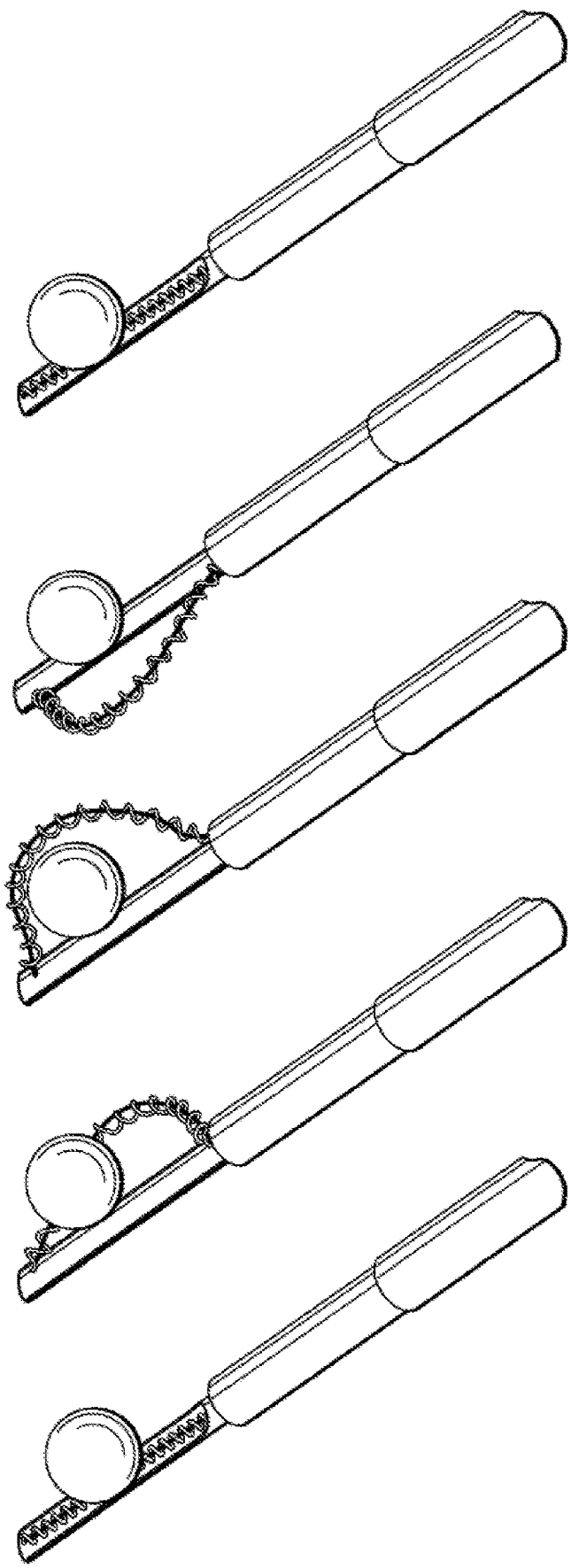

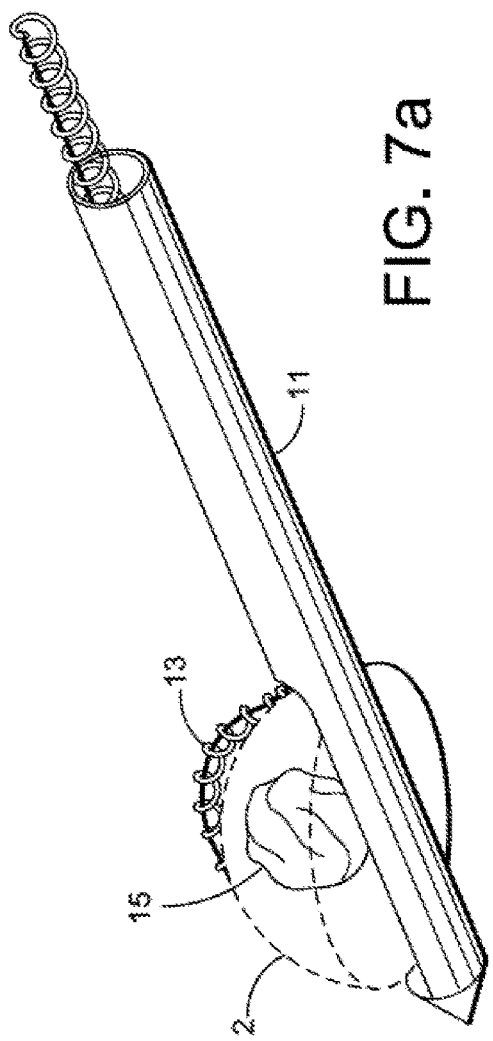
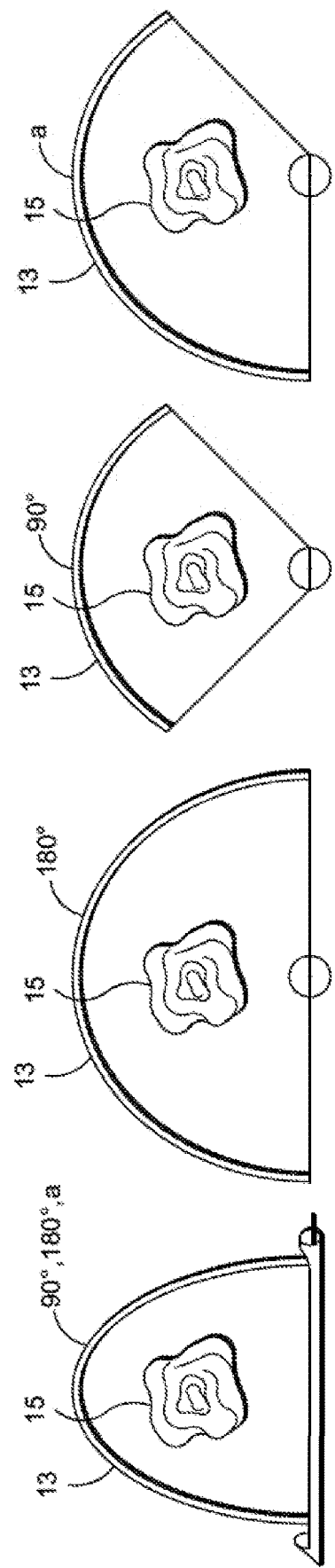

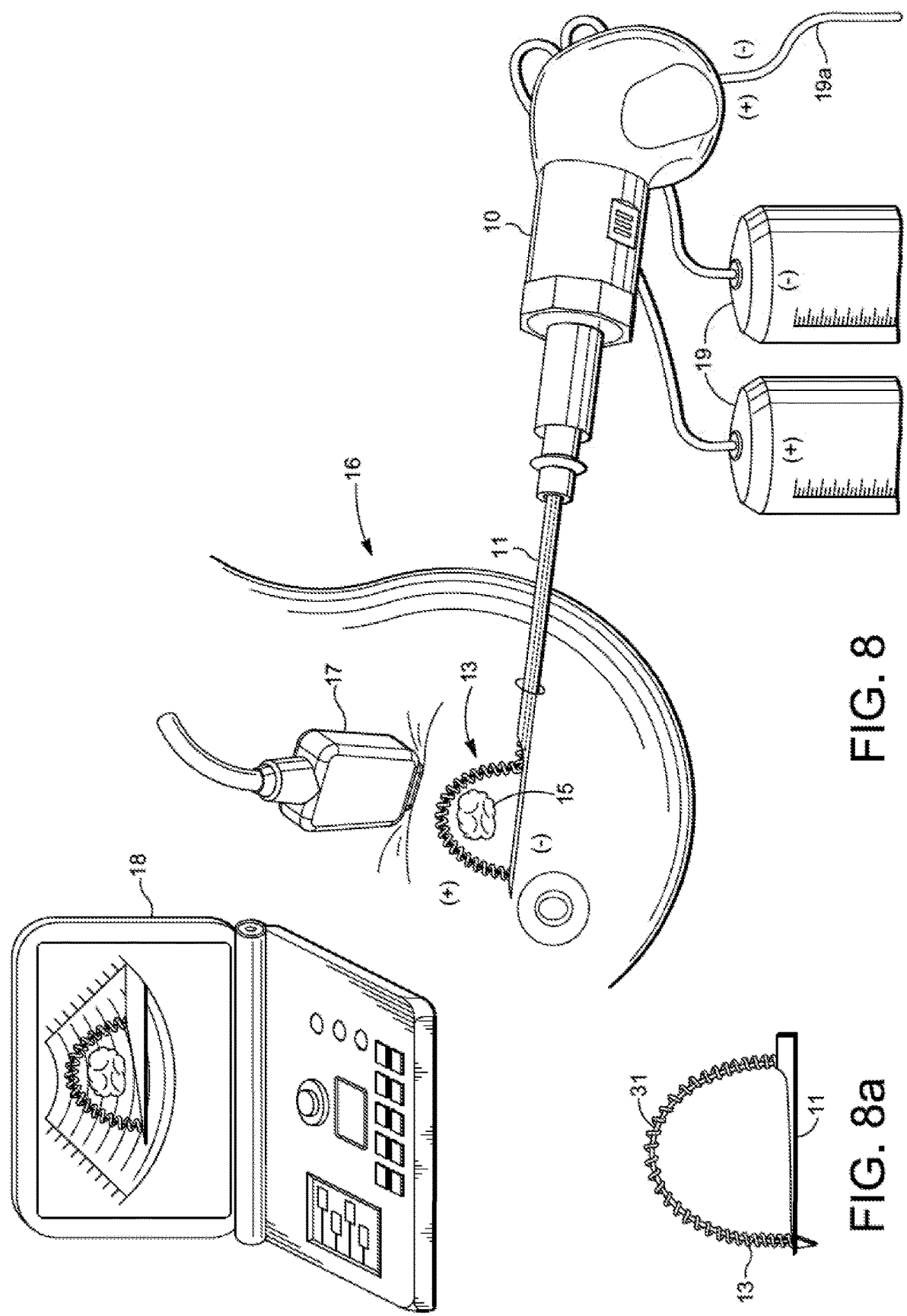

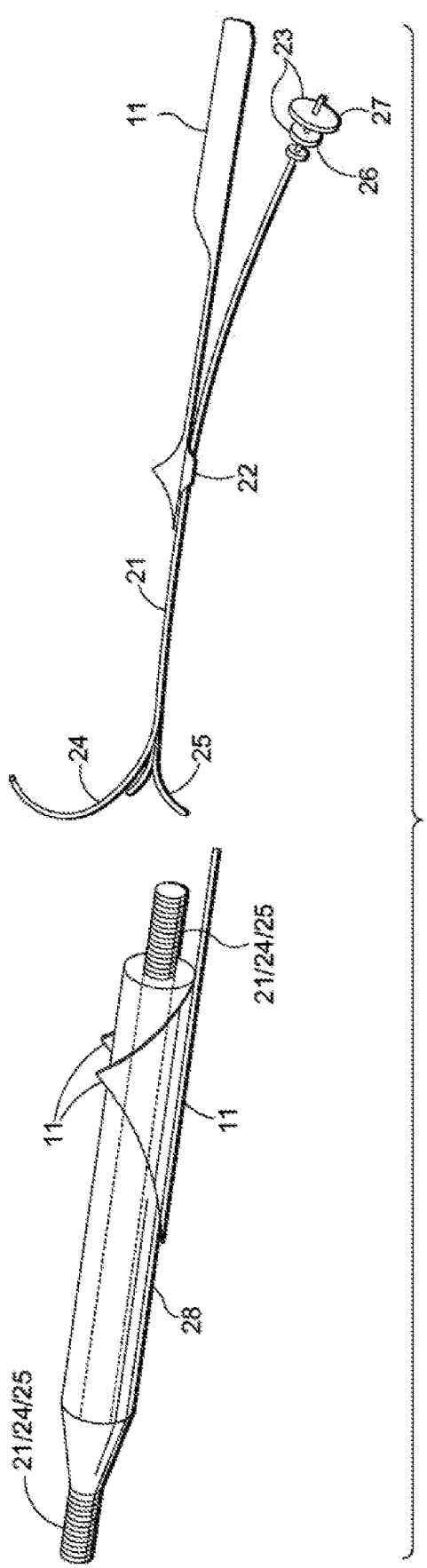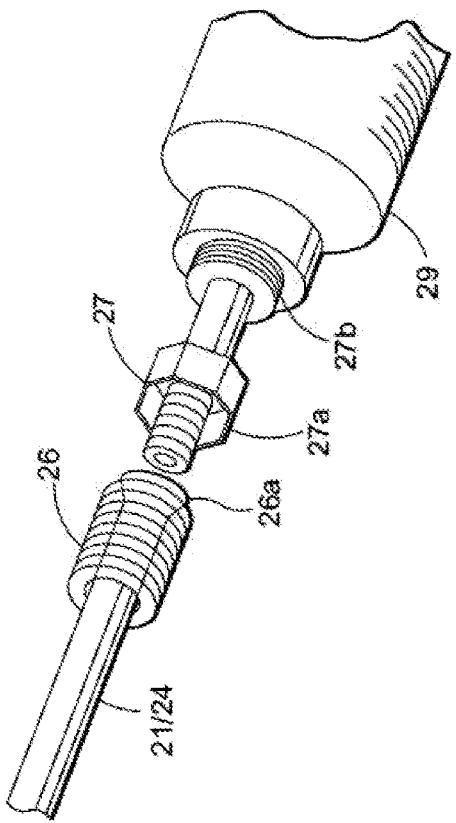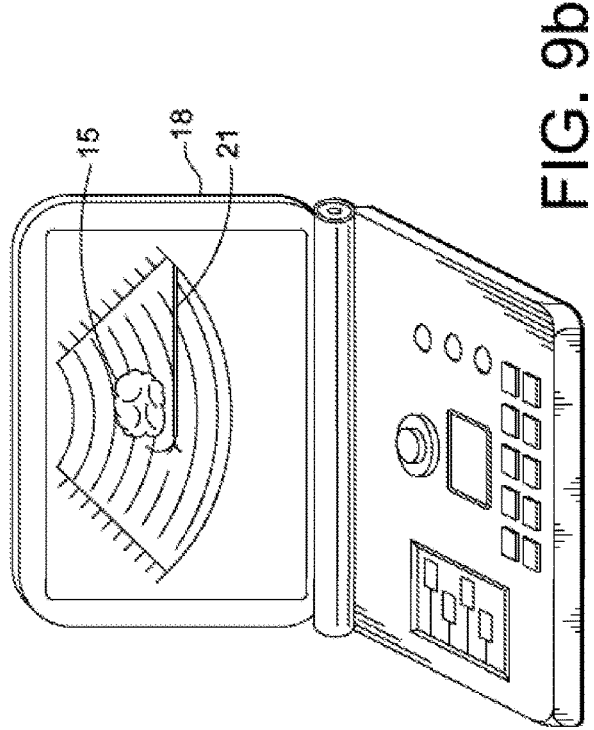
FIG. 9a
FIG. 9b
FIG. 9c

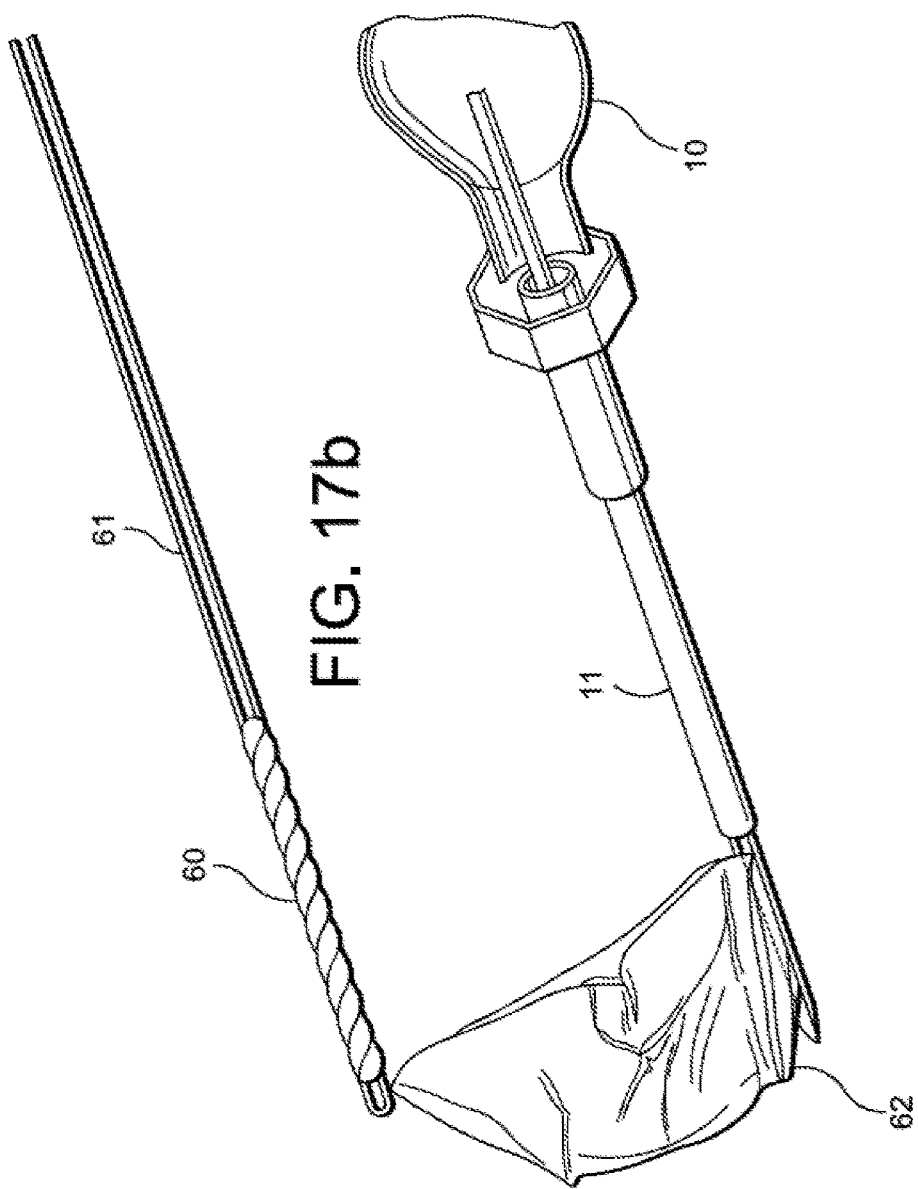
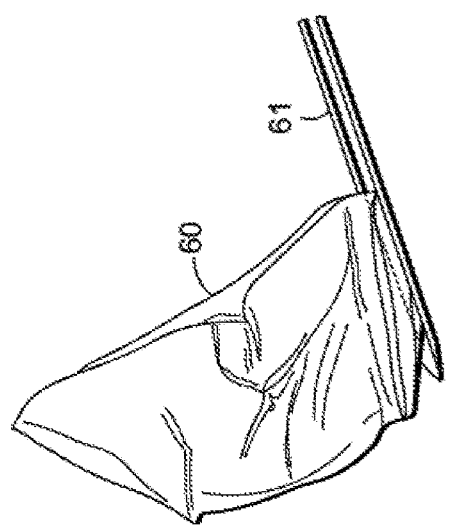

METHODS, DEVICES AND THERAPEUTIC PLATFORM FOR AUTOMATED, SELECTABLE, SOFT TISSUE RESECTION

BACKGROUND

The present disclosure is in the technical field of medical devices. More particularly, the embodiments described and shown therein are in the technical field of minimally invasive, surgical resection and therapy devices.

BRIEF DESCRIPTION OF THE DRAWINGS

FIGS. 6a, 6b, 6c, 6d and 6e show various views of an excisional device distal end in relation to a lesion.

FIG. 7a shows further details of a pattern of excision made by an excisional loop component of an excisional device of FIG. 2, according to one embodiment.

FIG. 7b shows further details of a pattern of excision made by an excisional loop component of an excisional device of FIG. 2, according to one embodiment.

FIG. 7c shows further details of a pattern of excision made by an excisional loop component of an excisional device of FIG. 2, according to one embodiment.

FIG. 7d shows further details of a pattern of excision made by an excisional loop component of an excisional device of FIG. 2, according to one embodiment.

FIG. 7e shows further details of a pattern of excision made by an excisional loop component of an excisional device of FIG. 2, according to one embodiment.

FIG. 8 shows an excisional device of FIG. 2 in position within a breast, according to one embodiment.

FIG. 8a shows an example of a possible actual size loop-cutting element, with part of a helical component shown over a band element of an excisional device or device assembly of FIG. 2, according to one embodiment.

FIG. 9a shows two other means of introducing introducer assembly 11 over guide assembly 21, including insert cannula 28 at the left, and at the right, eyelet element excisional device 22 of a universal introducer tray element 11 of an excisional device 10, according to one embodiment.

FIG. 9b shows details of a monitoring device for use with an excisional device, according to one embodiment.

FIG. 9c shows details of a hub connector assembly with its individual components 26, 26a, 27, 27a and 27b, according to one embodiment.

FIGS. 17, 17a and 17b are a series of furled and unfurled collection elements of a collection net, bag or other similar enclosure, alone and as shown in FIG. 17a, introduced within a universal introducer tray of an excisional device of FIG. 2, according to one embodiment.

DETAILED DESCRIPTION

Figure 1:
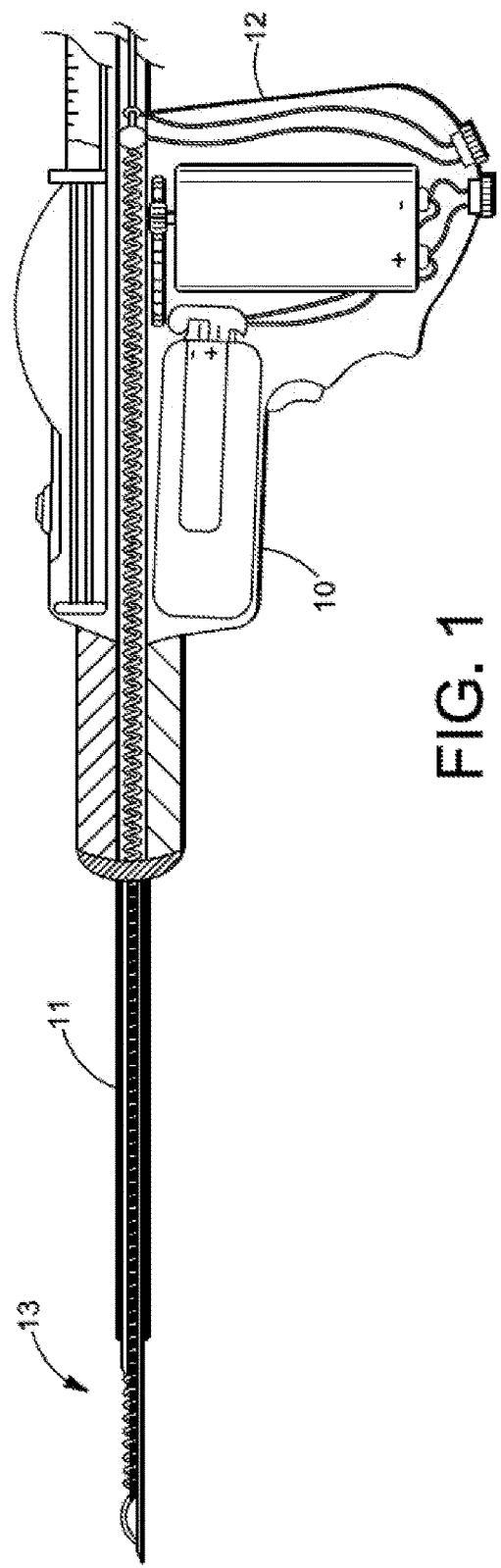
FIG. 1 is a side view of an excisional biopsy platform device assembly, according to one embodiment.

Conventional solutions for excisional resection of abnormal tissues from surrounding normal tissues fall into two main categories: those that involve direct visualization and manually guided instruments used in open surgical excisional resection and those that fall into the broad category of minimally invasive solutions. Minimally invasive solutions are typically guided by imaging modalities such as x-ray guidance, stereotactic imaging, computed tomographic scanning, magnetic resonance imaging and a variety of functional scans. Lack of adoptability has been the major hindrance to even the best of the minimally invasive devices, even when the results obtained appeared quite favorable in relation to the classic open surgical biopsy approach. In the case of direct, open surgical resection or open surgical biopsy, (when specifically referring to open surgical biopsy of breast cancers, called "lumpectomy") involving a simple sharp scalpel and/or a radiofrequency energized scalpel (so called "Bovie" tip, blade or loop), the results vary based on surgical skills. These variations lead to varying levels of effectiveness in removing all the abnormal tissues without removing too much normal surrounding tissue. Breast surgery is an area in great need of improvement and one that illustrates several shortcomings of a traditional surgical approach.

Recent studies have shown a highly unsatisfactory rate of re-operation to remove residual abnormal tissue, such as cancerous tissue, left behind by the initial surgical treatment. These rates of re-excision range from 30% to nearly 50% depending on several factors. In an attempt to limit re-operations and more effectively remove all traces of abnormal tissues during the initial therapeutic surgical procedure, guidance modalities such as ultrasound have been introduced in an effort to more clearly identify the margins between normal and abnormal tissues. In so doing, success rates jumped up from 60% to as high as 90% in terms of excising all traces of cancer during the first surgical procedure. Problems, however, remain. First, scalpels/Bovie tips are difficult to see as they move in and out of the imaging plane, which makes it difficult to perform the procedures with precision. Thus, though many lesions are relatively easy to visualize, sighting the instrument used, consistently and reliably, within the imaged field in order to accurately and completely excise the abnormality, is not. As a result, a larger amount of tissue than would otherwise be necessary is often excised, not only due to the lack of easy visualization of the excising instrument, but also partly because the correct, curving line around the abnormal tissues is difficult to make with a short straight blade. Moreover, the surgeon often has too great a freedom of movement to permit stable visualization and/or control of the cutting instrument.

Another issue lies in the assessment of a clear "margin" as determined by the pathology lab. Because the cut surface is inconsistently made when carried out freehand in an open surgical procedure, overly large and raggedly shaped specimens are presented to the lab, making preparation for examination difficult. The result is that "margins" of such specimens are actually not clear, despite the paramount importance of achieving clean margins. Though there are some tests that can help with the assessment, the fact remains that along with direct measurement of the size of the abnormality in the case of cancer, the assessment of clear margins is the pivotal, fundamental piece of information upon which all subsequent predictions for prognosis and treatment strategies are predicated.

One other important factor in the determination of the level of aggressiveness and hence danger to the patient of a particular abnormality is the perceivable behavior of cells on the border, in nearby zones of influence of potentially dangerous abnormal tissue such as invasive cancers. The ability to provide a relatively uniform border zone for easier, comparative evaluation of these cells in these areas thus provides important clues as to the level of harmful activities in-vivo of the potentially dangerous tissues as demonstrated by their effects on and the changes in these border cells.

Although conventional direct surgical excision has significant limitations from the standpoint of information, it still is considered the best, first step in the therapy of potentially life threatening abnormalities as invasive cancers as compared to other techniques such as ablations, and/or some of the other minimally invasive approaches. Such minimally invasive approaches may be based on incomplete removal followed by intense irradiation or other maneuvers meant to compensate for less than complete removal. Such techniques, however, are also far superior to any techniques based on removal of abnormal tissues in a piecemeal fashion. For instance, measurement of overall sample size is far more difficult when trying to recreate geometries from individual cores or pieces. Also, assessment of clear margins is all but impossible from individual pieces of tissue. Furthermore, attempts to assess whether any abnormal tissues have been left behind are immeasurably more difficult when the target tissue has been removed in a piecemeal fashion. Indeed, such techniques leave difficult to image, small, non-contiguous fragments behind. Therefore, all other devices based on fragment removal are considered even less satisfactory and less effective than direct surgical excision, even with its significant limitations.

Paradoxically, open surgical excision, commonly referred to as "lumpectomy," was developed for the purpose of achieving a more favorable cosmetic result. In other words, the procedure was developed to duplicate the favorable survival results of radical mastectomy, modified radical mastectomy and quadrectomy, to lessen pain and disfigurement, immune suppression, and any need for subsequent procedures to achieve acceptable cosmetic and patient satisfaction results. In order to achieve these goals, clear margins (e.g., margins having at least one cell of thickness) must be obtained. The next requirement in prevention of recurrence and to duplicate the results of the far more radical approaches to control recurrence, is the accepted necessity to combine the lumpectomy with local brachytherapy or irradiation of border zone tissues.

The manner in which lumpectomies are performed leaves much to be desired. Again, since more normal tissue is removed than is necessary, the area of radiation is far wider than it would need to be had the abnormal area been more precisely traced around. Additionally, because little effective attention and techniques are directed towards creating a uniform margin centered on the central mass of the abnormal tissue, the distances from the abnormal tissue to the edges of the transitional zone are likewise not as consistently uniform from a dimensional perspective as they should be in order to optimize radiation dosages. Since radiation dose and its fall-off is highly dependent on distance from the radiation source (generally following an inverse square law), an irregularly-made lumpectomy with an off-center lesion necessarily necessitates a higher dose than needed to tissues that are or were nearer to the original abnormality in order to deliver an effective dose to all, particularly more distant, target tissues in the transition zone.

The modes of operation of existing thermal devices to kill cancers, piecemeal correlating devices, snare devices and a variety of surface excisional devices ignore the reality that the excised tissue is such an important source of information that ablating it or otherwise destroying it does a massive disservice to the patient from whom it is removed. The information contained within the excised specimen is precious, as evidenced by the entire field of pathology, which is dedicated to the accurate and timely analysis of the removed tissue specimen(s).

According to embodiments, a platform and devices are configured to enable pre-treatment, precise imaging and excision, and easy collection of excised lesions along with automatic preservation of critical information such as orientation. The platform also provides a structure to support post treatment procedures of a wide variety ranging from cosmetic enhancements to therapeutic adjuncts.

Embodiments comprise a family of various medical devices, collectively referred to herein as an excisional device, that, when used together, are configured to perform excisional procedures and, with certain components attached, are configured to perform these procedures in a minimally invasive manner (including percutaneously). The platform, according to one embodiment, is configured to enable performing diagnostic, therapeutic and various other types of treatment procedures. Such a platform instrument, according to one embodiment, may be configured, with its cutting accessory attached, to perform resection and then in conjunction with various additional attachments, retrieve whole, intact masses of abnormal appearing and/or normal appearing tissues through the smallest possible dermal incision, during a single procedure of multiple, easily achievable steps. Embodiments optimize the ability to achieve precise placement and stabilization of the platform device into the soft tissue area of the body from which the abnormal tissue is taken. Embodiments may be used in the various stages of excisional and related diagnostic and therapeutic adjunctive portions of an overall clinical objective or procedure. Indeed, embodiments may be configured for pre-treatment of the area and/or of the abnormal tissue, delivery of tracer materials for tracking the potential spread or flow patterns whereby the abnormal tissues (such as cancerous tissues) may metastasize, the intra-procedure delivery of medications that may anesthetize tissues at the site, delivery of other agents such as pro-coagulants and others, as well as post-procedure materials such as medications, implantable materials for cosmetic purposes and other implantable elements such as marking devices, the delivery of local brachytherapy, alone or in combination with enhancing medications, shielding devices and/or materials. For example, ultrasound devices (e.g., intra-tissue ultrasound probes) may be delivered to and manipulated within a selected procedure site with great precision.

Embodiments of the excisional device assembly along with associated related subcomponents described herein are configured to provide the ability to precisely resect and reliably retrieve solid, contiguous and/or fragmented tissues, substantially intact and oriented substantially as in vivo, to enable accurate laboratory assessment. Such assessment may include the identification of, for example, cancerous, fibrous, fibro-fatty, fatty and even semi-solid/semi-liquid tissues for analysis, diagnosis and for treatment. According to one embodiment, the excisional device platform and the other components described herein may be configured to be portable and may be configured to be disposable or reusable. Embodiments may be electrically and/or mechanically and/or manually powered and operated and may also be combined for purposes of effective cutting and/or coagulation, additionally or principally powered by sources such as radiofrequency generators, harmonic ultrasound or other energy types alone or in combination with one another. These devices may be guided by any number of guidance modalities including ultrasound, x-ray, magnetic resonance and/or functional modalities and may also be used with simple palpation either alone or in conjunction with the above-mentioned guidance means.

Though it is apparent that embodiments may be applied to multiple disease processes in many areas of the body, a clear understanding thereof may be obtained by a description of their uses as applied to the field of breast cancer diagnosis and treatment.

Figure 1A:
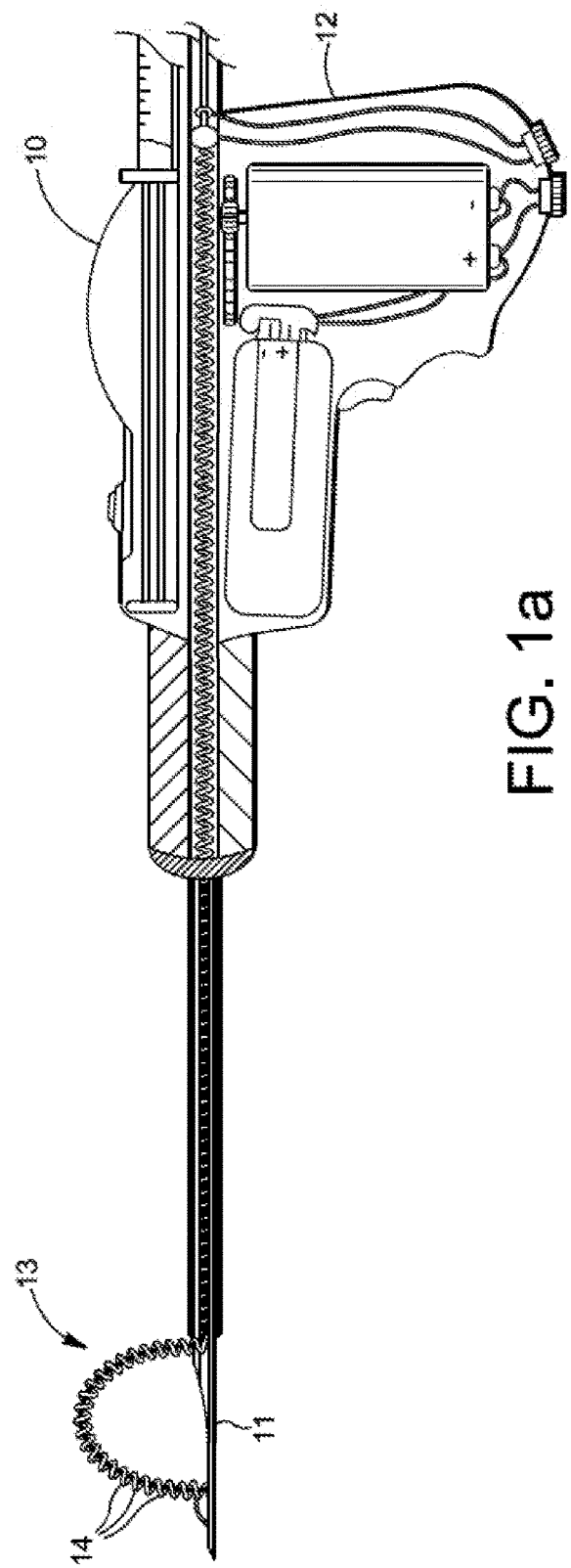
FIG. 1a is a side view of an excisional biopsy platform according to one embodiment.

FIG. 1 shows a cutting element in its pre-extended position within an excisional device assembly, and FIG. 1a shows the same element in an extended loop position within an excisional device assembly according to one embodiment. FIG. 1 and FIG. 1a show an excisional device assembly 10 comprising a cutting assembly 13, which is extendable into a loop shape, as shown in FIG. 1a. The cutting assembly 13 may also be at least partially retracted into a tubular introducer assembly 11. According to one embodiment, the tubular introducer assembly 11 may have a length of about 4 and ½ inches in length, to retrieve a single whole sample of tissue (not shown) sufficient to provide the desired clinical diagnostic or therapeutic result. Other dimensions are possible. The embodiment of excisional device 10 shown in FIGS. 1 and 1a is shown in a hand held configuration having an ergonomically comfortable and secure handle 12 at its proximal end, from which the tubular introducer assembly 11 protrudes so that the device 10 may be easily directed with one hand while the other hand is free to hold a guiding probe such as an ultrasound transducer (not shown). According to one embodiment, the device may be configured to fit onto any number of guiding devices such as a stereotactic imaging stage or other guidance modality, such as magnetic resonance imaging stages (not shown). As shown, the excisional device 10 may comprise a motor drive unit configured to rotate cutting assembly 13, as well as for projecting, in a forward distal direction, cutting element assembly 13 from within the tubular introducer assembly 11 for the purpose of bowing cutting assembly 13 outwards, in order to excise a targeted mass for removal, and also for complete parting off of the sample from surrounding tissues by revolving cutting assembly 13 along with and about the long axis of tubular introducer assembly 11. Tubular introducer assembly 11 (not all components thereof being visible in this illustration) may be configured, according to one embodiment, as a base from which cutting assembly 13 projects, and further, tubular introducer assembly 11, by being rotated about its long axis, acts to revolve coning assembly 13, once fully bowed outwards, around targeted lesion (not shown), and then back to its resting position within tubular introducer assembly 11. In this manner, the targeted lesion may be fully be excised from its surrounding normal tissue environment. After excision, the targeted lesion may be manually removed from the organ such as a breast, or, may be retrieved by adjunctive components discussed below.

According to one embodiment, excisional device 10 comprises a handle or proximal end 12, which comprises mechanical components to drive a distally disposed cutting assembly 13. As shown the assembly 13 may comprise helical cutting elements 14, configured to excise a target lesion or sample from its attachment within an organ such as a breast. The ability of the excisional device 10 to be introduced through a very small skin incision, be easily visualized, easily (extremely low profile, streamlined introducer component) and precisely placed directly below and far enough away from the inferior surface of a targeted lesion, such that inferior clear margins are assured improves upon the most difficult part of a standard excisional procedure; namely ensuring clear and uniform inferior border margins.

Figure 2:
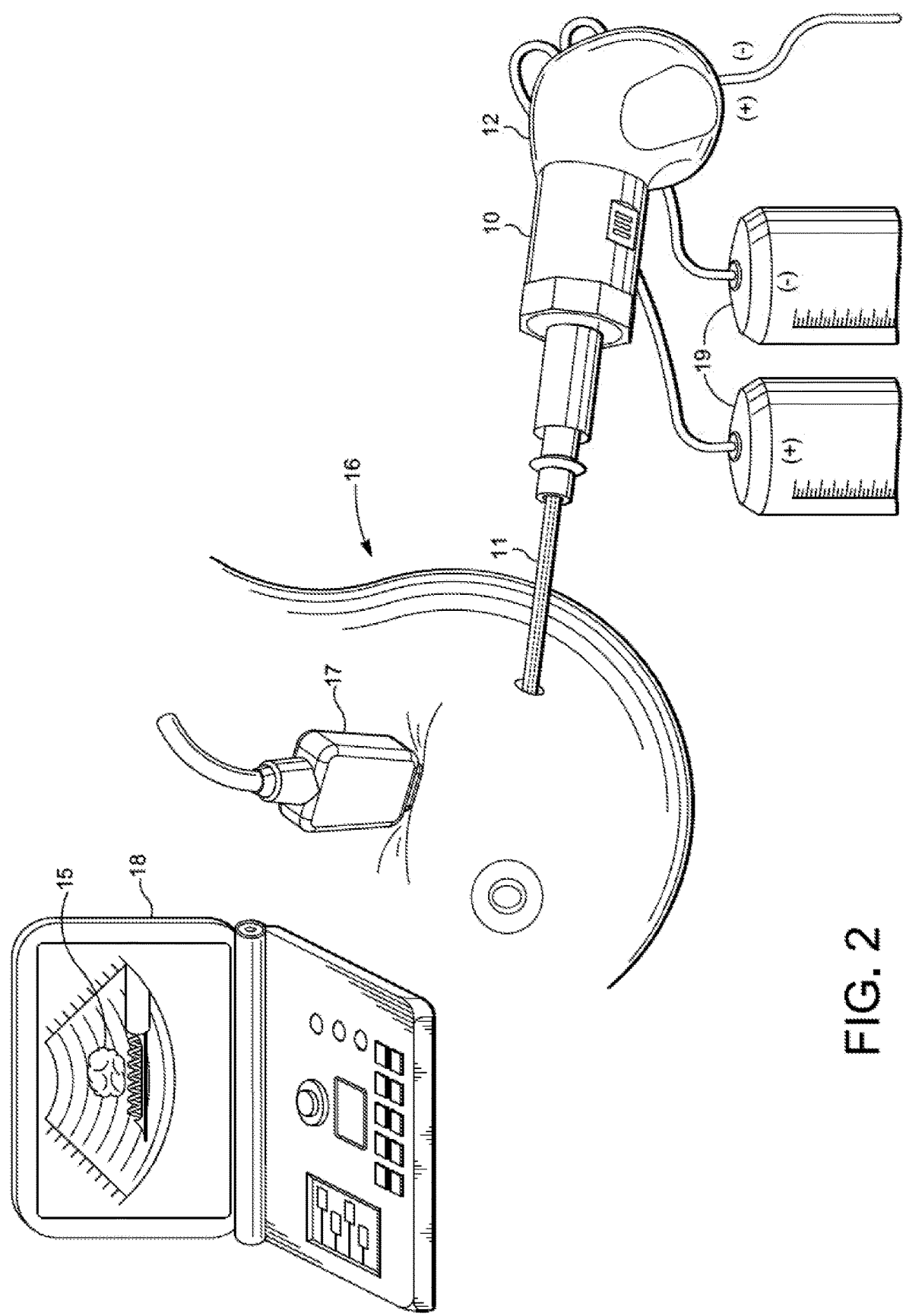
FIG. 2 is a perspective view of the excisional platform instrument or excisional device assembly of FIG. 1.

FIG. 2 is a perspective view of the excisional platform instrument or excisional device assembly of FIG. 1. In FIG. 2, the excisional device 10 is shown with its tip in position inside an organ such as a breast, under or adjacent to a lesion targeted for excision. It should be noted that the position of the device with relation to a target lesion may be described as being "under" or "underneath" the lesion for descriptive purposes and to relate to the Figures as drawn throughout this discussion, which is not considered limiting. As an example, an operator may choose to place the tip of the device at any point adjacent to a target lesion and from any angle in order to use the device correctly and fulfill its intended purpose. Indeed, as an extreme example, an operator may even place the tip of the device directly between two closely spaced target lesions and perform a 360 degree sweep to surround both, the result of which would be that one lesion would be in each hemisphere of the sphere of excised tissue, and both would remain intact and surrounded by clean margins of healthy tissue within the sphere. An ultrasound probe 17 is shown disposed on the surface of a breast, and an ultrasound display unit 18 is shown displaying an image of the lesion targeted for excision along with the excisional device 10 of FIG. 1 in position under the lesion. Indeed, FIG. 2 shows excisional device 10 with its attached tubular introducer assembly 11 inserted into a small skin incision in a breast 16. The tubular introducer assembly 11 is directed at a point under ultrasound transducer 17 on the surface of breast 16. An image of a roughly circular lesion 15 is shown on the ultrasound display 18, with excisional device 10's tubular introducer assembly 11 and cutting assembly 13 in position underneath and a distance (the inferior margin) away from the backside or inferior edge of the lesion (with respect to the skin surface). The handle 12 may be configured to comprise mechanical components for augmentation vacuum, and/or fluid evacuation as well as the delivery of materials including liquids and/or gases and/or devices such as intra-tissue ultrasound probes, and/or other RF or cryo-based instruments. For example, a variety of medications may be delivered, such as local anesthetics, coagulation and/or vasoconstriction elements to help limit bleeding, coupling fluids for conduction of electrical currents and/or to augment steam generation, inert gases such as argon or others, tracer materials and/or implantable marker elements, represented as stored in collection elements (in one embodiment illustrated as bags or bottles) 19. The tubular introducer assembly 11 of the device may be configured with a small cross section for two main objectives: to make crossing through the tissues easy and minimally invasive on the way to the correct position underneath the target lesion, and to facilitate precise visualization and localization of this element, with the least possible distortion of the image. By providing these features in an extremely low profile tubular introducer assembly 11, an operator is able to gently place it in the desired position (e.g., under (or behind)) relative to lesion 15 with a minimum of effort and trauma, Which then encourages repositioning as necessary to make sure that this first step with its critical margin has been achieved as optimally as possible before proceeding with the next steps in the procedure. The cross-sectional dimension of the tubular introducer assembly 11 may be selected from the tubular equivalent of approximately 18 gauge to 10 gauge diameter, and may be tapered as well, while providing a sufficiently stiff base through or over which additional components may be introduced. Other dimensions are possible, depending upon the application and embodiments. The tubular introducer assembly 11 may be configured to be of sufficient length to reach distant target sites such as, for example, about 4 and ½ inches (11 centimeters) to 6 inches (15¼ cm) from the skin surface without the need for a surgical procedure to enable it to reach the site. The excisional device 10 may be used by right and/or left handed persons and/or on staged positions so that in areas of limited access, the excisional device 10 may still be easily positioned for ideal orientation for the purposes of perfuming the subsequent excision under real time or other image guidance (such as ultrasound as shown).

The excisional device 10 may be disposable in whole or in part or may be reusable in whole or in part. Excisional device 10 may be powered electrically by a battery stored in the handle 12 and/or by one or more external power sources through an electrical connector to connect to an external power supply conveniently placed in the handle or proximal end of the instrument. The excisional device 10 may also be powered by sealed rechargeable batteries, which may be configured to be recharged through a wired connection or may be wirelessly recharged using an inductive charging device. Excisional device 10 may alternatively in whole or in part be powered by mechanical energy. Additionally, components of excisional device 10, such as cutting assembly 13, may be energized by sources such as a radiofrequency (RE) generator, connected in bi- or mono-polar configuration, to effect resection alone and/or to augment it, if another mechanism such as mechanical rotation is the principal source of power for separation of tissues.

Figure 3:
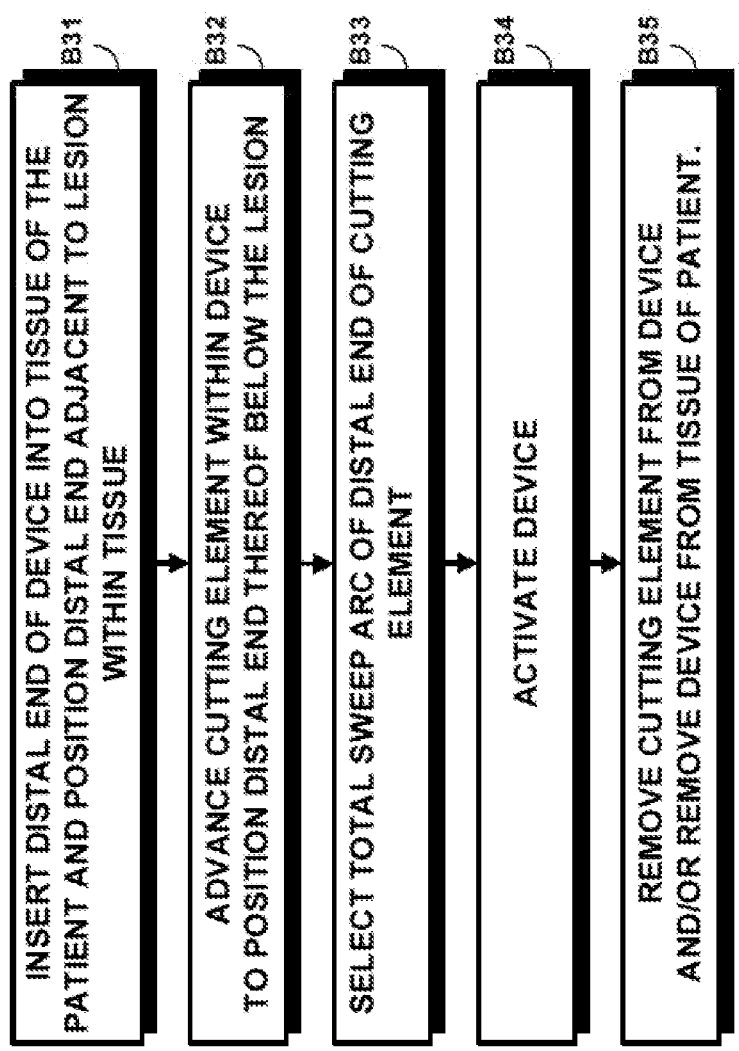
FIG. 3 is a flow diagram describing a method for use of an excisional platform instrument or device assembly, according to one embodiment, to excise tissue targeted for removal in clinical practice, in this example under ultrasound guidance as depicted in FIG. 2.
Figure 4:
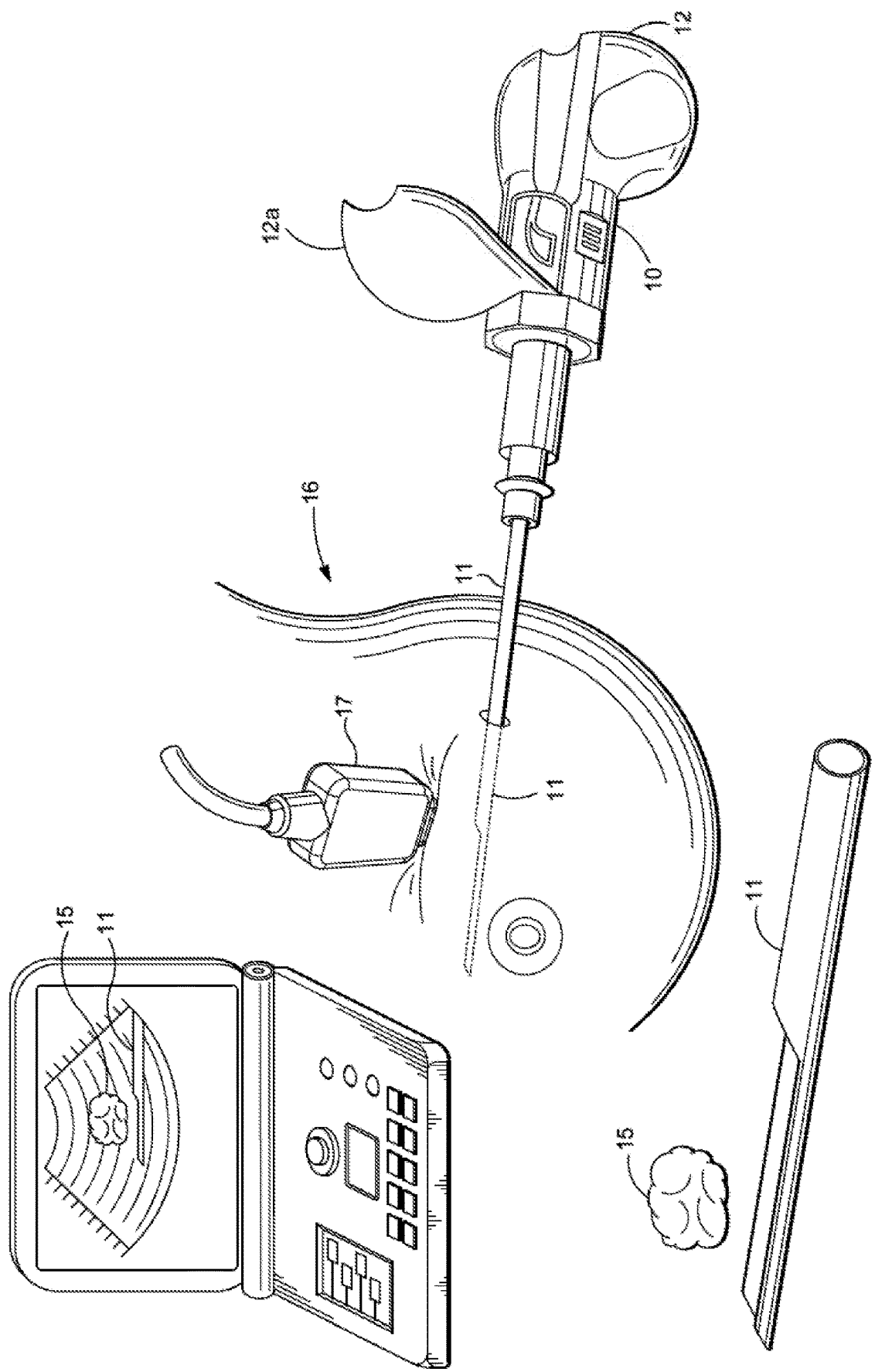
FIG. 4 is a perspective view of a universal introducer component of an excisional platform instrument or excisional device assembly of FIG. 1, according to one embodiment.
Figure 21:
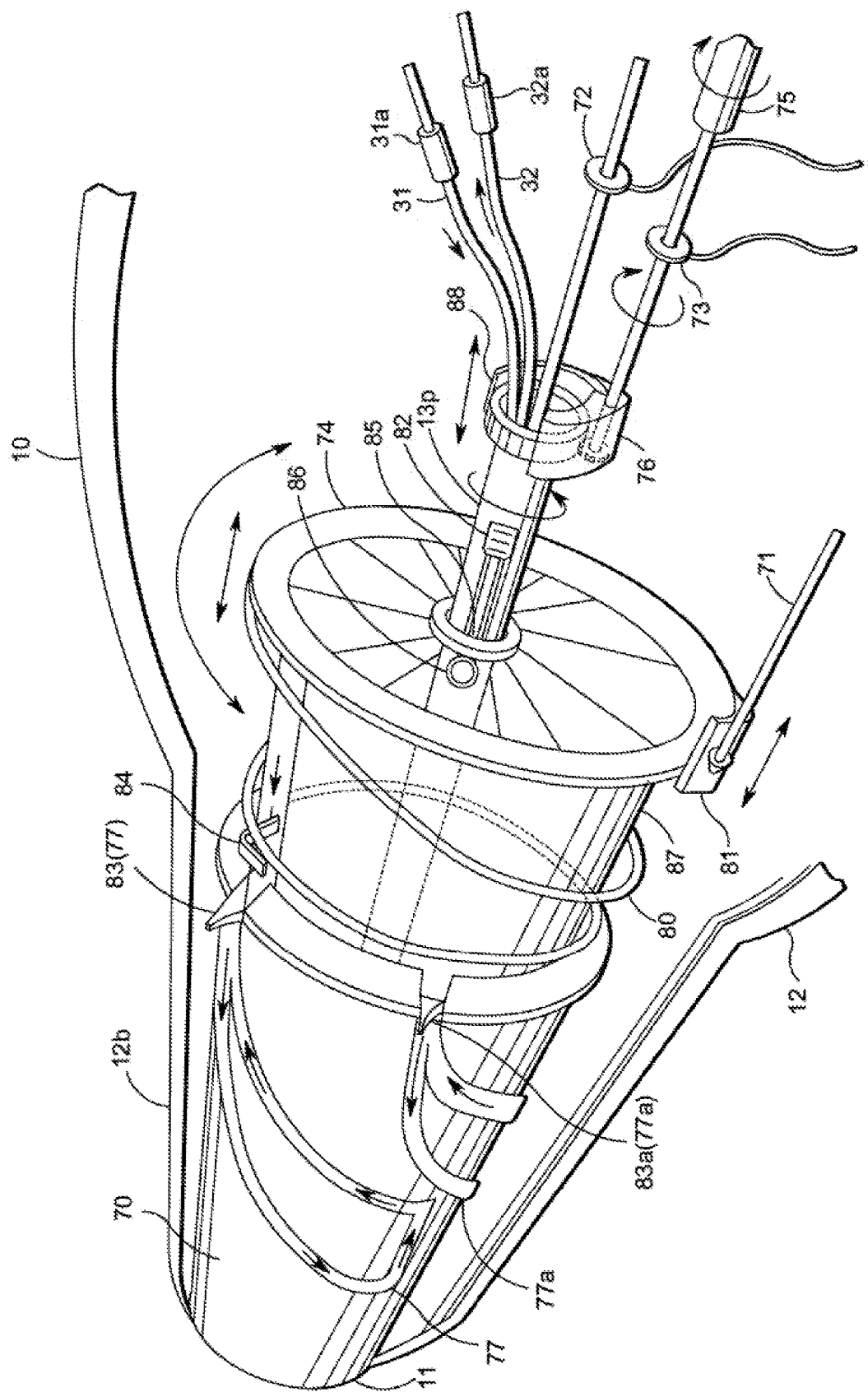
FIG. 21 is a close up perspective view from the handle end of an excisional device showing internal components for driving rotation and powering, including power connections, and revolution cycling for cutting loop elements of an excisional device or device assembly of FIG. 2, according to one embodiment.

FIG. 3 is a flow diagram describing a method for use of an excisional platform instrument or device assembly, according to one embodiment, to excise tissue targeted for removal in clinical practice, in this example under ultrasound guidance as depicted in FIG. 2, According to one embodiment, a method for using the excisional device 10, the tubular introducer assembly 11 and the cutting assembly 13 to excise lesions may be carried out as follows. As shown at block B31, a distal end of the device may be inserted into tissue of the patient and positioned adjacent to a lesion within the tissue. That is, ager making a small skin nick, and achieving local anesthesia in the area of anticipated cutting, the tubular introducer assembly 11 may be advanced into the tissue such as breast 16, to a desired position such as, for example, directly under lesion 15 while maintaining a safe distance from its inferior edge. Imaging guidance may be used to facilitate this, such as ultrasonic guidance, for example. B32 calls for advancing cutting element within the device (if not already present therein) to below the lesion. Indeed, once stabilized in position, the cutting assembly 13 may be placed into excisional device 10 and, if necessary, the rotation/advance function of device 10 may be activated to automatically advance cutter element 13 all the way to the distal end of introducer assembly 11, to a position directly beneath lesion 15, for example. The total sweep arc of the distal end of the cutting element may then be selected, as shown at B33. That is, the total sweep arc radian may then be chosen by placing a channel follower 84 into a desired channel such as 77 or 77a, and the starting point of sweep may be chosen by rotating drum 70 using drum rotation handle 83 as shown in FIG. 21 below. As shown at B34, the device may then be activated by, for example, rotating the cutting element and/or applying RF energy thereto. Indeed, the excisional device 10 may then be activated for cutting while maintaining stable angle and axial position of introducer assembly 11, for example, directly under lesion 15 of breast tissue 16, by observing its position under a guidance method of choice, such as ultrasound. After finishing the excision, the cutting assembly 13 and/or the device 10 may be removed as shown at B35. The device may be removed as a complete assembly with cutting assembly 13. Alternatively, once fully retracted, the cutting element may be removed from the excisional device 10 by pressing button 82 of FIG. 21 and withdrawing cutting assembly 13, which may then be replaced with collecting or other elements for subsequent procedure stages FIG. 4 is a perspective view of a universal introducer component of an excisional platform instrument or excisional device assembly of FIG. 1, according to one embodiment. In FIG. 4, the introducer assembly 11 is shown in position in an organ such as a breast 16, without other components yet in place, and the way its introducer tray element and tip would appear in correct position underneath a target lesion, for example within an organ's tissue under ultrasound guidance. In particular, FIG. 4 shows an excisional device 10 with its universal introducer tray/tube pointing at a point underneath a target lesion 15 within a breast 16 as visualized under an ultrasound guiding probe 17. The introducer assembly 11 is shown in FIG. 4 as projecting forward through a small skin incision, and as it would appear under ultrasound imaging in relationship with target lesion 15 on display 18, as well as enlarged, showing a general, sharp low profile shape below the illustration, again, below a target lesion 15. FIG. 4 also shows device 10 with its handle cover 12a hinged open upward to permit access to the internal areas for purposes of inserting additional components therein, such as cutting (e.g., band/loop) element 13, through introducer assembly 11 in correct position under target lesion 15. In order to facilitate advancement of additional components, introducer assembly 11 may be rotated to provide room within the organ's tissues. Alternatively and/or additionally, components such as cutting assembly 13, may themselves be activated, energized, rotated or a combination of any or all of these. In addition, such components may themselves be of low profile, streamlined and/or sharpened in order to facilitate their introduction to the correct position for their proper function(s).

As shown in FIG. 4, the introducer assembly 11 may define a distal portion that may be shaped, according to one embodiment, as an elongated scoop or scoopula. The distal tip of the introducer assembly 11 may be pointed, to best cut tissue as it is advanced therein. It is to be noted that the present device may be used without the cutting assembly 13, or after the cutting assembly 13 has been retracted from the introducer assembly 11. Indeed, once the introducer assembly 11 is in place (i.e., when the distal tip of the scoopula of the introducer assembly 11 is disposed as desired within the procedure site), the device 10 may be decoupled therefrom, leaving the introducer assembly in position with the scoopula-shaped distal end thereof adjacent the structures of interest. Therapeutic/beneficial agents may then be delivered through the introducer assembly 11. Moreover, devices such as ultrasound devices may be inserted therein and the distal, working end thereof may be positioned at, near or past the distal end of the introducer assembly 11. Imaging or delivery of agents and/or materials may then take place, and the device 10 optionally re-coupled to the introducer assembly 11 for further action.

As shown in FIGS. 1 and 1a, the introducer's distal tip may also comprise a raised distal feature, which will be more closely illustrated in following figures, according to embodiments. The distal end of the cutting assembly 13 may abut and/or be secured to this raised distal feature. In this manner, as the cutting element is pushed in the distal direction (i.e., away from the operator), the cutting assembly 13 tends to push against the raised distal element and bow out from the opening of the distal, scoop-shaped portion of the introducer, as shown in FIG. 1a. At least the helical portion of the cutting assembly 13 may be rotated and/or RF-energized as the cutting assembly 13 bows out.

Figure 5:
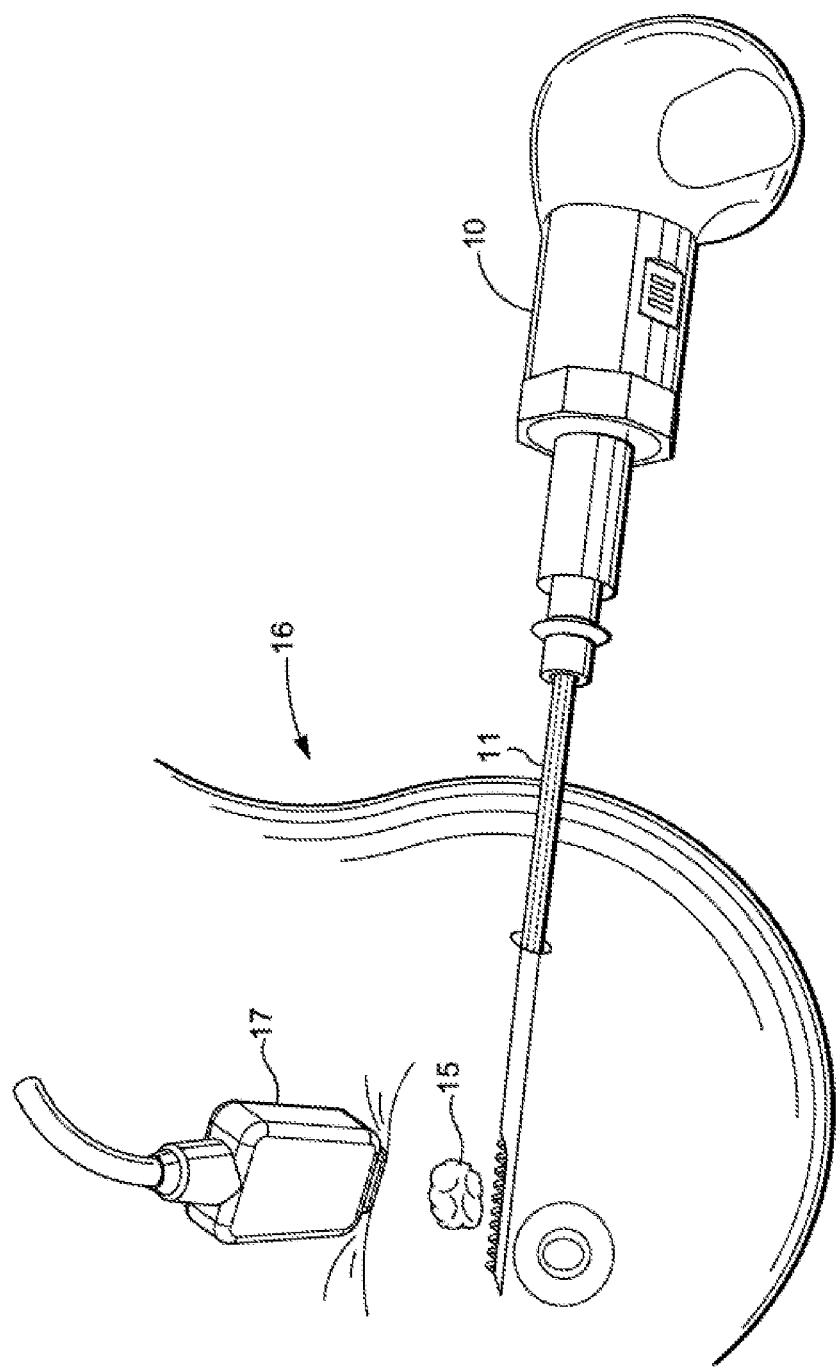
FIG. 5 is a perspective view of an excisional platform instrument (hereafter described as an "excisional device" for simplicity) or device assembly of FIG. 2, according to one embodiment.

FIG. 5 is a perspective view of an excisional device 10 according to one embodiment with its excisional loop component (including the cutting assembly 13) in a non-extended position within an introducer assembly disposed position underneath a lesion 15 that is targeted for removal. Indeed, FIG. 5 shows an example of such an arrangement, with introducer assembly 11 of excisional device 10 correctly positioned under a lesion 15 under ultrasonic guidance 17, with cutting assembly 13 in its non-extended configuration in the distal end of introducer assembly 11.

Figure 6:
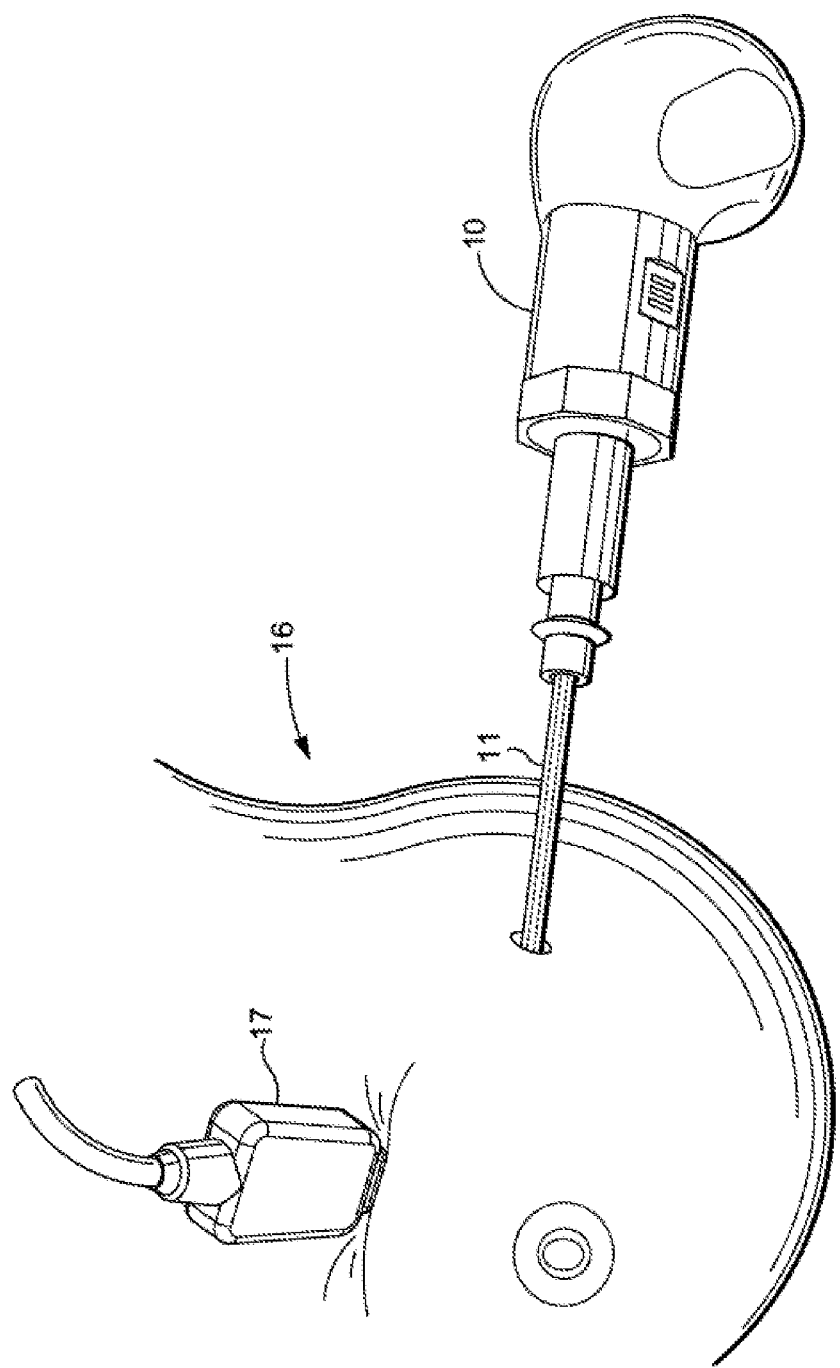
FIG. 6 is a view of an excisional device of FIG. 2 within a breast, according to one embodiment.

FIG. 6 is a view of the excisional device 10 of FIG. 2 within a breast 16, according to one embodiment. According to one embodiment, the excisional device 10 may be inserted within the breast 16 via a small incision in the dermis. FIGS. 6a-6e also show a series of illustrations showing a loop cutting element in various stages of storage, extension and revolution about a lesion targeted for excision represented by a spherical shape over the top of introducer assembly 11. Indeed, FIG. 6a shows an excisional loop component in resting, non-extended position, retracted within introducer assembly 11. FIG. 6b shows the loop component (which includes cutting assembly 13) in an extended configuration, while FIG. 6c shows the position of the cutting loop about halfway through its excisional revolution about a lesion targeted for excision assuming a counter-clockwise rotation, and FIG. 6d shows completion of revolution of the cutting loop component. FIG. 6e shows the cutting loop in complete re-retraction following successful complete excision of a lesion targeted for excision based on the movements or extension, revolution and retraction as depicted in this series of figures showing various snapshots of sequential stages of excision, according to one embodiment.

In greater detail. FIGS. 6a through 6e show a profile series of cutting assembly 13 and introducer assembly 11 of excisional device 10, as if viewed through tissue such as a breast. In 6a, cutting assembly 13 is shown in retracted position, as it would appear upon advancement of this component to the distal end of introducer assembly 11. In FIG. 6b, the cutting assembly 13 is shown advanced further distally and in a bowed configuration. Indeed, since the tip of the cutting assembly 13 is prevented from moving further in the distal direction past the distal tip of introducer assembly 11, it bows outward from its base position within introducer assembly 11, severing tissue in its path which, in this case, comprises tissue that partially surrounds the target lesion 15. FIGS. 6c and 6d show snapshots of the revolution pathway as cutting assembly 13 continues to sever tissues surrounding lesion 15, at a safe distance from the edges of lesion 15, thus providing a safety margin of clean tissue surrounding the lesion. This safety margin of tissue may be later removed with the lesion to insulate components of the lesion from contacting other tissues within the organ during removal, as well as to provide a volume of reference tissue surrounding abnormal lesion tissue upon closer, definitive evaluation of the removed tissue, as well as potentially the lining of the space left behind in an organ such as breast 16. FIG. 6e shows loop cutting assembly 13, returned again to its fully retracted configuration within the distal portion of introducer assembly 11, after completely excising target lesion 15 along with a border of non-abnormal tissue completely surrounding lesion 15 on all sides.

FIGS. 7a through 7e show the various pathways taken by the cutting assembly 13 of one embodiment of excisional device 10 of FIG. 1, relative to lesion 15. The pathway taken by the cutting assembly 13 and the resultant 3-dimensional shape 2 of the excised mass of tissue, comprising a surrounding volume or layer of non-abnormal tissue completely enclosing a target lesion 15, is shown in FIG. 7a, as seen if looking upward from an inferior perspective position, with introducer assembly 11 visible in position below target lesion 15, with the cutting assembly 13 about halfway through its travel. Two additional views, FIG. 7b showing an excised tissue shape from the side and FIG. 7c showing the same excised tissue from an end-on perspective, assuming a 180 degree sweep was chosen, further demonstrate the surrounding safety margin of non-abnormal tissue excised by this embodiment. FIGS. 7d and 7e show, from end-on perspective, the shape resulting from choosing various sweep angles, with FIG. 7d showing an approximately 90 degree sweep and FIG. 7e representing any of a multitude of angles (a) that may be freely chosen by an operator of excisional device 10. In all cases, the side view would be similar to that shown in FIG. 7b, assuming that full deployment (outward bending or bowing) of cutting assembly 13 assumes this shape. Other shapes may be chosen such that the sides of the shape (and sides of cutting assembly 13 as well), and/or convex downward shape at the top, which in this case is shown as an exemplary arch shape, may be altered. In the helical configuration of cutting assembly 13, as shown, cutting/resection takes place by either rotating the helical component about its longitudinal axis or about an interior axial element 3 (best seen in FIG. 7a) about which the cutting assembly 13 is wound and/or an internal element such as a band's longitudinal axis, and/or energizing this component for cutting with energies such as microwave, ultrasound, radiofrequency in the "RF" frequency typical of other surgical applications such as with the "Bovie" cutting wand, or other energies such as harmonic wave forms of ultrasound frequencies for example. In all cases, cutting takes place in the direction of pressure against the tissues encountered during the expansion, revolution and retraction pathways. Additionally, these same properties may be used for introduction of cutting assembly 13 along introducer assembly 11, and/or as in combination with introducer assembly 11, should tissues be extremely dense, fibrous, or otherwise resistant to penetration. The helical direction may be chosen to "pull" cutting assembly 13 into position while it is being rotated, thus requiring less effort on the part of an operator of excisional device 10 to position the device, thereby permitting a more gentle approach and easier visualization of the lesion 15 and excisional device 10 including its components during that phase of the procedure.

FIGS. 7a through 7e also demonstrate the smooth, compact shape of the excised tissue, which represents a distinctly different and advantageous result compared with the jagged and irregular shapes obtained using conventional open surgical excision devices and techniques. The predictable, consistent, smooth and compact nature of excisions according to embodiments permits easier evaluation of both the removed mass as well as the tissue bed from which the intact specimen was removed. In addition, far more precise centering of the intact lesion within the excised specimen is possible with this approach, as well as precise control over the size of the surrounding margin of non-abnormal tissue. The precise sizing and centering of the lesion within the excised specimen are beneficial to follow up irradiation or other visualization, implant or treatment means of the remaining tissue bed surrounding the space from which the specimen was excised.

FIG. 8 shows the excisional device 10 of FIG. 2 in position within a breast 16, according to one embodiment. FIG. 8 shows the manner in which loop cutting assembly 13, in extended position and about halfway through its revolution about a lesion 15 targeted for excision, achieves such excision with a margin of included normal or nearly normal breast tissue within the excisional margin, according to one embodiment. FIG. 8 also shows the manner in which an extended loop component may appear on an ultrasound display 18. FIG. 8 shows the appearance of the expanded, bowed cutting assembly 13 of excisional device 10 of FIG. 1, surrounding a lesion 15 within a breast 16 and the way it would appear if one were able to see directly into the breast, and the way the instrument assembly 10/13 would appear on ultrasound imaging display 18. In this case, the (+) and (−) polarity symbols represent ionic charges provided, for example, by flushing an electrolyte solution or gas from elements (e.g., bags or bottles) 19 within the tissues surrounding lesion 15, through cutting assembly 13 and/or introducer assembly 11. These symbols may also represent radiofrequency energy as may be generated when the device is in a bipolar configuration where, as shown, the RF energy originates from a lead 19a coupled to the device 10 and to an RF generator, such as a RF surgical unit, and returns via cutting assembly 13 to its generator source.

FIG. 8a shows a side view of a partially completed cutting assembly 13, in a size that may be representative of an actual instrument, for excising lesion 15 in tissues such as breast 16. In this state, the helical cutting element 13 is partially wound about an interior axial element (e.g., band) 31.

Figure 9:
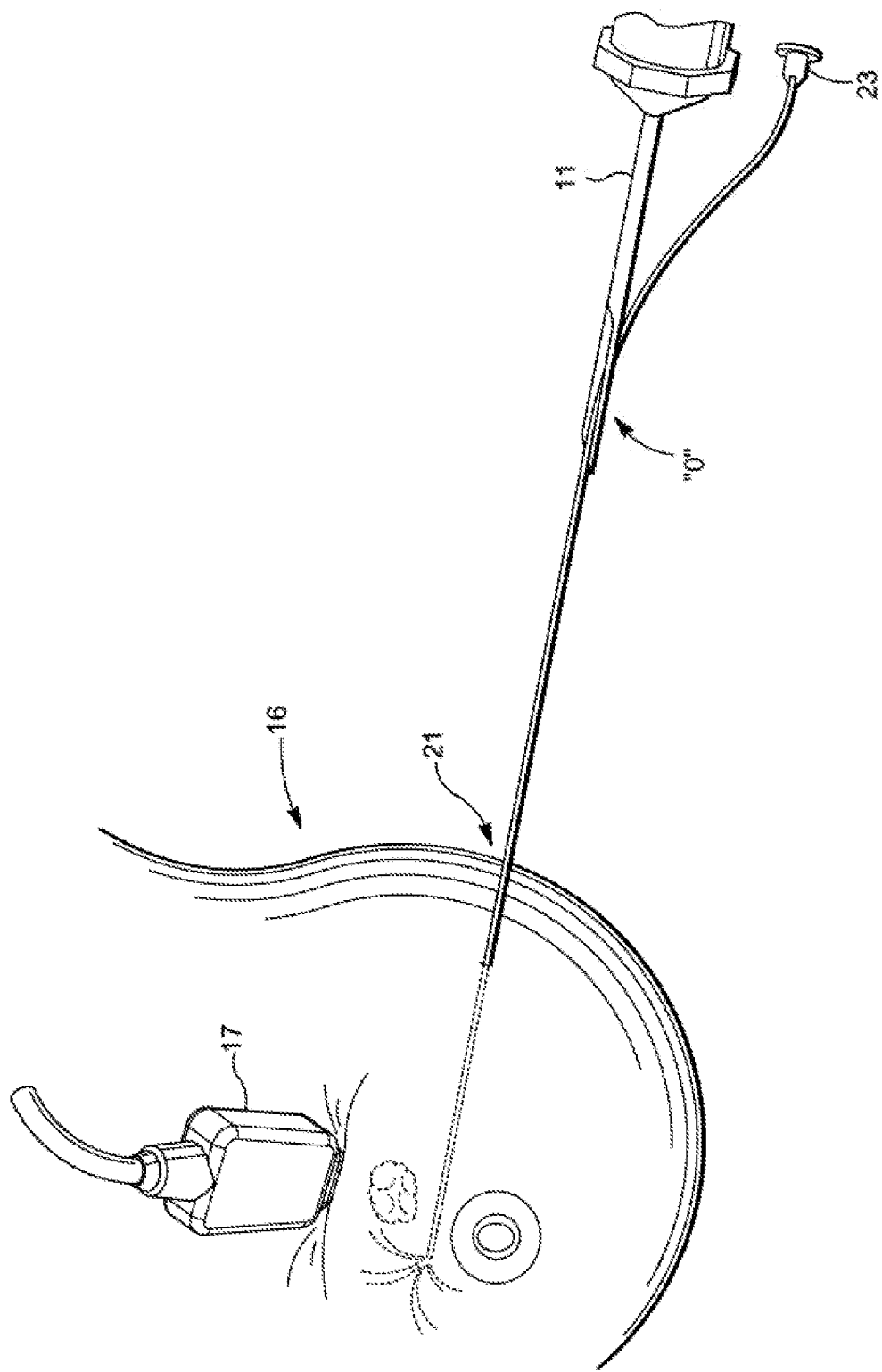
FIG. 9 shows, in side view, a guiding element wire and/or tube showing the way it would be placed in relationship with a lesion targeted for removal within and from a breast, according to one embodiment.

FIG. 9 shows another component 21 that may be introduced through and/or in association with, introducer assembly 11 of excisional device 10. In FIG. 9, component 21 is shown as a guide element or assembly with an external coupler or hub type connector 23. As shown in FIG. 9a, the guide assembly 21 may comprise stabilizing projections 25 at the distal tip thereof and additional stabilizing/injecting tube(s) 24. Guide assembly 21 may be introduced through its own needle introducer (not shown) which, after proper positioning, may be withdrawn, leaving guide assembly 21 in place in a useful position such as under lesion 15 for example. Thereafter, the excisional device 10's introducer assembly 11 may be introduced into favorable position over guide assembly 21 with ease and precision. Guide assembly 21 may comprise one or more stabilizing projections 25 and/or injecting tube components 24, either or both of which may automatically or manually be caused to flex outward upon withdrawal of its introducing needle (not shown), entering tissue of an organ such as breast to enable element 21 to be stabilized for subsequent positioning of additional components such as introducer assembly 11 over element 21 and for anchoring and/or reference purposes. Because guide assembly 21 may have an extremely low profile, it may be the easiest to introduce and may facilitate the subsequent introduction of larger-profile components. For example, according to one embodiment, one such larger profile components may comprise an additional insert cannula 28 as shown in FIG. 9a. In this instance, insert cannula 28 may be threaded gently with rotation and forward pressure as needed over guide assembly 21/24/25, and once positioned near the far or distal end and in desired position, such as directly under lesion 15, then introducer assembly 11 may be introduced over insert cannula 28 and advanced in a similar manner to the desired location, such as directly underneath lesion 15, for example. Additionally, insert cannula 28 may be used to re-straighten stabilizing points 25 and/or stabilizing/injecting tube(s) 24 to enable easy removal thereof from tissue such as breast 16. Alternatively, these elements may be retracted from tissue without re-straightening, or needing to reintroduce the introducing needle (not shown here, since it is generally a standard component of guide wire kits as used for this purpose).

Guide assembly 21 may comprise additional features such as a hollow tubular component 24, shown in FIG. 9a, which may be used to deliver liquids, gases or other forms of materials and/or phases. The hollow tubular component or components 24, according to one embodiment, may enable the introduction of local anesthetics, marker elements, tracer elements, dyes, pro-coagulants, electrolytes, antimicrobials, inert gases and/or other substances, via a removable attachment connector point such as hub-type connector 23. Advantages of a stepwise procedure at this stave include easy visualization as depicted in FIG. 9b. As shown, guide assembly 21 may be seen as displayed on a display 18 enabling visualization of ultrasound or other imaging modality. The guide assembly 21, for example, may enable the delivery of agents that enhance imaging, that increase echogenicity/recognition, and/or enable the injection of agents that enhance imaging in other ways, such as foamy liquids, dyes or other materials that enhance imaging and/or image contrast. According to embodiments, the structures described herein allow for an easier procedure to learn for inexperienced operators and one that is potentially far easier to control and perform more gently, with minimal trauma and with more precision. FIG. 9c depicts a two-piece connector assembly with a flared threaded component 26 with inner flared surface for interface with an O-ring at position 26a, as placed over smooth section of guide tube/wire 21/24, such that threading component 27 onto component 26 draws tight its tapered end against the O-ring, compressing it down tightly against the outer smooth section of 21/24, and tightly against its inner tapered section 27a, as well as inner tapered segment of component 26, to create a tight seal surface. Assembly 23 (including elements 26 and 27) is then ready for attachment to a syringe such as 29, via a "luer" type connector or threaded connector, as shown at reference numeral 27b in FIG. 9c.

Figure 10:
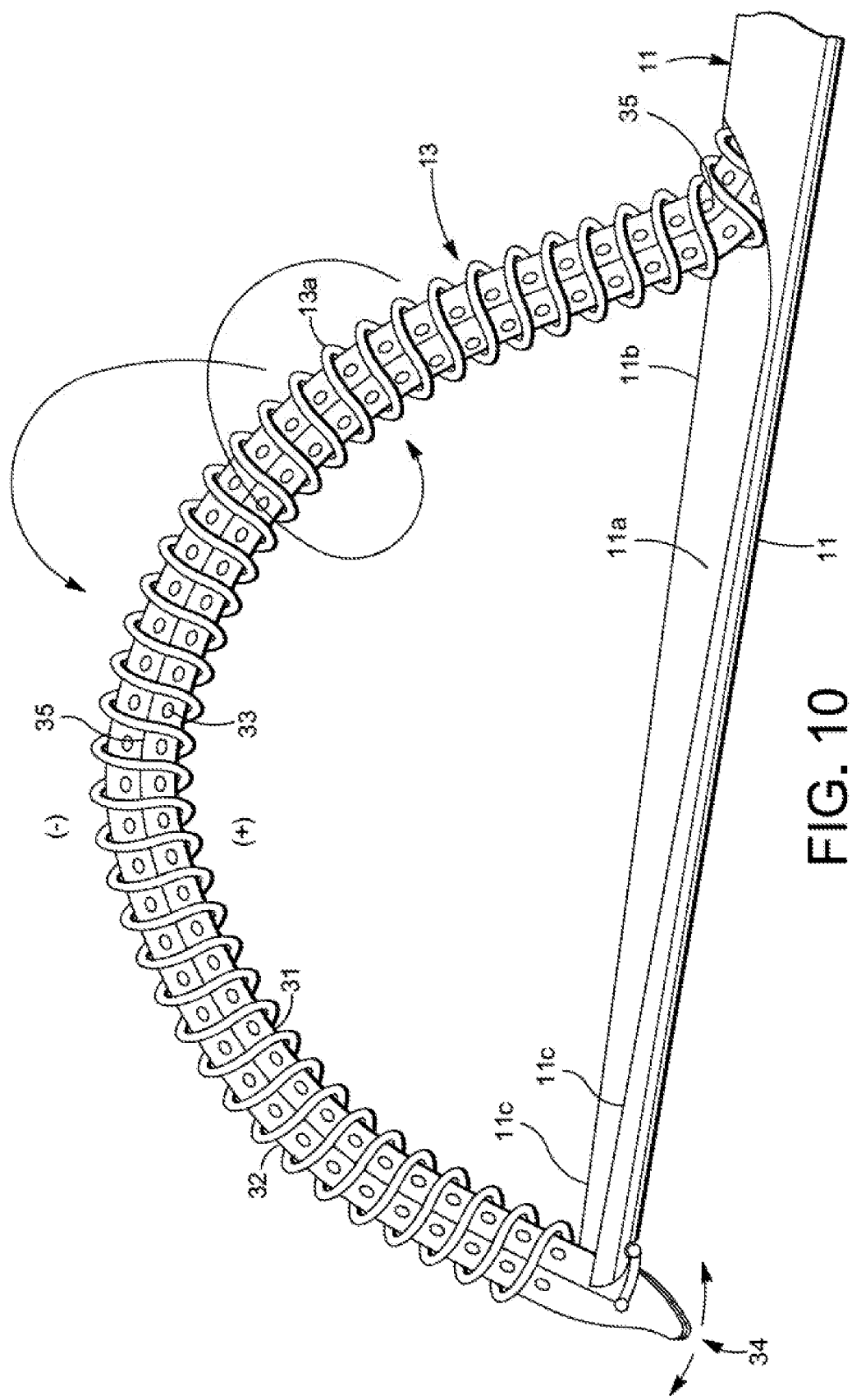
FIG. 10 is a side close up view of a universal introducer tray element and a helical excisional component of an excisional device assembly of FIG. 2, according to one embodiment.
Figure 10C:
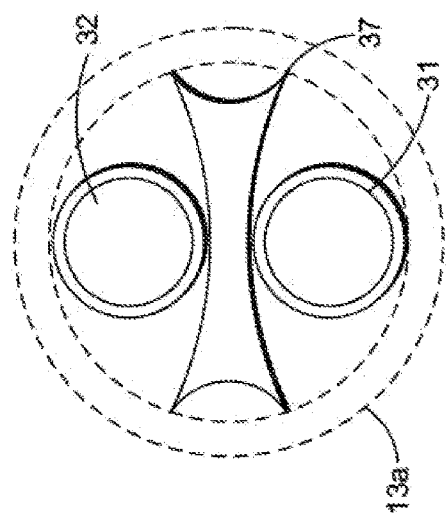
FIGS. 10a, 10b, 10c, 10d, 10e and 10f show various cross sectional views of various embodiments of a helical excisional component and universal introducer tray of an excisional biopsy device assembly of FIG. 2, according to embodiments.
Figure 10F:
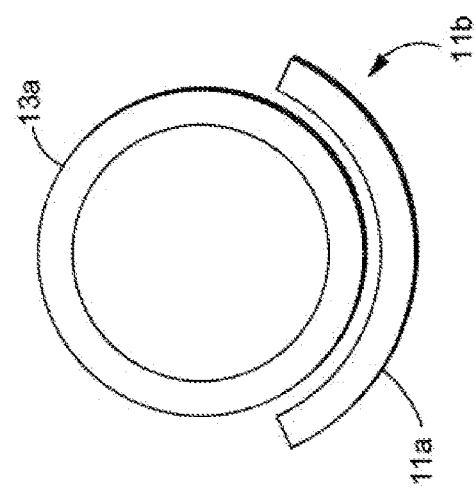
Figure 10B:
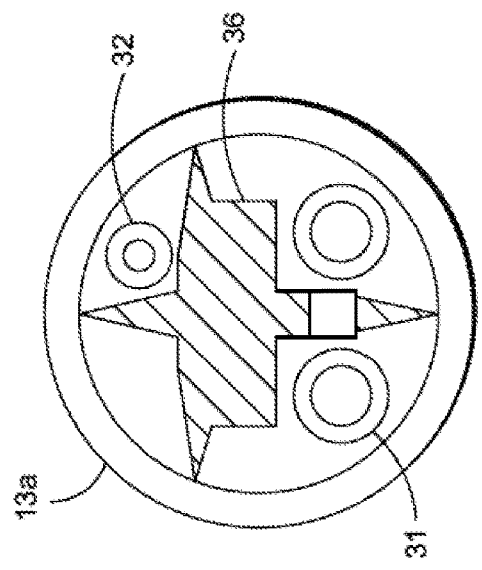
Figure 10E:
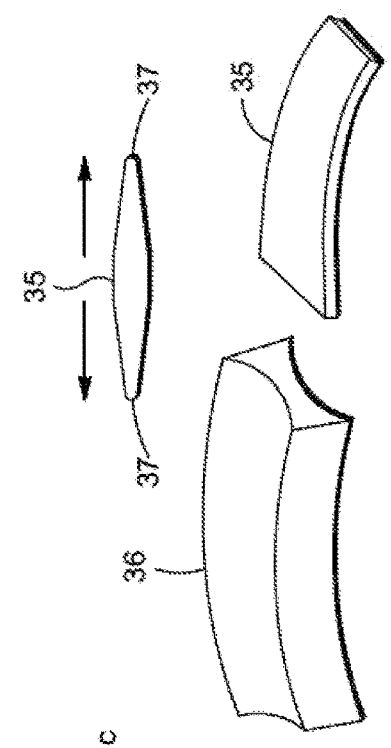
Figure 10A:
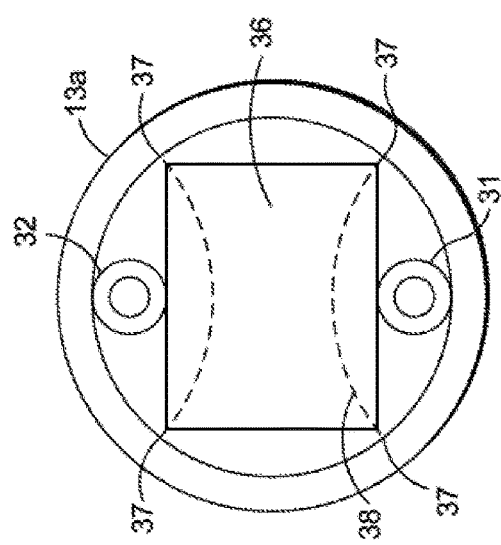
Figure 10D:
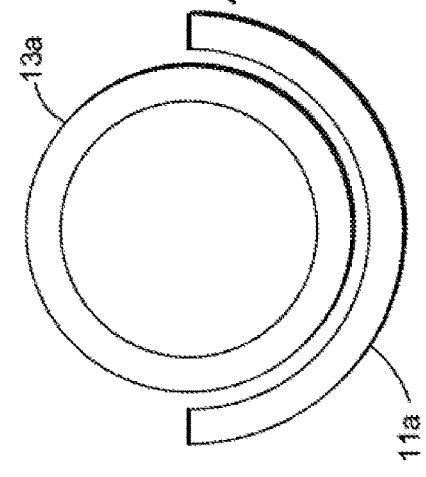

FIG. 10 is a side close up view of an introducer assembly and a helical excisional cutting assembly 13 of the excisional device 10 of FIG. 2, according to one embodiment. FIG. 10 shows various components of a cutting assembly 13, which is depicted in an extended position with respect to the introducer assembly. FIGS. 10a, 10b, and 10c show various cross-sectional views of components internal to such a helical cutting assembly 13, according to embodiments. FIGS. 10d and 10f show cross sections of a helical cutting element nesting within cross-sectional depictions of the introducer assembly 11. FIG. 10e also shows various examples of cross sections of basic band elements of a cutting loop component of the excisional device 10 of FIG. 2.

FIG. 10 and FIGS. 10a through 10f show a number of embodiments of a cutting element/cutting assembly 13, bowed outward from the scoop-shaped distal portion (according to one embodiment) of the introducer assembly 11. Starting with details of introducer assembly 11, this embodiment shows a reverse-tapered trough section designated 11b and 11c, which may be forward tapered, or not tapered at all, depending, on application and embodiments, tissue characteristics or other factors. According to one embodiment, an exposed upper portion allows cutting element or assembly 13 to project upwards and bow outwards through a top opening, above and from introducer trough 11a, and in such a way that rotation of introducer assembly 11 about its long axis would carry this opening and with it together with the cutting assembly 13 such that a volume of revolution of cutting assembly 13 about a target site or intact lesion may be defined.

Turning now to details of components and configurations of cutting assembly 13, shown in FIG. 10 is a helical cutting element 13a, which is rotatable along its longitudinal axis such that a cutting action is achieved where its surfaces interact with tissue with which it comes into contact. The distal end of cutting assembly 13 may abut a swivel type end attachment 34 at the distal end of introducer assembly 11 to allow it to be deployed by the operator. Additionally, these surfaces may be configured to be energized with a variety of energy types, strengths, frequencies or other variations. Helical cutting elements 13a are shown surrounding additional components including an interior axial element (e.g., band) shown in FIG. 10 as a band element or elements 31 and shown in cross-section at reference 36 in FIG. 10a. The band element, according to further embodiments, may have more complex shapes such as shown at 36 in FIG. 10b, and configured with edges also of varying configurations as shown at 37. According to embodiments and different implementations, these shapes may be optimized in terms of sharpness of edges, for example in the direction of cutting, such as when the band element 31 is bowed outward, revolved and retracted back inwards. Coating all surfaces with an insulating material, for example, other than these relatively sharp leading edges (leading one or more of the directional cuts above), may be used to significantly increase energy density by significantly decreasing exposed surface area. Insulation may also be added between bands, such as at 35 of FIG. 10, Additionally, these cutting edges such as represented by 37, may be wiped and/or scraped off constantly by rotational action against the helical cutting elements 13a. Also, these surfaces may be kept at a slight distance from direct tissue contact, such that arcing or "spark" energy flow may be reliably maintained due to maintenance of, or continuously repeating creation of, the tissue "gap."

Optional tubular components may also be included within the cutting assembly 13, which optional tubular components may be used to deliver agents and to retrieve/evacuate the same or other materials, both liquid and/or gaseous in nature, such as smoke, steam or other vapors, hot or cool liquids and others. The flow of such liquids and/or other materials is depicted by (+) and (−) polarity symbols, which, in the instance of delivering cooling liquids for example and evacuating steam, smoke or other undesired compounds, may be advantageously arranged such that efferent or delivery flow (+) may take place, for example, via tubular element 31 (on the inside radius of cutting assembly 13), while evacuation flow (afferent pathway) may take place on the outer radius of cutting assembly 13. This flow pattern may be reversed in the situation where it may be desirable to deliver cutting augmenting materials (steam, noble gases or other) on the outer radius of cutting assembly 13 throughout the procedure and/or on the outer radius area during outward bowing and on the inner radius during inward retraction of cutting assembly 13. In either case, these agents may be delivered and retrieved through fenestrations (i.e., openings) 33 defined within tubular elements (e.g., axial band element(s)) 31 and 32 of FIG. 10 and FIGS. 10a through 10c. According to one embodiment, agents may be delivered through these fenestrations 33 and retrieved via a tubular opening portion of introducer assembly 11. Alternatively still, agents may also be delivered and or retrieved by any combination of elements 31, 32 and introducer assembly 11. For example, it may be desirable to deliver pro-coagulants, local anesthetic agents or the like via one or more pathways, without evacuating any of these substances. FIGS. 10a-10f show additional configurations of the components described above. Motions associated with these configurations may be seen as arrows on band element 35 in FIG. 10e, which motions may include oscillation, sawing actions, or other motions used to manipulate or sever tissues. Other configurations may occur to those of skill in this art and all such alternate configurations should be understood to fall within the scope of the present disclosure. Surface treatments may be applied to optimize function and different implementations of the helical cutting element 13a (including, for example, serrated edges) may be incorporated into the present device without, however departing from the scope of this disclosure.

Figure 11:
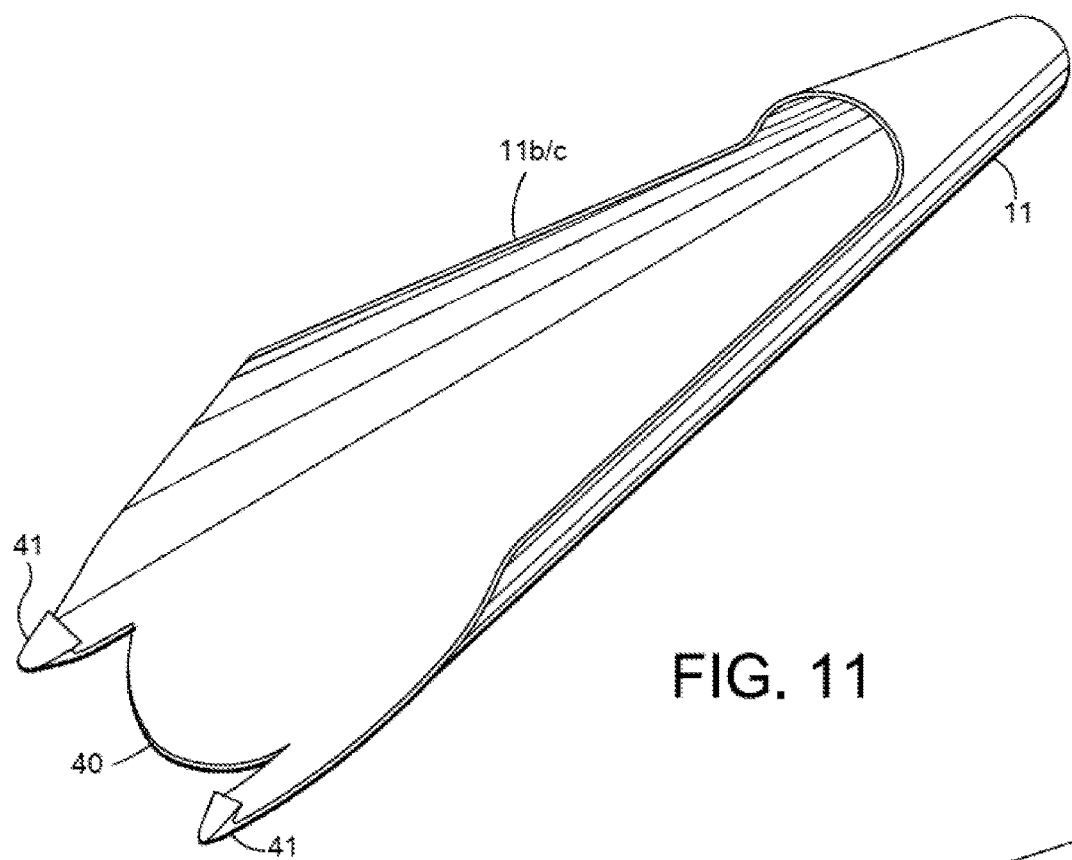
FIG. 11 is a perspective, end-on view of a distal segment of a universal tray component of an excisional device of FIG. 2, according to one embodiment.

FIG. 11 shows one embodiment of the introducer assembly 11 of FIG. 10, showing a perspective view from the front tip or distal end thereof. According to one embodiment, forward/distal edge 40 and forward/distal edges of stops or abutments 41 (and optionally also, side edges 11b/c) may be sharpened such that they are effective to cut tissues while being rotated in either direction and/or also moving in a simple axial direction distally (distally refers to a direction with respect to proximal handle 12 of FIG. 1), as well as having the option of energizing one or more of these surfaces in order to augment cutting forward for placement in the tissues with the least effort. The shapes of these edges 40 and 41 are configured such that they may also perform specific interaction functions with other elements passed through and over introducer assembly 11. The shape of the sharp cutting tip elements 40 may be formed by straight angle cutting of a basic tube such as stainless steel hypotube. As shown, the distal end of the introducer assembly 11 may comprise an arcuate edge surface 40 such that a secant passing through the endpoints of the arcuate edge surface is generally perpendicular to the longitudinal axis of the introducer assembly 11. Adjacent the endpoints of the arcuate edge surface 40 are projections that extend more distally than the arcuate edge surface 40 and terminate in locally thicker stops 41. Stops 41 may be provided as shown and in other configurations, which are effective to prevent distal movement of introduced elements, such as cutter assembly 13, FIG. 10. Stops 41 such as these may have a hooked configuration, as shown in FIG. 11, to prevent an introduced element's edges from inadvertently riding up over the top of these components. As will be shown in subsequent illustrations, such shapes may serve to enable movements, anchoring and release of additional elements introduced via this assembly. Formed in this way, the edges of the cutting tip elements may engage and retain the additional elements (not shown). In this manner, the final shape includes elements that do not add significantly to dead space projecting more distally and may anchor distal ends of introduced elements during revolution of the entire assembly when fully engaged and bowed outward, as shown in subsequent illustrations. It should be noted that although in FIG. 11, stops 41 act as a forward abutment for other elements to be contained thereby, the introduction of other elements may not require such a feature in order to deploy outward from introducer assembly 11 and perform their functions. Indeed, other assemblies designed to be introduced in vivo through the introducer assembly 11 may have self-deployment features, such as arching outward from the open end of introducer assembly 11, as will be described in further figures and still deploy substantially from the extreme end of the introducer assembly 11 with no tip end dead space.

Figure 12:
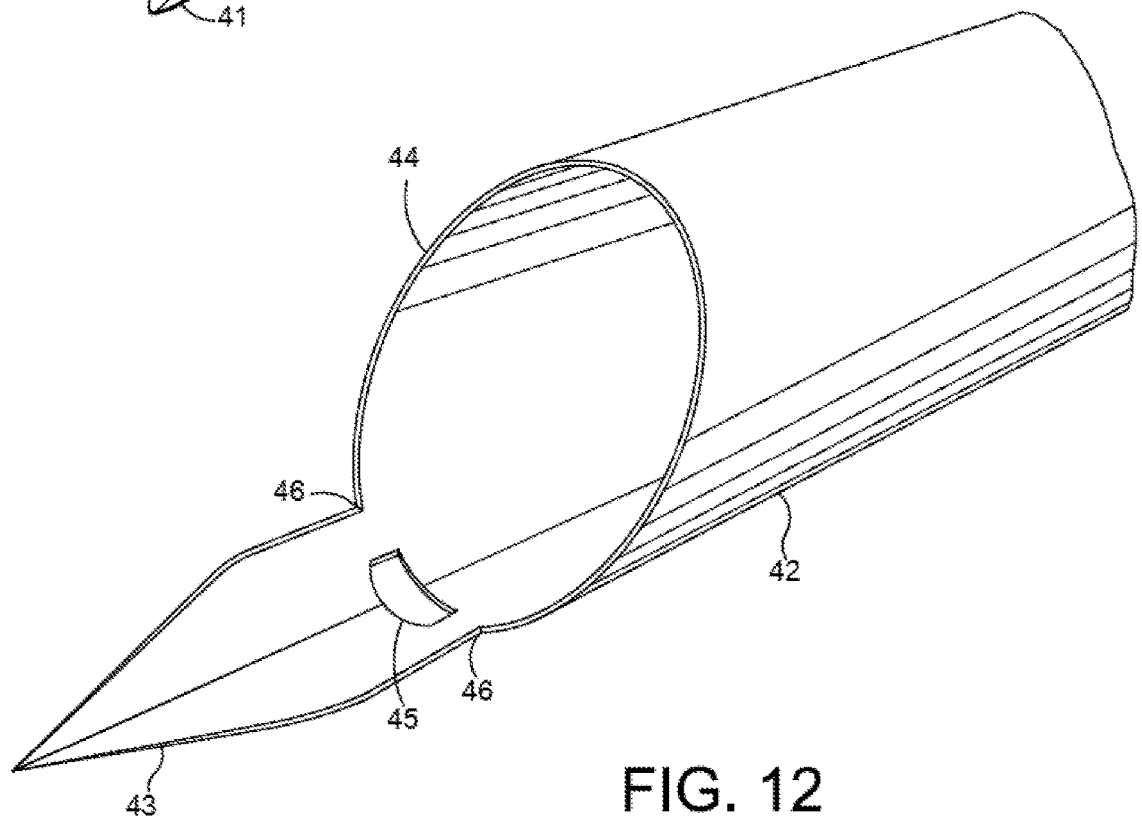
FIG. 12 is an end-on perspective view of a distal segment of a portion of a cutting loop element showing details of a distal end for interacting with a universal introducer tray element of an excisional device of FIG. 2, according to one embodiment.

In FIG. 12, a similar distal end-on, looking proximally, illustration shows the distal tip of an element 42 that may represent part of cutting assembly 13 of FIG. 10 with a distal tip 43, which may be sharpened and shaped to easily penetrate tissues by advancing distally in a longitudinally axial manner, according to one embodiment. This edge as well as edge 44 may likewise be energized to permit easy cutting/penetration/electrosurgery as it is being advanced, and likewise, may be physically rotated about its longitudinal axis in order to facilitate distal advancement. A slot 45 may be provided, of a dimension and shape that enables the distal edge of introducer assembly 11 to automatically slip over and optimally engage while bowing upward of the more proximal shaft portion of 42, which may itself be a flexible tube, with downward swinging of distal tip 43, while at the same time allowing cutting assembly 13 or other introduced assemblies to rotate about their own longitudinal axis. Additionally, the lower distal edges 46 of edge 44, whether sharpened or not, may serve to engage stops 41, which act to restrain an introduced component thus equipped with this or a similarly functioning element, from moving further distally, and also as a fulcrum axis for component 42 around which to swing vertically. In this action, a cutting element thus constrained from moving its tip forward would be forced to bow outward (upward in this illustration and in subsequent illustrations) as more axial force is applied in a distal direction from a position proximal to the bowing region of an element such as cutting element/assembly 13 of FIG. 10. As the distal tip portion of such an element swings downward with the bowing upward motion of the more proximal shaft portion, its slot 45 may slip over and ultimately engage with distal edge 40 of introducer assembly 11. Though this configuration may be effective, other interactive designs are foreseeable. For example, a twist lock mechanisms may be provided, which may enable forces to be exerted remotely, to enable engagement/disengagement of elements introduced through/over an introducer element 11.

Figure 13:
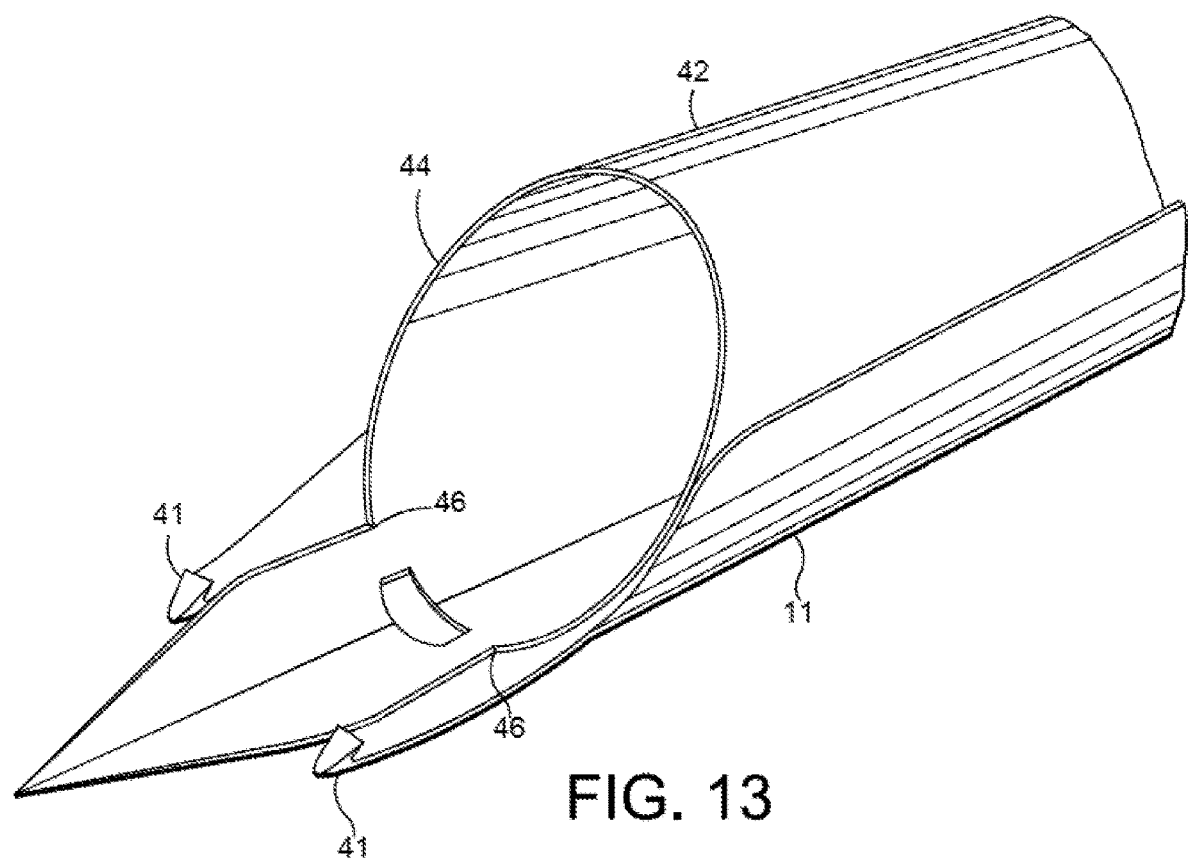
FIG. 13 is an end-on perspective view of distal segments of components of FIGS. 11 and 12 of an excisional device or device assembly of FIG. 2, according to one embodiment.

FIG. 13 is an end-on perspective view of distal segments of components of FIGS. 11 and 12 of excisional device 10, according to one embodiment. FIG. 13 shows the relationship of these distal segments with one another when, for example, a cutting loop distal end portion is being advanced distally into engagement with distal elements of the introducer assembly. Indeed, FIG. 13 shows the two components 42 and introducer assembly 11 fitted together, with component 42 in a position just proximal within introducer assembly 11, just before being advanced more distally to force engagement of points 46 with constraining elements 41. When component 42 is at a position slightly more proximal within introducer assembly 11, it may be freely rotated about its own longitudinal axis to facilitate forward advancement through tissues, along the longitudinal plane formed by introducer assembly 11, such that location of component 42 may be placed as precisely as that established by introducer assembly 11.

Figure 14:
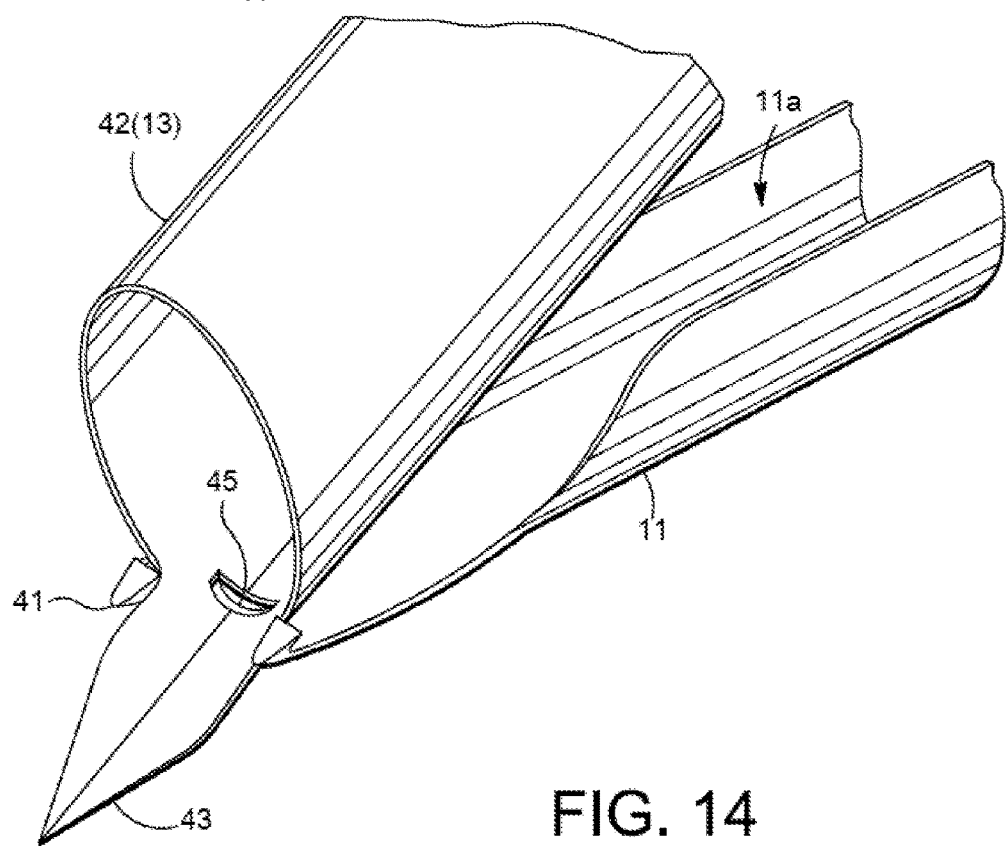
FIG. 14 is an end-on perspective view of elements of FIGS. 11, 12 and 13, according to one embodiment.

FIG. 14 is an end-on angled perspective view of elements of FIGS. 11, 12 and 13, according to one embodiment, with a distal segment of a cutting loop (such as element 13) of FIG. 12 fully engaged with distal elements of a universal introducer tray of FIG. 11 depicting the resultant perspective that would ensue when, upon further advancement of cutting loop element, its distal components are constrained in such a way as to force cutting loop element to flex into a loop shape outward from the distal longitudinal base portion of a introducer assembly 11. This configuration is also shown in FIG. 8a. In detail, FIG. 14 shows the end-on perspective view of the two components, 11 and 42 relative to one another. However, in this view, component 42 has been moved far enough distally to fully engage constraining elements/stops 41. As shown, when component 42 is further advanced its proximal portion is forced upwards out of the trough or distal scoopula portion of introducer assembly 11, which also results in distal tip 43 moving downward, simultaneously slipping slot 45 of component 42 over distal edge 40, as shown in FIG. 11, of introducer assembly 11. This engagement is significant when retracting the bowed portion of component 42 (which represents elements such as cutting assembly 13, FIG. 10) back downward into introducer assembly 11s trough 11a. This 3 point engagement in one embodiment also serves to anchor element 42, as it is forced to revolve around a target lesion by introducer assembly 11, as it itself is rotated about its own longitudinal axis by excisional device 10, whether manually by rotating handle 12, or other internal mechanisms.

Figure 15:
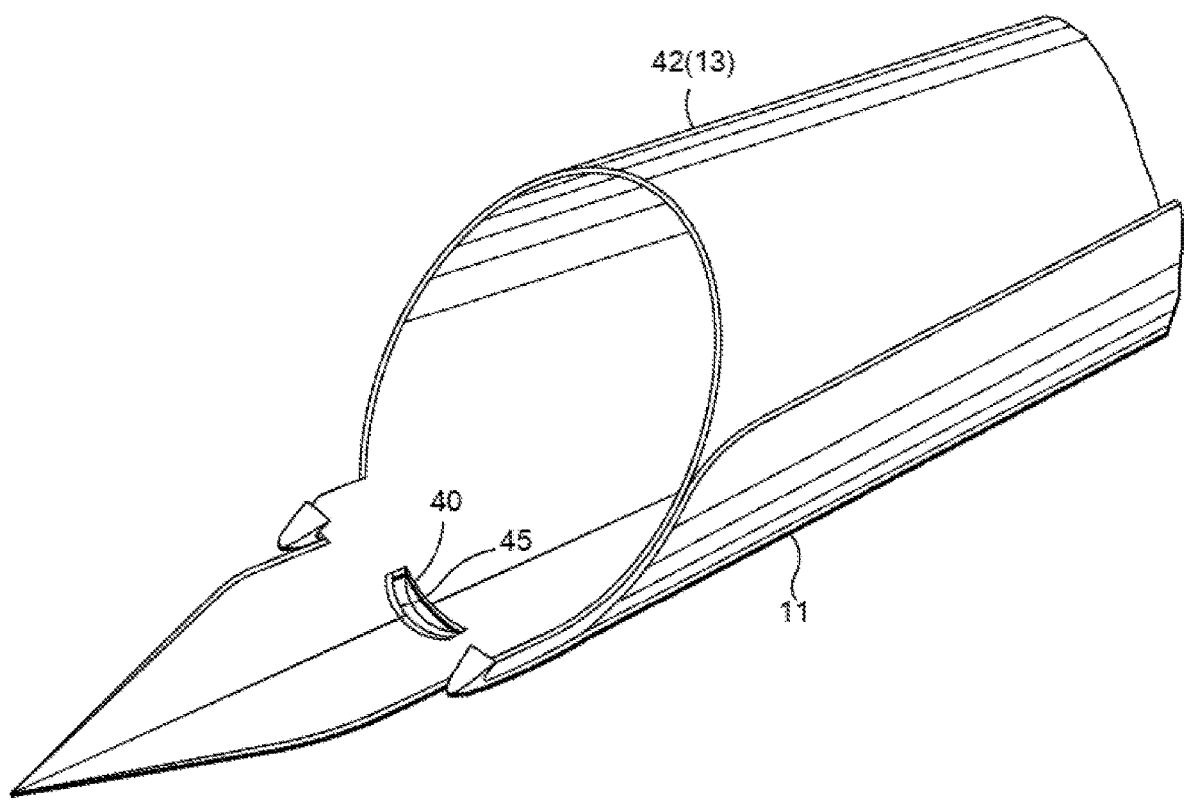
FIG. 15 is an end-on perspective view of distal elements of FIGS. 11 and 12 in fully retracted position showing a distal portion of a cutting loop lying flat within a universal introducer tray component of an excisional device of FIG. 2, according to one embodiment.

FIG. 15 shows that once component 42 is fully retracted downwards back into introducer assembly 11, slot 45 automatically disengages from forward edge 40 of introducer assembly 11, thereby permitting easy removal of component 42 from introducer assembly 11, by withdrawing it proximally and out the proximal end of introducer assembly 11. FIG. 14. Before complete retraction (de-bowing) of component 42, slot 45 will remain engaged with forward edge 40 (introducer assembly 1) so that it provides an anchor point up until the moment component 42 lies completely flat within the trough of the introducer assembly 11.

Figure 16:
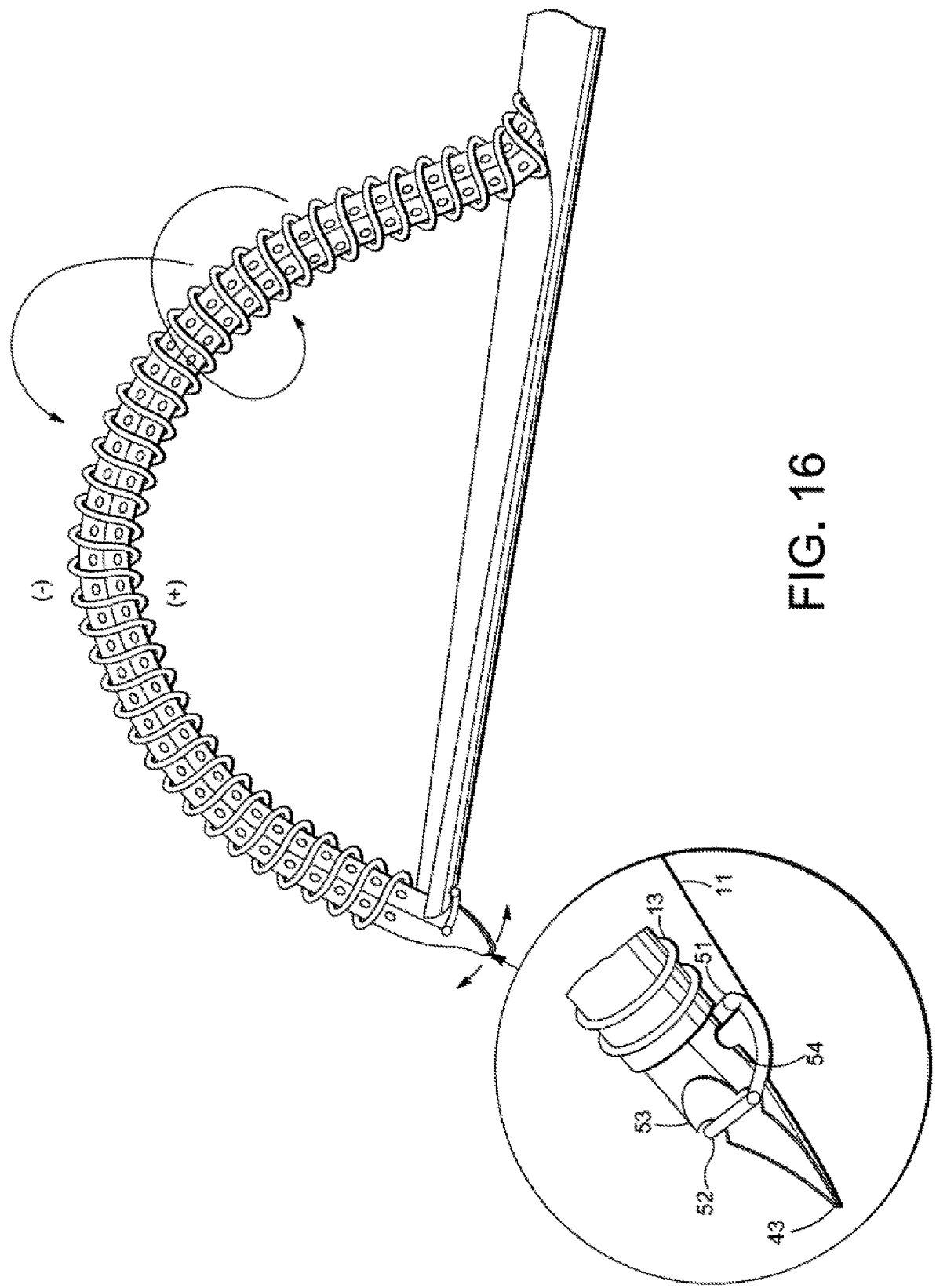
FIG. 16 is a close-up side view of details of a rotatable cutting helix assembly component in extended position, with an alternative distal tip configuration of cutting and introducer components of FIGS. 11 and 12 of an excisional device of FIG. 2, according to one embodiment.

FIG. 16 shows another distal tip configuration that enables the same functions as described in FIGS. 13, 14 and 15, according to one embodiment. In this case, the components responsible for these functions are different in both the introducer assembly 11 and the component 42 and this arrangement would serve as the distal tip of element 13, as shown. Element 51 may be configured to serve as an anchor point for retraction similar to distal edge 40, and cutouts 54 on either side of component 42 may serve in a manner that is similar to slot 45. Similarly, element 52 may serve functions similar to that of elements 41 of FIG. 14, in that it becomes a constraining engagement element, which also serves as a pivot point for downward tip movement and proximal shaft portion of component 42's movement bowing upwards out of introducer assembly 11's trough section. In order for these events to proceed securely, as component 42 is advanced distally, its distal section rides up and over element 51 so that cutouts 53 move upwards and distally to engage element 52. Upon retraction, cutout slot 54 engages element 51, just as 52 begins to disengage from cutouts 53. In this manner, an operator may introduce, perform all functions with, and then remove components so equipped to interact with introducer assembly 11 with ease, using only forces remotely proximal to these points. In this manner, without removing introducer assembly 11 from within an organ, equipment and components can be introduced and switched out for other pieces of equipment using a similar distal tip arrangement and designed for different parts of the overall procedure, taking advantage of the precise position achieved with introducer assembly 11, without disruption, trauma or the need for extra time to re-establish such a favorable position.

FIG. 17 shows a collection assembly 61, which, when introduced as a replacement for cutting, assembly 13, and driven around the same pathway as during the excisional portion of a procedure, may collect a previously-excised specimen within its confines. Indeed, an extremely thin, tough membrane, net or other configuration such as shown by assembly 61, with its hoop element 62 in place within introducer 11 may be utilized for this purpose, without the requirement for exotic materials that may have otherwise been needed to withstand the degrading forces such as extreme heat, sharp moving blades or other destructive energies associated with a separate excisional step in an overall operation. In addition, the bulk of this collection assembly 61 m need not be present until needed for removal of an excised specimen. Yet, such a configuration is simple to use, particularly if driven automatically along and around the same pathway as was made during the cutting of the lesion. For example, the assembly 62, with elements 60 and 62 may be expanded at a precise angle and longitudinal location, revolved about the same number of degrees as the original excision, and thereafter retracted. In FIG. 17, a collection assembly 61, comprising an extremely thin sock or bag 60, shown furled in FIG. 17b and expanded in FIG. 17, and in FIG. 17a, in position within introducer assembly 11 of excisional device 10 illustrates such a device and method, according to embodiments. It is apparent that similar distal elements, as may be applied to a cutting element, may be present in the collection assembly 61, such that engagement with introducer assembly 11 elements may be standardized. Also, as indicated in FIG. 17b, such a collection assembly or assembly for another purpose, such as for tissue resection, delivery of implant materials or cavity characterization, for instance, may have self-deployment features independent of the distal tip configuration of the introducer assembly 11 itself as was previously shown in FIG. 13. Indeed, FIG. 13 outlined one control mechanism at the distal tip of the introducer assembly, according to one embodiment, but it should be realized that the opening of the scoopula portion of the introducer assembly itself, as shown by the proximal end of the scoopula shape in FIG. 11, for instance, also serves as a useful constraining element, similar in function to elements 41 of FIG. 11, but at the proximal end of the scoopula opening of the introducer assembly, according to embodiments. As an illustration of this concept, in FIG. 17b, it may be seen that, according to one embodiment, a simple hairpin shaped assembly may be introduced into the introducer assembly 11. Once the tip of such an element passes beyond the proximal opening of the introducer assembly, a biased force acting upon one side of the hairpin assembly, for instance a force pushing one side or leg of the hairpin shape distally while constraining the other side would cause that leg (one side of the hairpin shape) to bow out from the distal end of the introducer assembly, which may be useful for many different self-deploying assemblies that may be controlled from the proximal end of device 10 independently of device 10, or even if the only component left in vivo would be constituted by the introducer assembly 11 and any selected assemblies introduced thereby. The actual proximal opening of the scoopula shape of the introducer assembly may be used as a constraint, in such case, to define and refine the shape of the deployment of such assemblies in vivo, according to embodiments.

Figure 18:
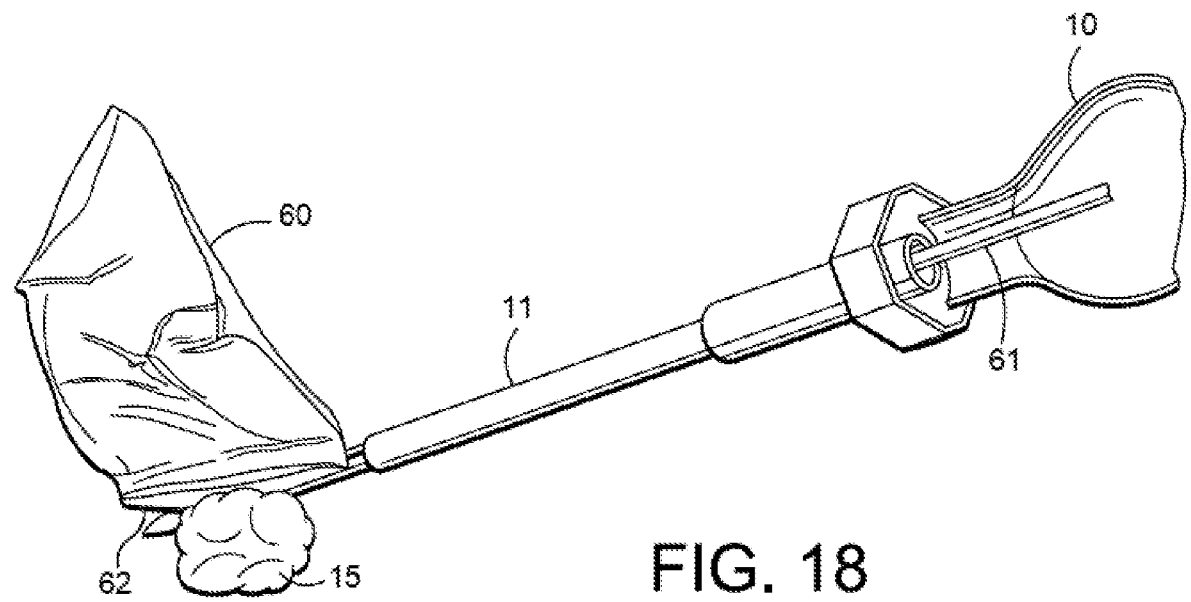
FIG. 18 is a perspective view showing a relationship between collection components as shown in FIG. 17, and as shown, a lesion targeted for removal from an organ such as a breast as in FIG. 2, according to one embodiment.

FIG. 18 is a perspective side view of a collection assembly 61 with its bag element 60 and hoop 62 shown in relationship with a roughly circular target lesion 15. According to one embodiment, the relationship of the collection assembly 61 and the bag 60 thereof within introducer assembly 11 is shown, and implicit is that similar to the interaction between the universal introducer 11 and a cutting element 13, the relationship here between introducer assembly 11 and collection assembly 61/60 enables 60 to revolve around and thus capture lesion 15 along a similar pathway as was made by the assembly of cutting assembly 13 and introducer assembly 11. Forces acting upon a proximal portion of assembly 61 may enable bowing out of hoop portion 62 of assembly 61, in order to unfurl component 60, and to open its mouth to accept target lesion 15 within capture element (which may comprise a bag, a net, etc.,) 60. It may readily be envisioned that if the hoop 62 comprises a deformable loop similar to that of a cutting assembly 13, that such deployment is possible using a number of different configurations, which are not shown. Subsequent actions of introducer assembly 11 may result in hoop 62 and capture net element 60 revolving around target lesion 15, after which, further action by axial retraction of a proximal portion of assembly 61 may then cause hoop 62 to close off and completely capture target lesion 15.

Figure 19:
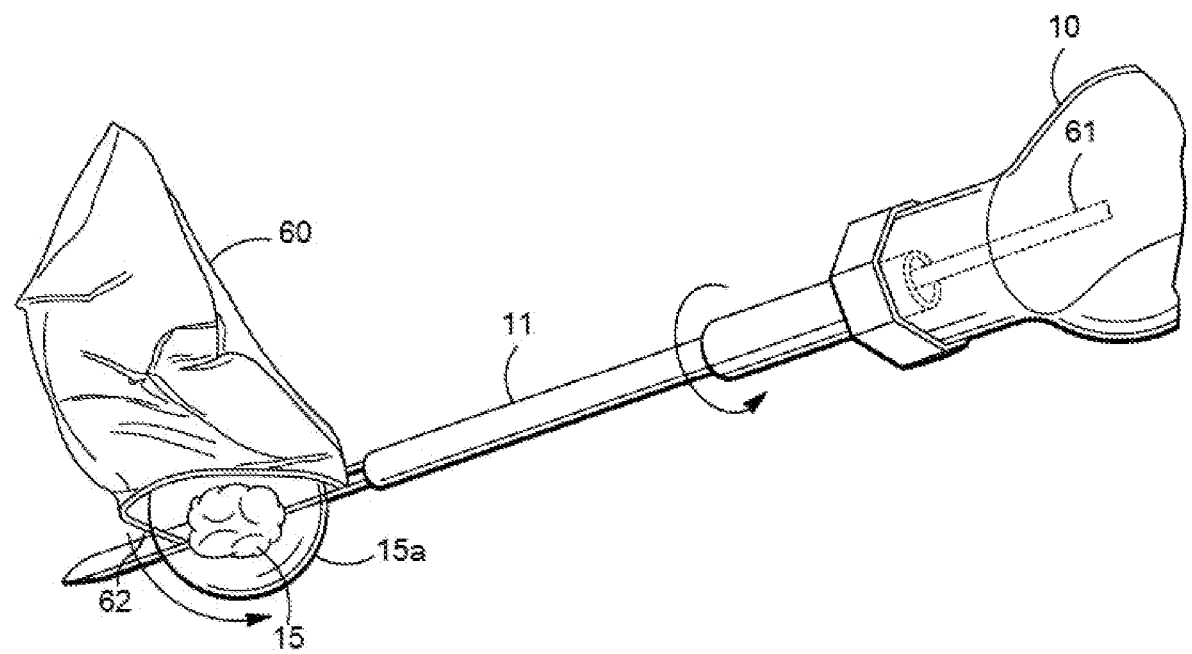
FIG. 19 is a perspective view of a collection device of FIG. 18, showing a relationship between collection components, and a lesion targeted for removal, according to one embodiment.

FIG. 19 is a perspective view of a collection device of FIG. 18, showing a relationship between collection components and a lesion targeted for removal. FIG. 19 depicts the manner in which excisional device 10 may revolve a collection component to surround and entrap a lesion previously separated from surrounding tissue for removal from an organ such as breast tissue. In detail, FIG. 19 shows these features in action steps as indicated by arrows originating from hoop 62, and a rotational arrow about the longitudinal axis of universal introducer assembly 11. Further, as shown, an axial movement of shaft portion of assembly 61 may open and close the mouth of the hoop/collection net/bag 62 to enclose and capture target lesion 15 with surrounding non-lesion tissue 15a as was resected earlier by actions of cutting loop 13 as driven by excisional device 10 together with and through introducer assembly 11.

Figure 20:
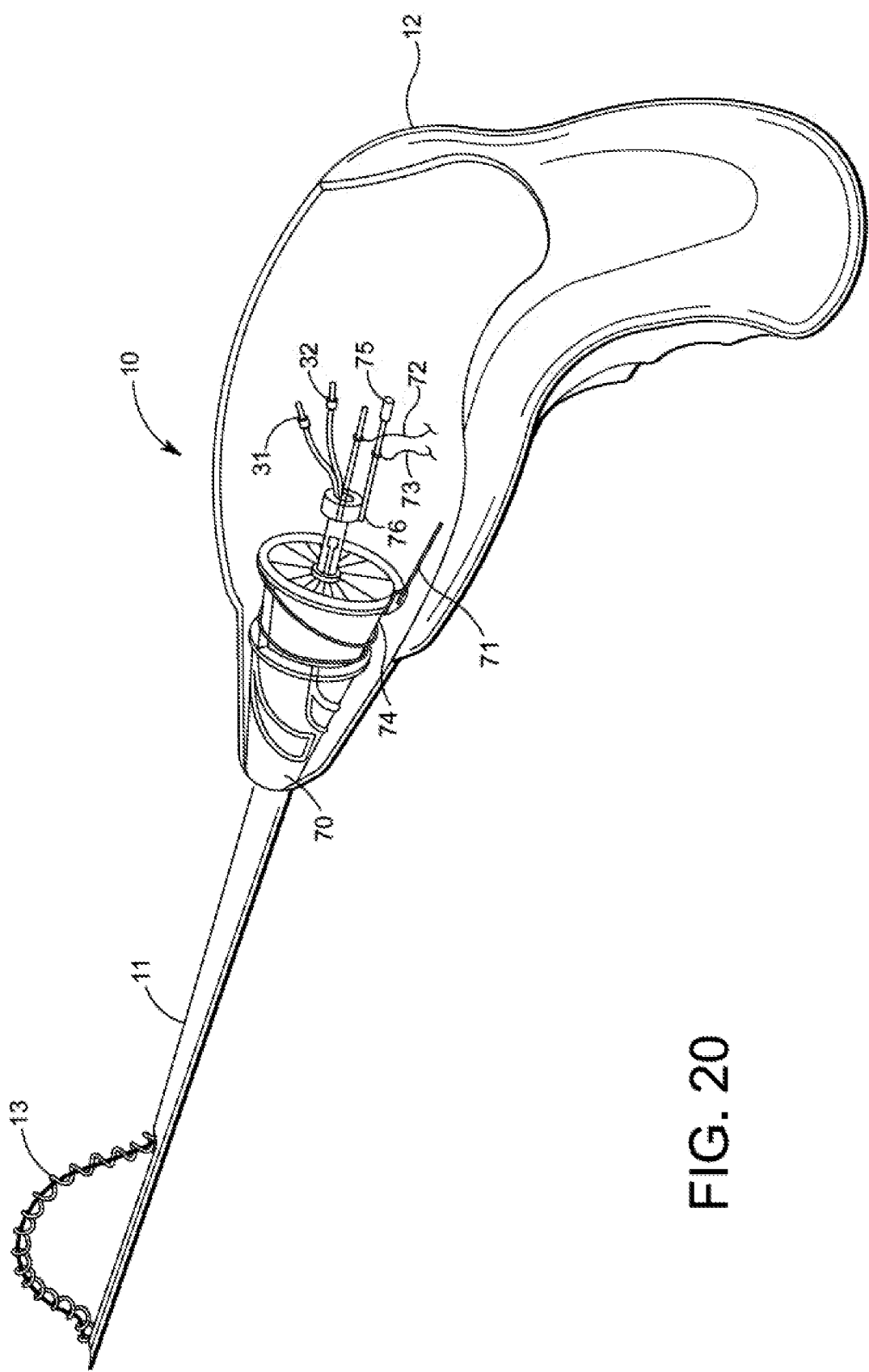
FIG. 20 is a top perspective view of components of an excisional device, according to one embodiment.

FIG. 20 is a top perspective view of components of excisional device 10, according to one embodiment. FIG. 20 also shows a partial cutaway view of the handle 12 of the excisional device 10, revealing internal mechanisms and components thereof. Such internal mechanisms and components may be configured to drive the rotation of a helical cutting element, as well as drive its expansion and revolution about a target lesion for excision. In detail, FIG. 20 shows a configuration of a driving assembly comprising a plurality of driving components within excisional device 10 as a cutaway view into the handle portion of excisional device 10, showing a simplified cutting assembly 13 already loaded into excisional device 10, through introducer assembly 11, and already bowed out as if partially around a target lesion. Some of the driving components are visible in this view, including driving connecting rod 71, which serves to drive bowing and revolution actions, through disc 74 to a proximal portion of a shaft of element 13 for bowing/retraction, and via drum 70, in the form of a barrel cam or other configuration, with its channel pathways for advancing, revolving and retracting the cutting band element around a target lesion in a cyclical fashion, according to one embodiment.

For rotating the cutting helical elements, another driving mechanism may be provided that may include propeller shaft 75, configured to drive a proximal portion of cutting assembly 13, through coupling gearbox 76. When activated, a motor drive unit may drive all these functions in proper sequence and, in the case of rotating helical components of cutting assembly 13, in a continuous fashion throughout the resecting phase and movements about the target lesion of cutting assembly 13, while handle 12 is held in a steady, stationary position. This eliminates a difficulty associated with a procedure such as this one, where an operator may normally have to attempt to hold the reference base introducer component steady, in proper relationship with and at the correct distance at all points, from an inferior or "backside" surface of a target lesion, while also twisting handle portion 12 of excisional device 10 in such a way as to properly cause resection around a target lesion with cutting assembly 13, all the while maintaining precise, uniform safety margins of non-lesion tissues surrounding a target lesion. Instead, using the excisional device 10 described and shown herein, in one embodiment, an operator is free to hold introducer assembly 11 steady and in correct position, while excisional device 10 performs the other necessary steps to consistently complete the resection phase.

The mechanisms described herein are shown in FIG. 21 enlarged for clarity, according to one embodiment. In this illustration, looking through a cutaway view of handle 12 and nose cone section 12b of excisional device 10, components of internal mechanisms needed to drive the various functions of elements introduced through excisional device 10 and its introducer assembly 11 are shown. Beginning in the nose cone section 12b, a manually rotatable barrel cam or drum 70, with its selectable channels 77 and 77a, (of note, the specific shape of these channels can be modified to attain desired actions of revolution, to create the desired curving and cutting movement of element 13, (as well as other attachments such as collecting elements and others) to guide the extension (bowing), revolution and retraction of elements such as cutting assembly 13 (shown here bowed more than it would be, given the position of channel follower component 84, so that the cutting assembly 13 can be seen projecting out of introducer component)), as channel follower component 84 is compelled, by the back and forth actions of connecting rod 71 through sliding coupling component 81 upon disk 74, overcoming return spring 80, to move along a pathway in the direction of the arrows shown, in a selected channel. Also of note is that disc 74 may be configured to be free to rotate as channel follower 84 moves along a selected channel, hence the need for sliding coupling 81 in embodiments. According to one embodiment, the follower 84 is coupled to the cutting assembly 13 and is configured to move along a path that is constrained by the channel 84 to selectively rotate and bow and retract the cutting assembly 13. Switching channels by rotating drum 70, using levers 83 and/or 83a, enables selectably smaller or larger preset degrees of revolution. If, for example, drum 70 is rotated clockwise to align channel 77a with follower 84, then a larger sweep of revolution (same degree of bowing and retraction, however) will commence automatically. Disk 74 may be configured to transmit its actions to elements such as cutting assembly 13 via proximal shaft portion 13p, which may be forced to follow the back and forth (proximal and distal) actions of disc 74, as being constrained in the axial plane by fixed ridges 85 on the proximal side of disc 74, and by button 86 on the distal side of disc 74 (but proximal shaft portion 13p is not fixed to disc 74 for revolution actions, those actions are driven by introducer assembly 11, via its fixed, in the revolution plane—but telescoping in the axial plane—attachment to inner drum component 87). According to one embodiment, therefore, the drum 70 may comprises a first channel and the follower 84 may be configured to move within the first channel 77, 77a and to cause the cutting assembly 13 to selectively rotate, bow and retract according to a first cutting profile. The drum 70 and the first channel 77, in this manner, determine a mechanically-driven first cutting profile. The drum 70, according to one embodiment may also comprise a second channel 77, 77a. The follower 84 may then be further configured to selectively move within the second channel 77, 77a and to cause the cutting assembly 13 to selectively rotate, bow and retract according to a second cutting profile that is different from the first cutting profile. The drum 70 and the second channel 77a, in this manner, determine a mechanically-driven second cutting profile.

Proximal shaft (and helical components of cutting assembly 13) portion 13p may be driven in constant (in this case in a counter-clockwise direction) rotation by gear box 76, which may be driven by a motor drive (or other mechanical means such as wound spring drive), so that helical components of cutting assembly 13 are rotated while other actions proceed as driven by the aforementioned mechanisms. Gears within gear box 76 may be driven by telescoping propeller shaft 75, with its inner sliding drive shaft component extending out and in as required to enable gearbox 76 to "float" distally and proximally as proximal shaft portion 13p is moved in those directions by disc 74 as driven by connecting rod 71. Electrical connectors 73 conduct energy to helical components of cutting assembly 13, and if bipolar configuration is desired, then connector 72 may conduct energy returning to an energy generator such as a typical RF electrosurgical unit, via an internal axial band element such as 36, FIG. 10.

Manual depression of button 82 on proximal shaft portion 13p releases constraining button 86, enabling easy removal of cutting assembly 13, back proximally and out of handle 12 via flip top 12a FIG. 4, according to one embodiment. In order to facilitate easy installation and removal of cutting elements (and others), other attachment/detachment couplings may be provided for other components. Coupler 31a permits decoupling efferent delivery tube 31 and coupler 32a functions in the same manner for afferent evacuation tube 32. Additionally, connector 72 may easily be slid off of band component 35, and finally, gearbox keeper-retainer 76 may be unsnapped permitting disengagement of gearbox 76 from driven gear 88 of proximal shaft portion 13p, in one embodiment. Similar components may be present for other elements introduced through excisional device 10 via introducer assembly 11, though not all components may be needed for various elements other than cutting assembly 13, according to embodiments.

Figure 22:
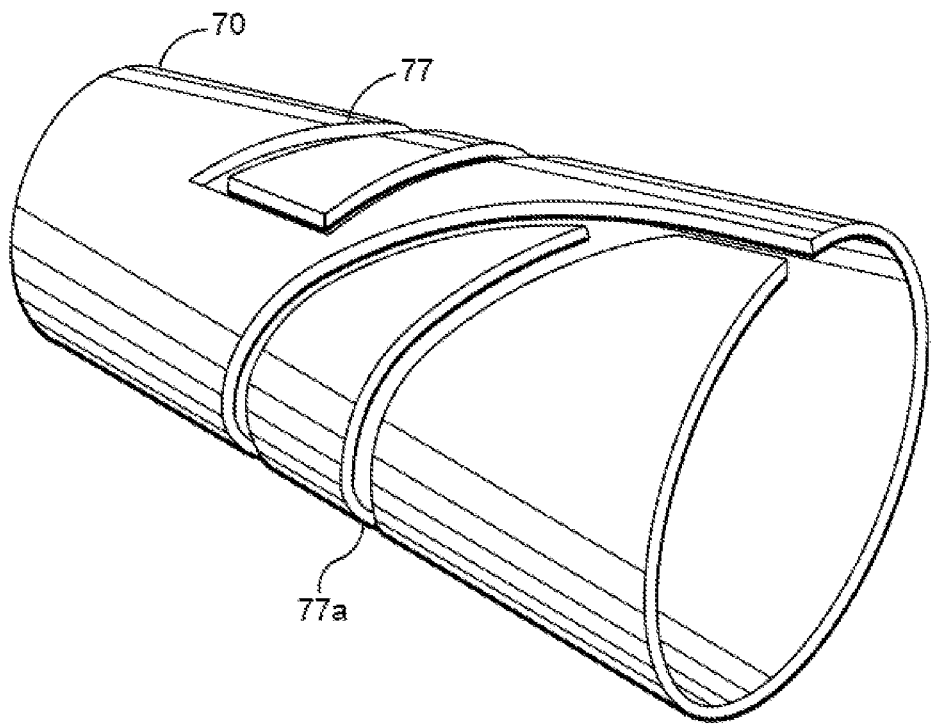
FIG. 22 is a backend, looking forward perspective view of a drum element, with integrated channeling pathway element of an excisional device of FIG. 2, according to one embodiment.

FIG. 22 shows an isolated, simple view of drum 70 with two selectable channels represented by 77 and 77a. Channel 77 may drive an approximately 90 degree revolution and channel 77a may drive a revolution sweep of 180 degrees, for example. Other revolution sweep angles may be provided as well by other channels, such as a sweep of 135 degrees, or any other angle desirable, in other configurations and embodiments.

Figure 23:
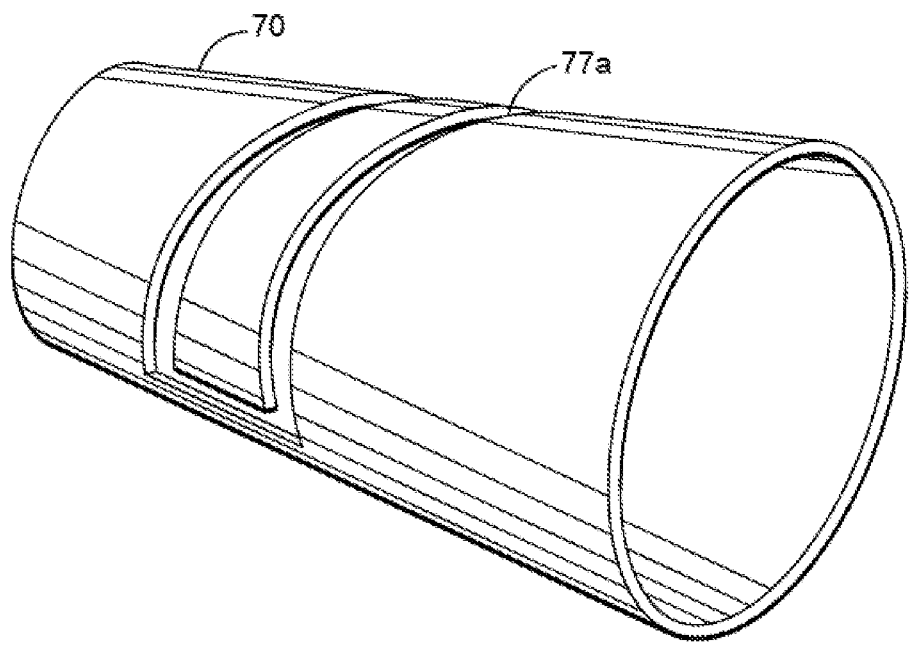
FIG. 23 is a slightly rotated but otherwise similar view of a drum element included to show another portion of a channel element to drive extension and revolution movements of cutting elements such as of FIG. 16, collection elements such as in FIG. 17, and any other components introduced into introducer tray element of FIG. 11 that need to utilize such movements, according to one embodiment.

FIG. 23 illustrates how channel 77a might appear from another rotated view of drum 77, showing that this channel may be greater than 90 degrees, such as, for example, a sweep of 180 degree's revolution. Any component introduced after cutting assembly 13 may be driven along one of these selected pathways, and using the same starting point, degree of sweep revolution and starting point of bowing and ending point of retraction, enabled by these mechanisms, may follow the same pathway. If the next following component to be substituted is a collecting component such as encapsulating/collecting assembly 60/61/62 shown in FIG. 19, then an excised specimen may be easily captured for removal from the host organ, complete, intact and insulated from contact (if component 60, FIG. 19 is of a non-porous material) with host tissue within the tract along and through which the specimen is being retracted.

Figure 24:
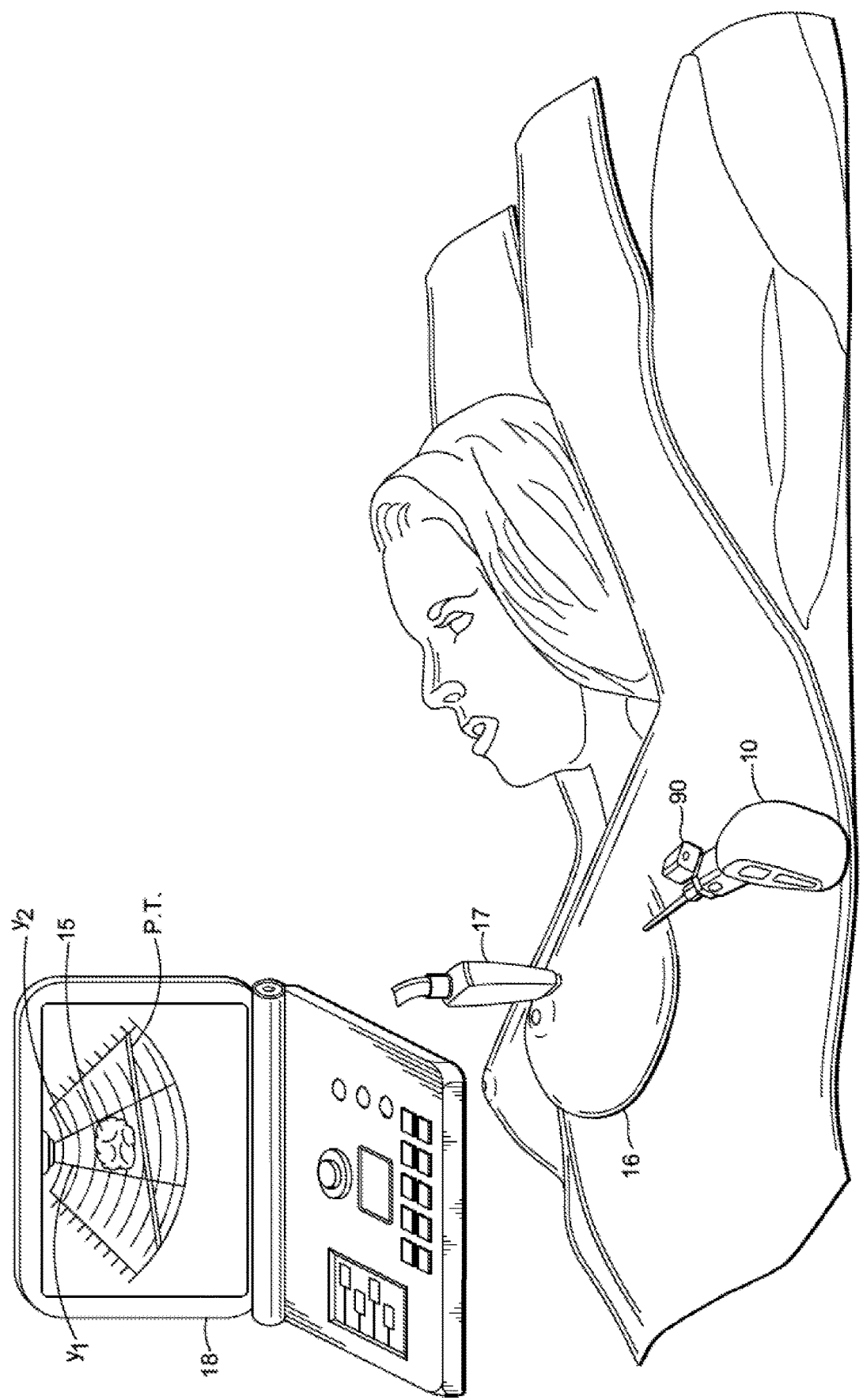
FIG. 24 depicts a side view of a patient with breast lesion 15, and an end on perspective of an excisional device 10 with attached guidance projector element 90 as well as an illustration of generated line "PT" as well as depth indicator and lesion edge designator lines Y1 and Y2, as shown on ultrasound display 18, according to one embodiment.

FIG. 24 shows an optionally-attached optical guidance projector assembly 90, used to align and target the introducer assembly 11 of excisional device 10 in three dimensions, with the desired ideal trajectory and positioning relative to target lesion 15, according to one embodiment. Such an optical guidance projector may emit narrowly focused dots, such as laser dots, in a pattern corresponding to X, Y and Z axes, according to embodiments. The dots may induce feedback signals from a sensing strip on a device such as an ultrasound transducer 17 to the ultrasound image display screen and depending on how many dots and which dots on a sensing strip receive stimulation from the light source on the guidance projector, the information may be used to realize optimal positioning of the device 10 in relation to a lesion visualized on screen. Indeed, the optical guidance projector assembly 90 may be configured to couple to an ultrasound imaging system that is configured to interpret trajectory and positioning information of the distal portion (e.g., at least the cutting assembly 13) of the excisional device obtained from the optical guidance projector assembly 90 and to display that information onto an ultrasound image display 18. Such displayed information on an ultrasound image display may be accomplished by a separate software program integrated into the ultrasound computer reading information from the sensing strip or by a separate projector system linked to the projector 90 and the transducer sensing strip and fed to the ultrasound computer, according to embodiments. In FIG. 24, "PT" designates "projected track" and is a projected image on screen, generated by the targeting system, rather than an actual ultrasound image, according to embodiments. It is projected on screen based on the position and direction of aiming of introducer assembly 11 as indicated by aiming device 90, the mechanism of which is described below. Y1 and Y2 are also generated lines indicating the lateral tilt of ultrasound transducer 17. These are also used to project distance measurements on-screen, from the bottom surface of transducer 17 to projected track (PT) line. Lines Y1 and Y2 can be narrowed and/or widened, such that they just exactly contain the edges of lesion 15.

Figure 25:
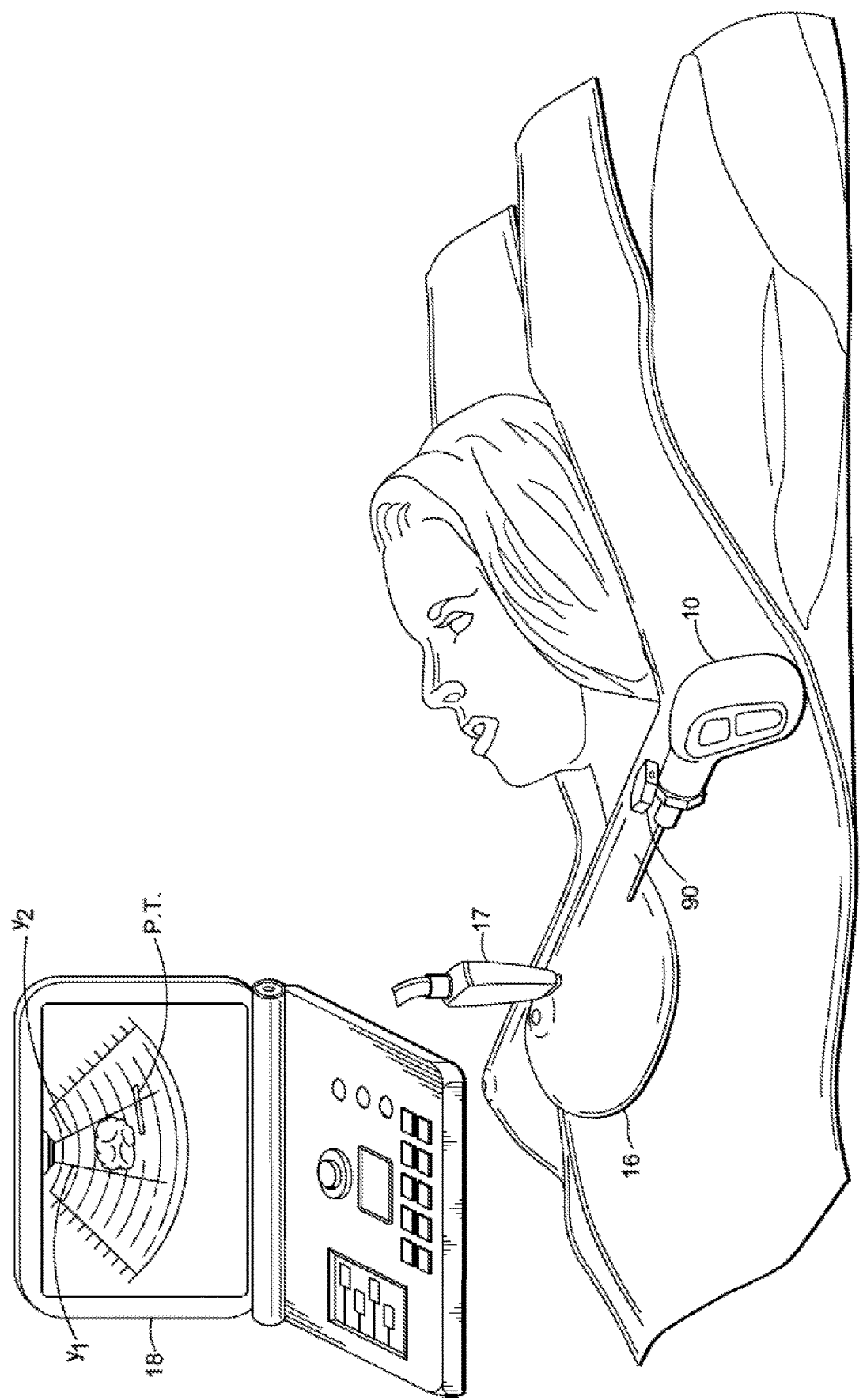
FIG. 25 shows another orientation angle of device 10 with attached guidance projector 90 aiming toward ultrasound probe 17, slightly off axis in this instance, with resultant partial line "PT" displayed on display 18, according to one embodiment.

FIG. 25 shows the same elements as FIG. 24, but in this case shows PT as it would appear if excisional device 10 were not properly aligned with the widest axis of transducer 17. In this case, only a partial "PT" line is generated, representing only the part of the projected path that would fall directly beneath transducer 17. The majority of projected line "PT" disappears from the left half of the screen, indicating that the projected path PT of introducer assembly 11 of excisional device 10 will proceed out of the imaging plane of the ultrasound probe at the point where projected path line "PT" disappears from on-screen view, as depicted on imaging display 18, in this case, representing an ultrasound image display.

Figure 26:
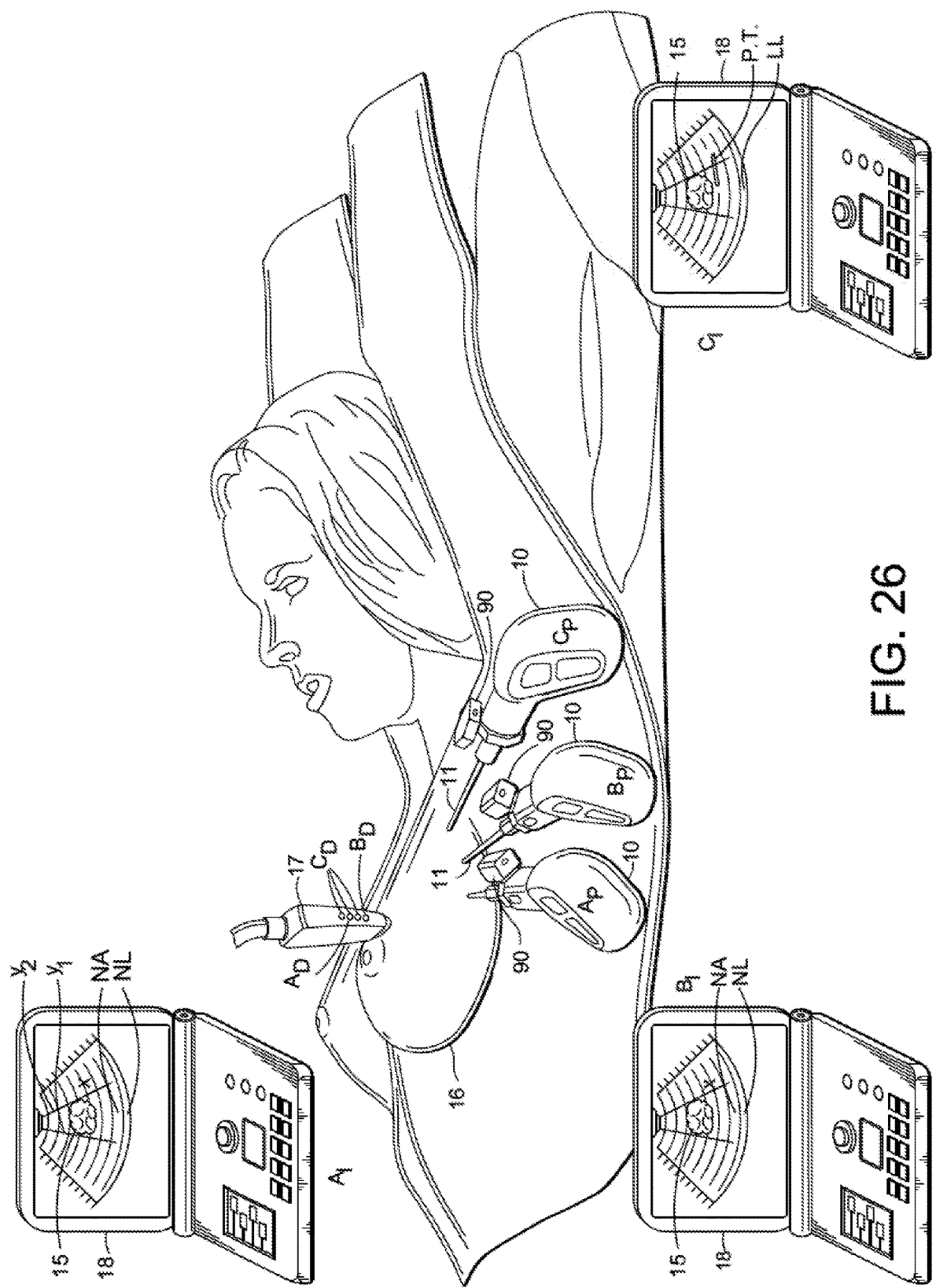
FIG. 26 shows a side view of a patient with lesion 15 in breast 16, and three different orientation examples of positions of excisional device 10 with attached guidance projector 90, and the corresponding display images labeled AI, BI and CI, showing the expected on-screen projections as a result of these various orientation positions, according to one embodiment.

Still referring mainly to targeting/positioning, FIG. 26 shows several possible positions of excisional device 10 with its introducer assembly 11 pointed in various directions, as well as various twists of handle of excisional device 10, and the information that is either available or not available depending on whether excisional device 10, along with its introducer component is properly positioned and aimed. These possible positions may correspond to initial placement on one device 10 by an operator. The upper left image as projected on display 18 is labeled "AI" and corresponds with excisional device 10 at the farthest left of the three excisional device 10's depicted, and this device is labeled "AP" (standing for position A in FIG. 26). In AI for example, on-screen indications include "NA" (indicating "no angle" indication is possible) and "NL" indicating no lateral information is available. Thus, with these two needed pieces of information missing, no line "PT" is generable, nor is depth information projected on either of generated lines Y1 and/or Y2. The reason for the missing information is that there is only one "dot" of several dots available (for example a laser dot projected by attached positioning device 90), and this dot is labeled "AD" for dot generated by attached aiming/positioning device 90, and indicating that only one dot is projected onto the near surface of ultrasound transducer 17. In order for there to be information about angle of generated line "PT", at least two position device 90 generated dots are required to fall on the near face of transducer 17. Though excisional device 10 is pointing at the near face of transducer 17, its introducer assembly 11 is not properly lined up with the wide axis of transducer 17. In addition to being out of plane with transducer 17, the twist of handle of excisional device 10 prevents a second dot of a pair of angle generating dots from appearing. Though one of the lateral dots might be expected to appear, this is ignored for now, as is described in further detail below. Lower left display 18 is labeled "BI" and corresponds to position "B" as depicted by the middle of the three instruments 10 shown in FIG. 26, labeled "BP". In this case, introducer assembly 11 is properly aligned with transducer 17 and thus, one might expect a line "PT" to be generated on-screen, however, again handle of excisional device 10 is twisted preventing a second, angle generating dot from appearing on the near face of transducer 17. Only one dot, labeled "BD" appears on near face of transducer 17. Thus, no angle information is generated and again, "NA" appears on screen. In addition, no lateral dots appear on transducer 17, and thus again, "NL" appears on screen to indicate that lateral information is also unavailable. In the lower right display 18 labeled "CI", two angle dots (upper and lower dots labeled "CD") appear. Thus, though a generated line "PT" is partially visible, since only one lateral dot (a right lateral dot in this case) appears (the middle of the three dots labeled "CD") on display 18 as depicted by "CI" the lateral position of this dot on the near face of ultrasound transducer 17 (mechanism to be described later) dictates the length of projected line "PT" and the letters "LL" appear on screen to indicate to operator of excisional device 10, that its introducer is pointed "left lateral" to the widest axis of transducer 17. This is possible because a left lateral dot generated by aiming/positioning projector 90 is missing from the near surface of the sensing strip on ultrasound transducer 17. Were the operator of excisional device 10 to change the lateral direction of introducer assembly 11 to a more rightward direction, the letters "LL" may disappear and generated line "PT" may continue full-length across display 18 as would then be depicted in "CI". Not illustrated, but considered to be part of the device, in various embodiments, is a simple physical frame connecting the excisional device 10 with the ultrasound transducer 17. This frame, which could be constructed of light materials, would allow for the relative or course tuning positioning of the two major components, the excisional device 10 and the ultrasound transducer 17, without introducing additional variables during the fine positioning of the excisional device by keeping the transducer in a fixed position relative to the breast 16 and lesion 15. With this constant, fixed ultrasound transducer position, off axis placement of the excisional device 10 could be dialed out relatively easily by the operator.

Figure 27:
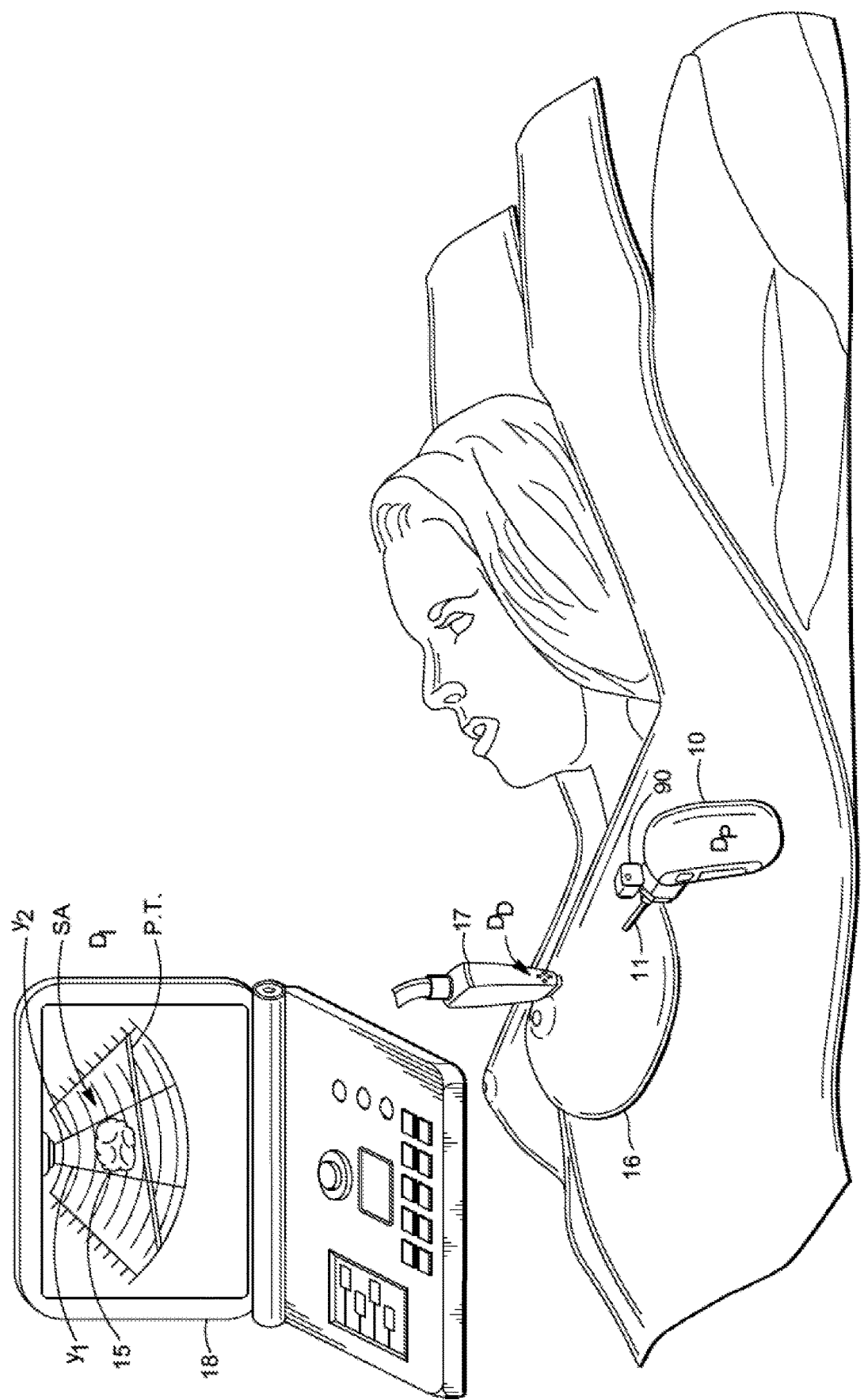
FIG. 27 illustrates correct orientation and positioning of excisional device 10, with its guidance projector 90 attached, according to one embodiment.

FIG. 27 is a side view of a patient with lesion 15, and illustrates a full correct orientation and positioning of excisional device 10, with its guidance projector 90 attached, according to one embodiment. Correct positioning dots are shown on transducer 17 labeled "DD". Additional display arc SA also appears based on positioning of introducer assembly 11 under lesion 15.

In FIG. 27, in contrast to the three positions as depicted in FIG. 26, the position of excisional device 10 as depicted here and labeled "DP" is properly aimed and aligned with the near face of ultrasound probe 17, as indicated by the appearance of four dots as projected from aiming/positioning element 90, on the sensing strip on the near face of ultrasound transducer 17. The fact that these four dots appear results in sufficient information to generate full-length on-screen line "PT" as well as depth information associated with generated lines Y1 and Y2, and in addition, an arc labeled "SA", standing for "sweep arc", which projects a full sweep arc that may be followed by introduced cutting assembly 13. This arc appears without any additional markings as will be shown in subsequent figures.

Figure 28:
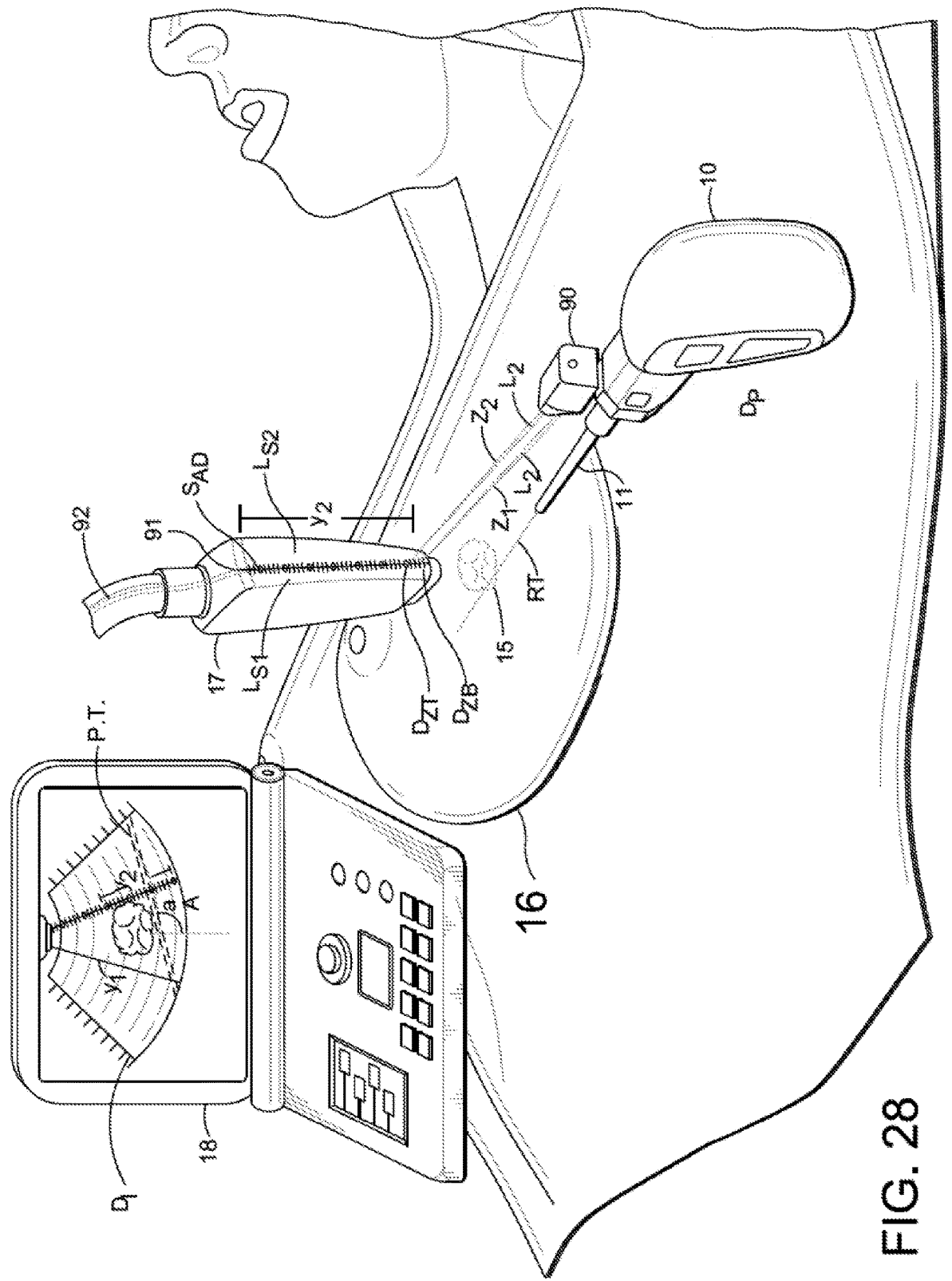
FIG. 28 shows a more close-up side view of a patient with breast 16 and lesion 15, and an excisional device 10 with its attached guidance projector 90, according to one embodiment.

FIG. 28 shows a more close-up side view of a patient with breast 16 lesion 15, and excisional device 10 with its attached guidance projector 90, according to one embodiment. Also shown are projected (dashed) beams Z1, Z2, L1 and L2, as well as sensor strip 91 with its various components and its attachment cable 92 as plugged into ultrasound machine 18, its display showing resulting on-screen generated lines. The sensor strip 91 may comprise one or more sensors (e.g., optical sensing elements) whose electrical output may be fed back to and interpreted by the imaging system 18 (in this implementation, an ultrasound imaging system). The interpreted output of the sensors may then be displayed on a display of the imaging system as visual indicators of projected path, position and orientation. The operator may thereafter view the displayed visual indicators and adjust the position and/or orientation of the device until the distal, working end thereof is in a desired position and orientation. The visual indicators may take the form of letters, numbers, lines and/or other forms of perceptible feedback (e.g., sound), to enable the operator to more accurately position the distal end of the device within the tissue.

According to one embodiment, real trajectory may be indicated by dashed line labeled "RT" passing under lesion 15 in breast 16, along with the way "RT" may appear labeled as "PT" on ultrasound display 18. Still referring in general to aiming/positioning components of a system to project proper positioning, aiming, depth and sweep among other information, FIG. 28 shows sensor strip component 91 of aiming/positioning system 90/91, as plugged into image display 18 via wire 92, according to one embodiment. Sensor strip 91 comprises elements "LS1" and "LS2", which sense lateral dots (horizontally placed emanating from projector 90) generated by aiming/positioning projector 90. Element "SAD" indicates a center strip sensor that, detects angle and depth (vertically placed beams emanating from projector 90) dots generated by projector 90. In this case, the real trajectory labeled "RT", of introducer assembly 11 as depicted by the dashed line is imaginary, not displayed, except for illustrative purposes, in FIG. 28. Angle "A" is generated by computing the relative distance information (the difference in distance) from lines "Z1" and "Z2", based on the sensed distance differential between these pairs of lines, "Z1" and "Z2". This information is generated by projector 90, based on reflections of light such as laser light beams, from the near surface of introducer 17. Depth of line "PT" on-screen is based on sensing dots "DZT" (corresponding to beam "Z1") and "DZB" (corresponding to beam "Z2"), which labels stand for z-beam dot top and z-beam dot bottom. With these pieces of information, (along with lateral information, not depicted here purely for simplicity) axis alignment, depth and position can be projected on-screen, in real time and with a high degree of accuracy.

Figure 29:
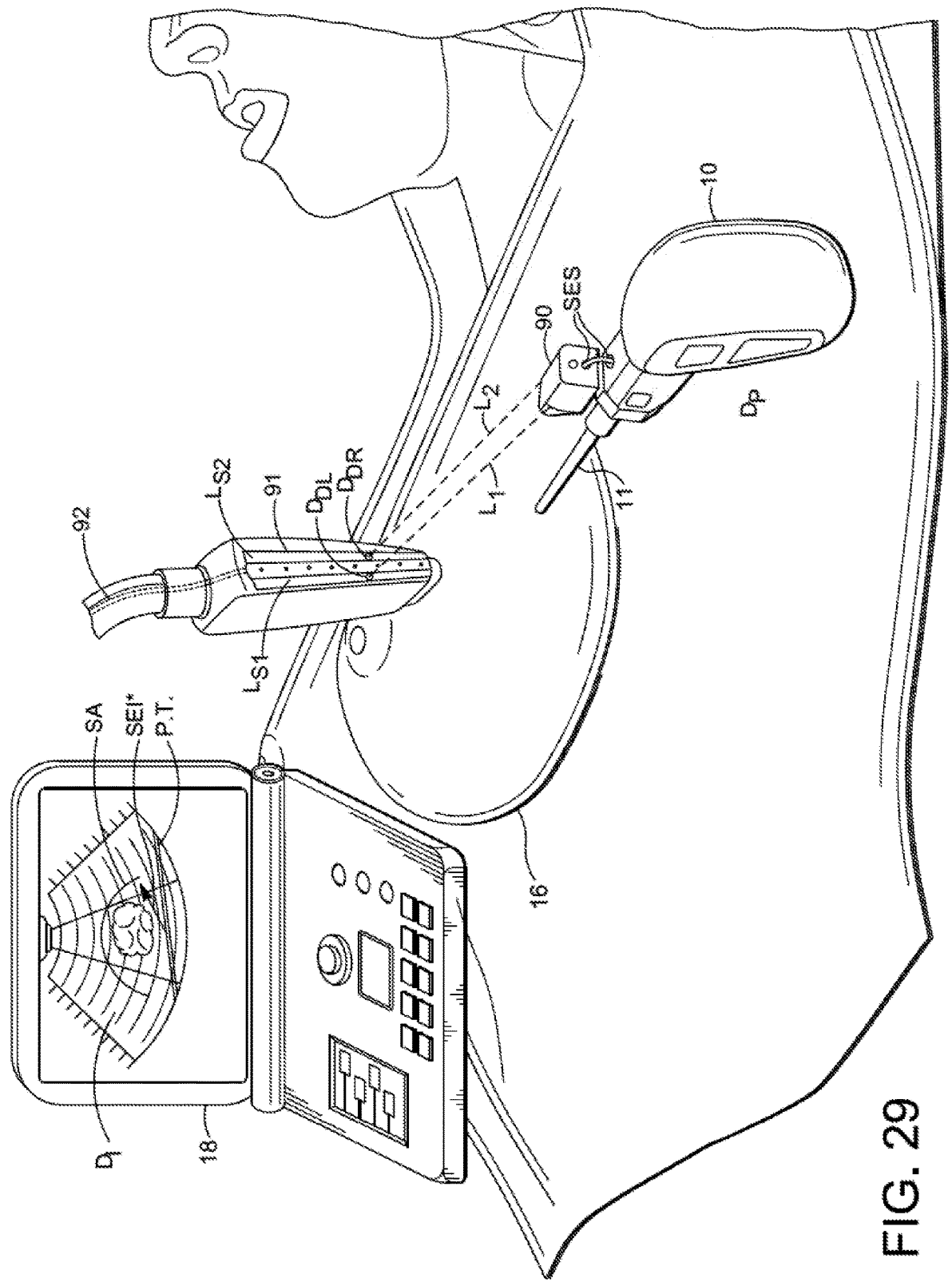
FIG. 29 is another close-up side view of a patient with breast 16 and lesion 15, with a partial end-on view of excisional device 10 with attached guidance projector 90 generating lateral guidance beams L1 and L2 as well as lateral dots DDL and DDR on sensor strip areas LS1 and LS2 along with ultrasound display 18 showing generated line "PT", according to one embodiment.

FIG. 29 is another close-up side view of a patient with breast 16 lesion 15, a partial end-on view of excisional device 10 with attached guidance projector 90 generating lateral guidance beams L1 and L2 as well as lateral dots DDL and DDR on sensor strip areas LS1 and LS2, along with ultrasound display 18 showing generated line "PT", according to one embodiment. Also shown on ultrasound display 18 labeled "DI" corresponding to position "DP" of excisional device 10 with its introducer assembly 11, are additional progress-indicating arrow "SEI" and projected cutting-arc indicator "SA". Such a position may be seen in FIG. 6b for reference, correlating on screen images with progress indicating arrow "SEI". FIG. 29 shows only the lateral beams, labeled "L1" (left lateral beam) and "L2" (right lateral beam) projected by projector 90. These show up on sensing strip 91 sections "LS1" and "LS2" as "DDL" and "DDR" indicating left lateral and right lateral dots as landing points for beams "L1" and "L2" respectively. Again, proper position and aiming of excisional device 10 at the position/direction labeled "DP" is indicated by the completeness of on-screen information and depiction. Note that arc "SA" again appears and in addition once introducer assembly 11 is perfectly positioned from an axial/longitudinal perspective, i.e., the open segment from which cutting assembly 13 projects, is directly underneath lesion 15, such that the arc-sweep path cut by element 13 will be entirely outside of borders of lesion 15, then new arrow-line "SEI" appears on screen, the letters "SEI" standing for "sweep excursion indicator". This line may only remain on-screen as long as the correct axial depth/longitudinal factors are positioned and maintained (real time). This sweep excursion indicator's arrow tip sweeps along generated arc "SA" as cutting assembly 13 is swept around lesion 15, with its relative progress along this arc pathway, indicated by the counterclockwise sweep-movement of this arrow, as generated by a sensing element connected to projector 90 projector 90 by connector labeled "SES" standing for "sweep excursion sensor" and which is a simple sensor that detects progress/position of drum component 70, FIG. 23, according to one embodiment. "SEI" has an asterisk linking it to label "CAP", which stands for "correct axial position" of introducer assembly 11 and thus also cutting assembly 13 relative to lesion 15 as depicted in the right half of FIG. 29, corresponding to FIG. 6.

The introducer assembly 11, the device 10 and the structures shown and described relative to FIGS. 17, 18 and 19 may be used to good effect together. According to one embodiment, after the lesion or tissue of interest has been excised, the cutting assembly 13 may be removed and replaced with collection assembly 60/61/62, engaging within excisional device 10 in a manner that is similar to the manner in which cutting assembly 13 is described above as engaging with excisional device 10. The correct position of introducer assembly 11 may then be verified, after which the excisional device 10 may be activated to initiate and complete a collection cycle, using the same settings as were used for the prior excisional stage. The ultrasound display 18 may then be viewed to monitor progress. On-screen cues, if used, may also be monitored, such as generated angle line "PT", arc "SA" and progressive indicator arrow "SE", through a collection cycle. When a collection cycle is verified to be complete, the collection shaft 61 may be slightly withdrawn to fully disengage the distal end from introducer assembly 11, and the distal end of the introducer assembly 11 may be slightly tipped downward. The assembly comprising the excisional device 10 and the introducer assembly 11 may then be withdrawn in this orientation. Thereafter and only to the extent necessary, the skin incision may be slightly widened to withdraw the collection assembly complete with fully enclosed specimen (e.g., lesion) 15 and surrounding (e.g., margin) tissue 15a, as is shown in FIG. 19. If the introducer guide wire and/or insertion cannula were used, these may be left in place for re-introduction of excisional device 10 and introducer assembly 1 (see also FIGS. 9 and 9a) and/or other devices such as an implant delivery excisional device 100 (FIG. 30, described below), intra-tissue ultrasound devices, other RF-based or other devices having other modes of action (e.g., cryogenic), either alone or via introducer assembly 11 in conjunction with excisional device 10, according to embodiments. The introduction of an ultrasound device, for example, may be advantageous; in that the short distance between the probe and the internals structures of interest and close coupling thereto may yield significantly more detailed resolution than would be otherwise achieved using an external ultrasound probe. Indeed, the short distance and close coupling enables the use of higher frequencies that are able to resolve smaller structures than is possible with the relatively lower frequencies used in external ultrasound.

Precise placement of the excisional device 10 and of other components may be achieved, together with continual monitoring of the progress of the procedure and of the stability of the device, according to one embodiment. Indeed, a method for using introducer assembly 11, excisional device 10 with ultrasound guidance, guidance projector 90 and reflective guidance sensor strip 91, according to one embodiment and with reference to FIGS. 26-29, may comprise affixing sensor strip 91 to ultrasound probe 17 vertically on its side edge and plugging wire 92 into ultrasound machine 18. The projector 90 laser guide beams may then be activated and aimed at sensor strip 91, so that all laser dots appear on sensor strip 91. The ultrasound display 18 may then be viewed and the generated angle line "PT" (on display 18) and line "PT" may be aligned to the desired path by aiming introducer assembly 11/excisional device 10 up or downwards. When arc "SA" appears on the screen, its presence may be maintained by following on-screen instructions to swing an introducer component left or right as directed. If no instructions appear and arc "SA" remains full and on screen, then introducer assembly 11, excisional device 10 is correctly aligned in plane with the imaging plane of the ultrasound transducer. The aligned introducer assembly 11 may continue to be advanced until indicator arrow "SEI" appears on screen. When "SEI" appears, the introducer trough is correctly positioned directly under the center of the ultrasound transducer 17. The cutting element (or other attachment such as collection assembly 61) may then be introduced and the excisional device 10 may then be activated for a mode of operation that is appropriate for its attachment (e.g., the structure and functionality of the distal working end of the device) and its progress followed by observing movement of "SEI" along a preset arc on screen.

Figure 30A:
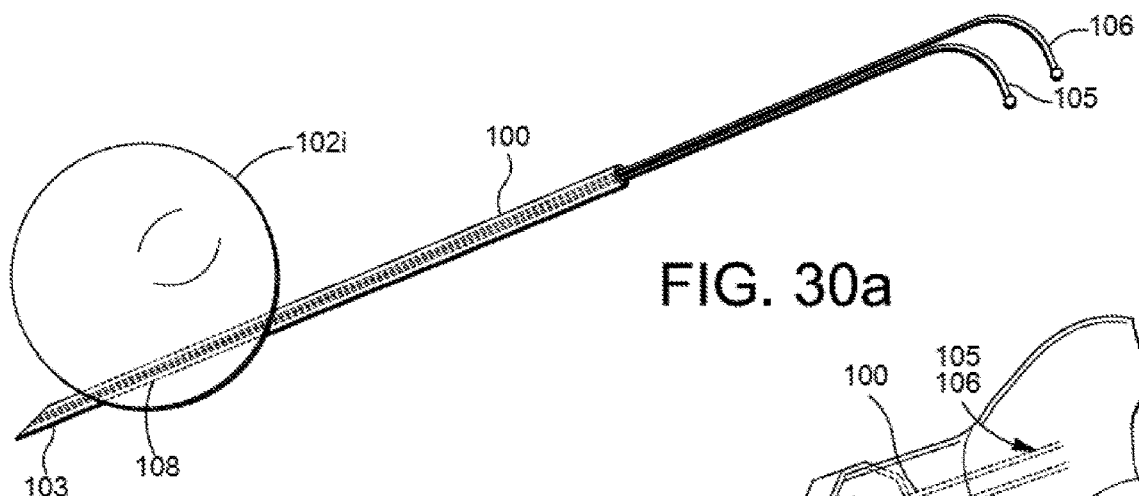
FIGS. 30a, 30b, 30c, 30d, and 30e are various perspective views of implanting attachment membranes deploying from an excisional device 10 or its components, according to embodiments.
Figure 30B:
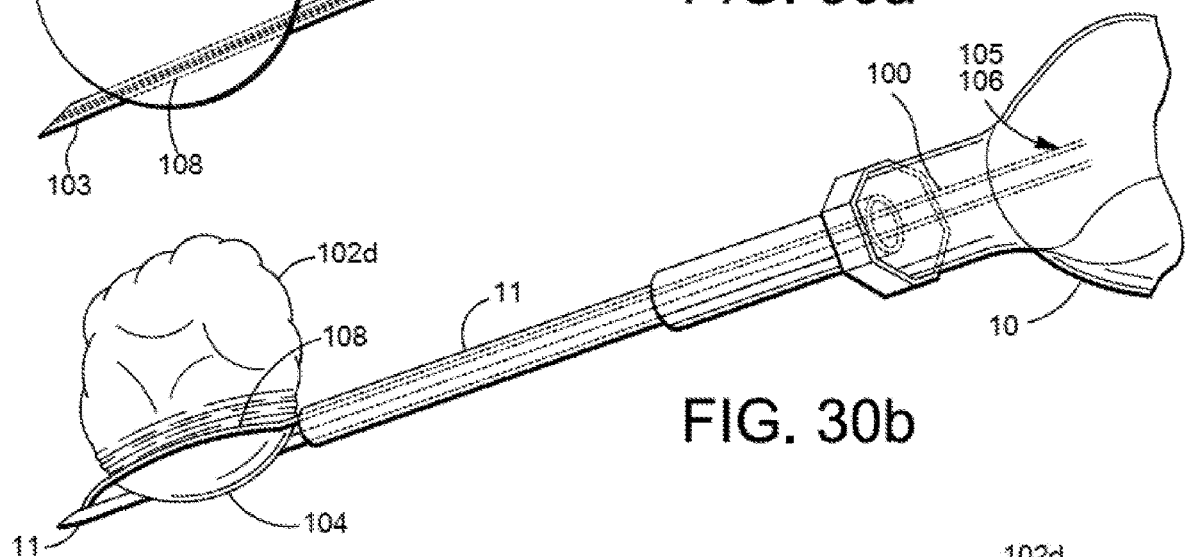

FIGS. 30*a* through 30*e* are illustrations of another attachment component 100 for delivering implantable materials (in this case a double component implantable material labeled 104), according to one embodiment Membrane element 102 is shown in various side view positions labeled FIGS. 30*a* through 30*e*, showing various stages of use. Membrane 102 labeling is modified to indicate various states of inflated ("i"), deflated ("d") or furled ("f") about shaft of component 100. FIG. 30*b* shows the relationship of introduced attachment membrane 102 as used in conjunction with excisional device 10 and via introducer assembly 11. Also shown are delivery tubes 105 and 106. Referring now to an introducer 100 to excisional device 10 via introducer assembly 11, the various figures illustrate an implant delivery system 100 with its components in various stages of use, labeled in order. FIGS. 30*a* through 30*e*. FIG. 30*a* shows shaft of excisional device 10, containing injection tubes 105 and 106 within and these are connected to encircling membrane 102*i*, the lower case "i" indicating the membrane, which may be single or double wall, is inflated/stretched by injection using inflation devices attached to tubes 105 and/or 106 as illustrated. In FIG. 30*a*, loop/seal 108 is shown in fully sealed position; that is, fully retracted. In this position, injection via tube(s) 105 and/or 106 will stretch the single/double wall membrane into a generally rounded shape, as within a body cavity, and may be stretched to touch the walls all around, or even stretching the walls slightly or as desired.

Components such as liquids, gasses, solids and/or semi-solids including marking elements may be injected, and/or pre-loaded into membrane 102. If injected material happens to be a two component substance that firms hardens or takes a "set" in the shape of its membrane container, once "set", cured or otherwise achieves a desired state of stability, excisional device 10 may be activated to remove by expansion and revolution and/or rotation (if desired to "furl" membrane on loop/seal 108) of loop/seal 108 in a clockwise or counterclockwise direction (CCW revolution is shown) membrane element 102, which is now designated 102*d* to indicate it is no longer under inflation/stretch tension, as now shown in FIG. 30*b*.

Figure 30C:
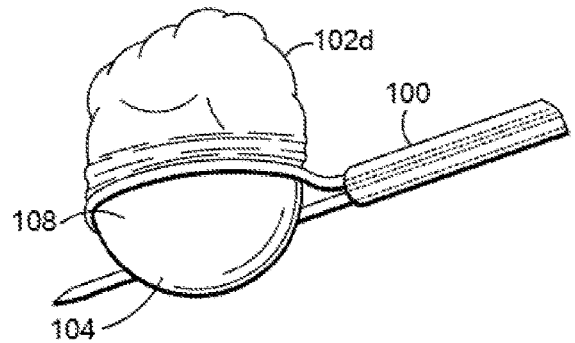
Figure 30D:
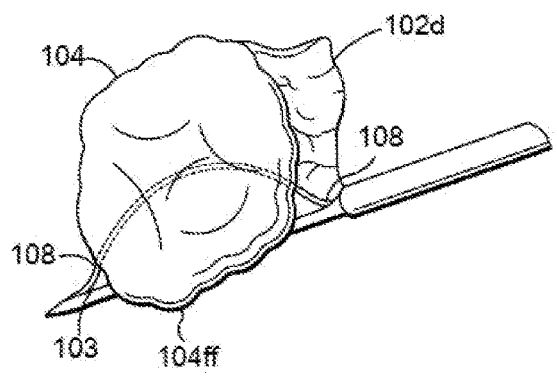
Figure 30E:
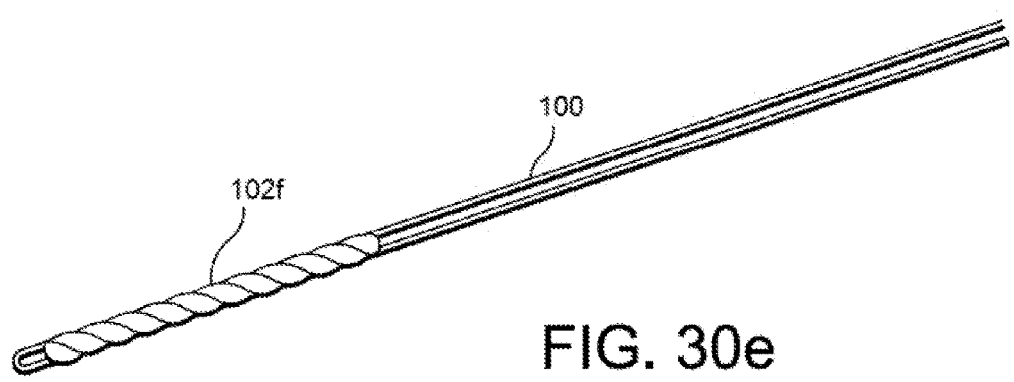

Additionally, FIG. 30*c* shows that substance 104 can now begin to be seen as membrane 102*d* is removed from its surface. An alternative to "furling" as a way to peel back the membrane from the surface of the injectable, now firmed up or "hardened" implant, may be to release either the leading or trailing edge (½ of mouth, or comprising one "lip" of a bag closure edge) from its attachment, either from the bow/hoop or the other lip from the shaft/base of the introducer element 100. This release may be done via a "zipper" like attachment of any number of ways and methods, or it may be a sharp cut along either of the attachment edges. In either case, it may then be an easy task, not disruptive to the substance implanted/injected, to remove the membrane/bag element 102 together with its introducer 100, completing the delivery/implant procedure. FIG. 30*b* also shows introducer 100 as used within introducer assembly 11 of excisional device 10. However, introducer 100 may be used freehand, without introducing it into position via introducer assembly 11, excisional device 10, in other embodiments. FIG. 30*c* shows further exposure of stable substance 104 as loop/seal 108 is further revolved in a counterclockwise direction. As shown in FIG. 30*c*, assembly (attachment) 100 may be used by itself without excisional device 10. However, when used with excisional device 10, introducer 100's motions can be precisely and/or automatically controlled by excisional device 10. FIG. 30*d* shows substance 104 in a stable shape and state which may conform to the actual cavity shape, however shaped, as intimated by its shape in this illustration, with membrane 102*d* nearly fully removed from its surface, with loop/seal 108 ends just visible near at proximal and distal lower edges of implant substance 104. Tip of introducer 100, labeled 103 is also designated. FIG. 30*e* shows the appearance of membrane 102*f*, the lower case letter "f" indicating it is now in fully furled position about the shaft of excisional device 10, and now in low profile, ready for removal from the body/cavity (not shown).

Figure 31:
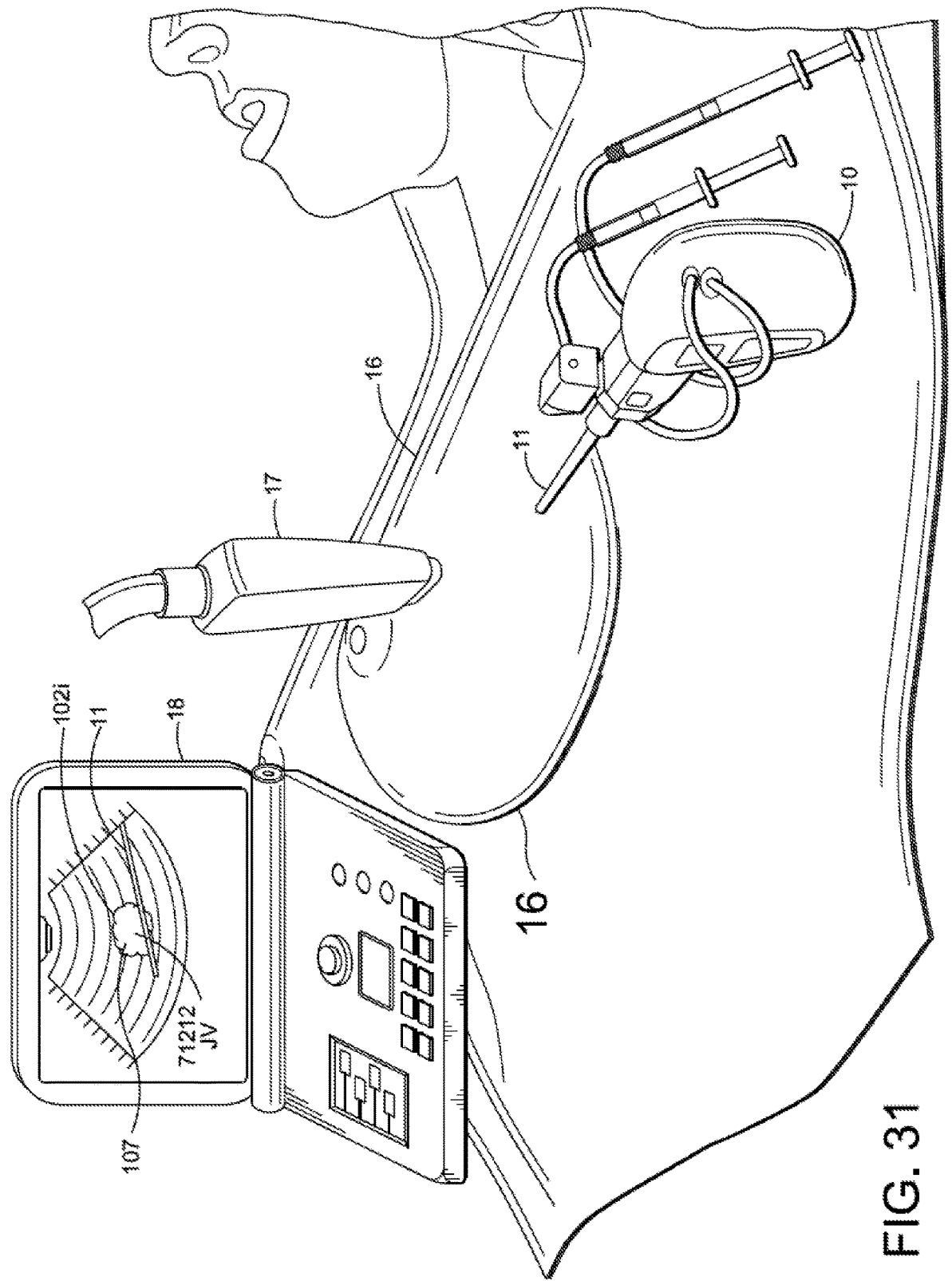
FIG. 31 is a close-up side view of a patient with breast 16, with implanting attachment membrane 102 placed in breast 16 using device 10 via introducer assembly 11, according to one embodiment.
Figure 31A:
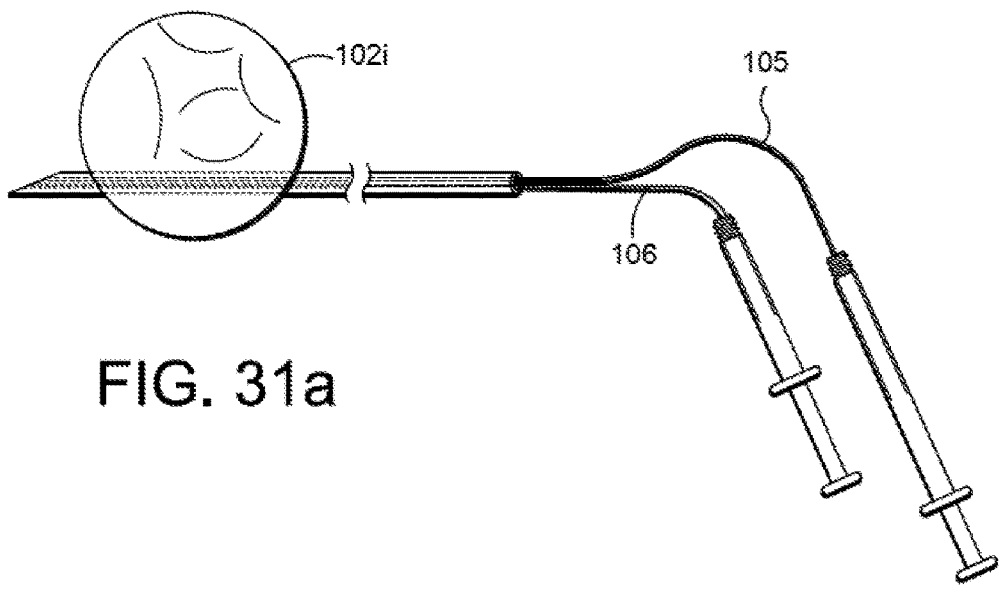
FIGS. 31a, 31b, 31c, 31d, 31e and 31f show various views of formation of an implant using device 10 or its components, according to embodiments.
Figure 31B:
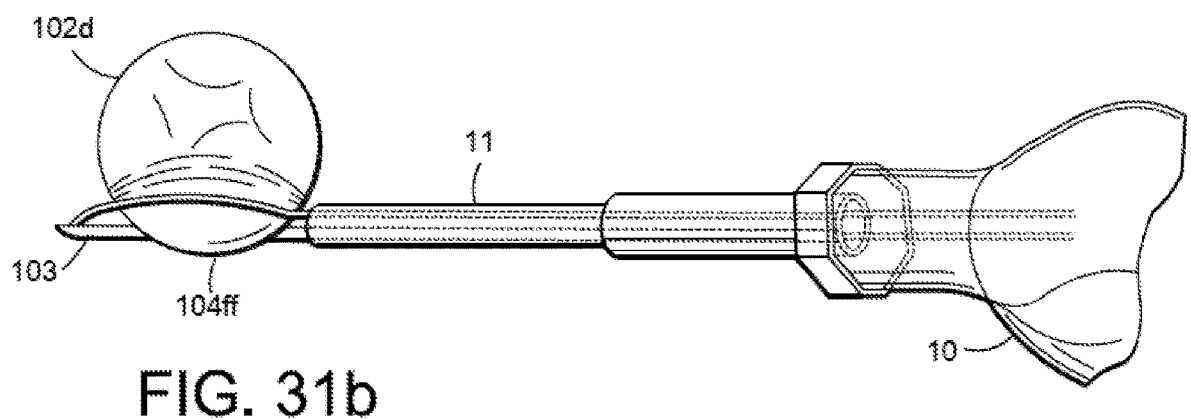
Figure 31C:
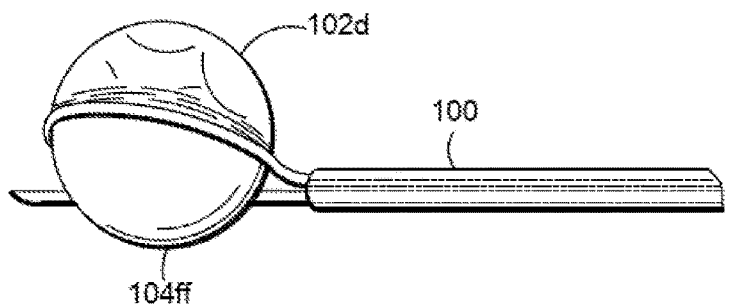
Figure 31D:
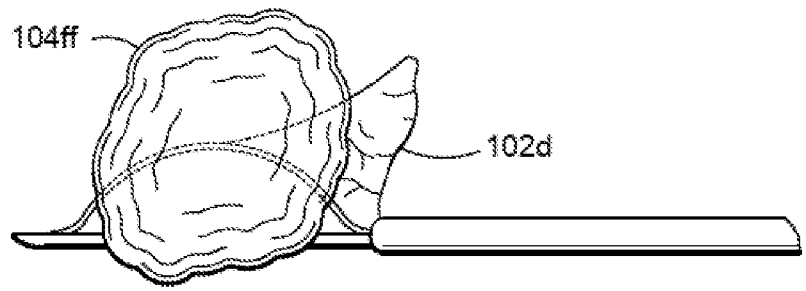
Figure 31E:

FIG. 31 is another close-up side view of a patient with breast 16, with implanting attachment membrane 102 placed in breast 16 using excisional device 10 via introducer assembly 11, according to one embodiment. The on-screen display 18 shows an image of 102*i* along with implantable labeling component 107 (shown as a random "71212JV" designation that may correspond to an operator/date/time stamp, for instance). Also shown are the various stages of use of implanting attachment membrane 102 to deliver, in this case, two-component implantable element 104, as shown in FIG. 31*a* as well as an additional bottom up view of the appearance of the implant-exposing sweep action of loop element 108 of implanting attachment membrane 102. FIGS. 31a through 31f show details of the same components and elements, as they may be used under ultrasound guidance to fully fill in a cavity within breast 16, for example following an excisional procedure such as may be carried out with excision& device 10 with its cutting attachment 13. The corresponding stages as were illustrated in FIG. 30, are again presented here with the same labels and figure numbers/letters.

Figure 31F:
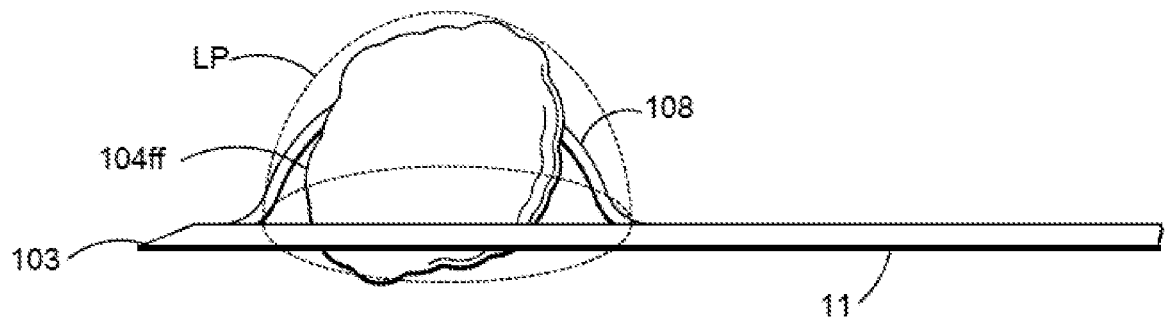

FIG. 31 shows the way 102i may appear on ultrasound display 18, as imaged with transducer 17. FIG. 31 also shows excisional device 10 with attached injection syringes attached via tubes 105 and 106, showing the manner in which a two-component substance may be introduced, such as a substance and its catalyst for example. FIG. 31a shows tubes 105 and 106 being used without excisional device 10, freehand, according to embodiments. FIG. 31f further illustrates the movements of loop/sealer 108 in its revolution about stable substance 104 designated as "fully formed" by lower case letters "ff". The dashed curved lines labeled "LP" indicate the pathway that loop/sealer 108 takes in its progression from sealing, through progressive exposure of substance 104ff, followed by full retraction of loop/sealer 108 and then, if desired, fully furled position in anticipation of its removal. It is pointed out that, should membrane 102 be constructed of bio-absorbable and/or biodegradable substance, it can be severed from a shaft of excisional device 10 either by loop/sealer 108 or other of any number of simple mechanisms (not shown). Also shown in FIG. 31 is/are element(s) 107, which represent implantable information, such as echogenic and/or radiopaque elements, which may be imaged on follow-up examination, and may transmit or otherwise provide information such as date of implant and/or any other information desirable. The element(s) may be pre-loaded within or on membrane 102, if membrane 102 is left behind, or reversibly attached to the inner surface of membrane 102 if membrane 102 is removed. If membrane 102 is a double wall element with the inner wall implanted, then the marker may be pre-attached to this surface. If membrane 102 in any configuration is removed entirely, then the marker elements may be positioned in other ways such as floating upwards to lay against a surface of substance 104 for easy orientation, or, this element may be left to randomly position itself, if acceptable. The letters/numbers in illustration 31 as shown on ultrasound display 18 are arbitrary and present only for clarity.

One embodiment is a method of utilizing introducer assembly 11 for delivery of components (implants, fillers, brachytherapy seeds, materials, markers or others for various therapeutic modalities and/or for marking purposes) to an excisional cavity site, following excision and lesion or sample collection steps. One embodiment may be carried out after successful excision and extraction of target tissue forming a cavity, treating cavity and/or adjacent walls and deeper tissues. The excisional device 10 of FIG. 4 may be introduced into the tissue under (e.g., ultrasound) guidance. An element such as introducer 100 may then be introduced into excisional device 10, engaging it into a drive mechanism of excisional device 10 and into the cavity via an introducer assembly. The membrane may then be filled to a desired volume, based on cavity volumetric analysis, while monitoring progress via a guidance modality to ensure complete filling of the cavity as desired (for best cosmetic results, for example). If the implant requires a curing period, once fully formed as in FIGS. 30b, 30c and 30d, the drive mechanism of excisional device 10 may be activated and continue until the membrane is fully retracted and furled. Once the membrane is fully furled, the excisional device 10 may be withdrawn from the introducer assembly 11 and from the excisional device 10 altogether. The skin incision may then be closed in the sterile manner of choice.

Figure 32:
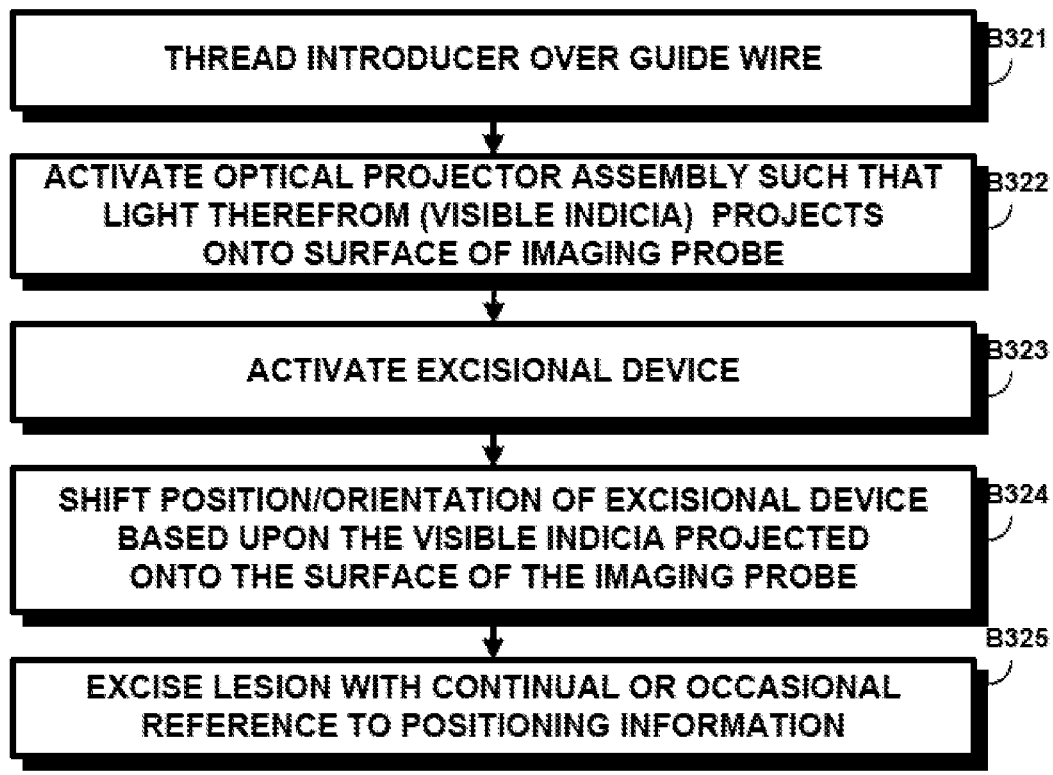
FIG. 32 is a flow chart detailing various methods and steps used for introducing excisional device components over guiding elements such as are shown in FIGS. 9 and 9a, according to one embodiment. This flow chart also explains a method for using these guiding elements to introduce other materials and/or other components using excisional device 10 and its introducer assembly 11 FIG. 2, and/or following use of excisional device 10 of FIG. 2.

FIG. 32 is a flow chart of a method according to one embodiment. Indeed, FIG. 32 details steps for introducing and operating an excisional device according to one embodiment. The method shown in FIG. 32 makes use, according to one embodiment, of the introducer assembly 11, excisional device 10 with ultrasound guidance and guide assembly 21 (e.g., a guide wire), guide tube 24 and optional insert cannula 28. Other elements may be substituted for the aforementioned components, as those of skill in this art may appreciate. As shown at B321, the introducer assembly 11 may be threaded or otherwise slid over guide assembly 21, which guidewire was previously inserted along a desired path to or near the lesion 15 to be excised. Indeed, the guide assembly 21 may be placed in a desired location using a guidance method of choice, whereupon the introducer assembly 11 may be threaded with a tapered guide wire. The device 28 may be inserted over the guide assembly 21 via eyelet components 22 or through "O" lot of introducer assembly 11 introducer assembly 11, for example. Once threaded, hub nut assembly 23 may be attached by placing slotted inner flare element 26 over guide assembly 21 and seating it against the flared end. The hub nut 27 may then be screwed onto flare element 26. Guide wire/tube 21/24 is now ready for delivery of desired elements such as local anesthetics and others to the target site area.

As shown in B322, the optical projector assembly (e.g., 90 in FIGS. 27-31) may now be activated, such that light (visible indicia) therefrom projects on a surface of the imaging probe, such as shown at reference 17 in FIGS. 17-31. The visible indicia may also be projected onto the sensor strip 91. Indeed, according to one embodiment, the projector 90 laser guide beams may then be activated and aimed at sensor strip 91, so that all laser dots appear on sensor strip. If no laser guidance is needed, guide assembly 21 may be withdrawn, and, if used, insert 28, before or after using cutting assembly 13. As shown at B323, the excisional device may then be activated. That is, the cutting assembly 13 may then be introduced and the intended excision may then be carried out by activation of excisional device 10. Prior to withdrawal of guide wire/tube, local anesthesia and/or other elements such as dyes, vasoconstrictors and the like may be delivered via guide tube element 24/hub assembly 23. As shown at B324, the position and/or orientation of the excisional device may be selectively moved/shifted based upon the visible indicia projected onto the surface of the imaging probe. The output of the optical projector assembly, therefore, may function as visible feedback to the operator, who may then confidently shift and re-orient the excisional device as needed, guided by the output of the optical positioning assembly. For example, the ultrasound display 18 may be consulted to view the generated angle line "PT" (on display 18) and to aim generated line "PT" that indicates desired path by aiming introducer assembly 11 introducer assembly 11/excisional device 10 up or downwards. The appearance of arc "SA" may be watched and, once on screen, its presence may be maintained by following on-screen instructions to swing introducer component left or right as directed. If no instructions appear and arc "SA" remains full and on screen, then the introducer assembly 11 and excisional device 10 are correctly aligned in-plane with ultrasound transducer. The aligned introducer assembly 11 may be further advanced until indicator arrow "SEI" appears on screen. When "SEI" appears, the introducer trough is correctly positioned directly under the center of ultrasound transducer 17.

As called for at B325, the lesion or tissue of interest may then be excised with continual or occasional reference to positioning information from the optical positioning assembly. Indeed, the cutting element (or other attachment such as collection assembly 61) may then be introduced and then excisional device 10 may be activated for operation appropriate for the attachment(s) present thereon and its progress may then be followed by observing movement of "SEI" along preset arc on screen. If not previously removed, guide assembly 21/24 or/and insert cannula 28 may remain in place, over which other components may be introduced to the target site.

One embodiment comprises using an embodiment of the present excisional device with stereotactic guidance such as would be used on a stereotactic x-ray stage. Indeed, use of an embodiment of the present excisional device may comprise using accepted stereotactic methods to image and to calculate x, y and z coordinates for the target lesion in multiple views. The excisional device 10 may be attached to the stereo stage holder and excisional device may then be introduced into tissue such as breast via a skin nick, after local anesthesia. The introducer assembly 11 may then be manually advanced to the correct position. If difficulties (due to, for example, dense or fibrous tissues) are encountered, a firing mechanism may be used to assist placement under lesion 15. If, however, firing is not desirable or is unsuccessful, the cutting assembly 13 may be introduced and rotation only may be carried out (i.e., without bowing, revolution, etc.) and gentle forward pressure may be applied and maintained to allow excisional device 10 to core and burrow to the correct, desired position. Upon reaching correct coordinates, rotation may be deactivated and the excision mode may be activated. Once excision is accomplished, the above-described procedure for collection of the specimen may be followed. Once extraction of the severed lesion is complete, the extracted specimen may be imaged, still enclosed in membrane 60 and a radiograph may be recorded to ensure complete removal of target(s) lesions. Thereafter, the skin incision may be closed in the sterile manner of choice.

According to another embodiment, embodiments of the excisional device 10 may be used together with metabolic imaging, magnetic resonance imaging (MRI) or molecular imaging (MI) such as positron emission mammography (PEM). Using an embodiment of the excisional device 10 with metabolic imaging or MRI may comprise using accepted metabolic imaging methods or MRI methods to calculate safe margins, and establishing correct paddle holes (PEM) as well as x, y and z coordinates (MRI). The guide may then be installed and a cannula device may then be inserted in the correct position and locked into the correct z-depth. The G-68 line source (PEM) or MRI beacon (MRI) may then be loaded and the correct trajectory for the excisional device 10 may then be verified. The excisional device 10 may then be advanced over an inserted cannula device into the tissue to the correct, desired position. If difficulties arise (due to, for example, dense or fibrous tissues), a firing mechanism may be used to assist placement under lesion 15. Once introducer assembly 11 and excisional device 10 are positioned correctly, the line source (MI/PEM guided excision) and/or beacon (MRI guided) may be removed, and replaced with cutter assembly 13 and the excision completed. Once excision is accomplished, the procedure for collection of a specimen shown in the figures and described above may be followed. Once extraction of the severed lesion or tissue specimen is complete, a post-biopsy scan may be carried out to verify complete removal of target lesion. Optionally, samples may then be imaged for evidence of abnormality within the removed samples and samples may be sent to a pathology lab for further analysis. Thereafter, the skin incision may be closed in the sterile manner of choice.

Introducer assembly 11, excisional device 10 and an internal ultrasound transducer may be used, according to one embodiment, to interrogate lesions for tissue characterization and precise edge location. Indeed, according to one embodiment, an ultrasound transducer may be introduced into a universal introducer and images acquired for use in edge detection and guidance, for excision and tissue characterization purposes, among other uses for high resolution scanning within tissues. Such may be carried out in close proximity to lesions such as cancers as well as benign and mixed abnormalities, according to one embodiment. introducer assembly 11 According to one embodiment, after making small skin nick, and administering local anesthesia in the area of anticipated cutting, the introducer assembly 11 may be advanced into the tissue such as breast 16, to a desired position, for example, directly under lesion 15, maintaining a safe distance from its inferior edge, using the guidance method of choice, such as ultrasound guidance, for example. Once stabilized in position, the internal ultrasound transducer may be placed into excisional device 10 and the rotation/advance function of the excisional device 10 may be activated, to automatically advance the internal ultrasound transducer element all the way to the distal end of introducer assembly 11, to a position directly beneath lesion 15, for example. A total sweep arc radian may then be chosen by placing channel follower 84 into desired channel such as 77 or 77a, and choosing a starting point of the sweep by rotating drum 70 using drum rotation handle 83 to the desired starting point for internal ultrasound interrogation/mapping. The ultrasound transducer may be activated during rotation, while maintaining stable angle and axial position of introducer assembly 11, for example, directly under lesion 15 of breast tissue 16, by observing its position under guidance method of choice, such as external ultrasound and/or other guidance modality such as stereotactic x-ray, MRI or other. After finishing interrogation and recording, the excisional device 10 may be removed as a complete assembly with the ultrasound transducer. Alternatively, once fully retracted, the ultrasound transducer may easily be removed from excisional device 10 by pressing button 82 and simply withdrawing the transducer. The removed ultrasound transducer may then be replaced with cutting, collecting or other elements for eventual next procedure stages.

The various components that will briefly be placed into living tissues may comprise biocompatible materials such as stainless steel or other biocompatible alloys, carbon fiber or other high strength fiber(s) and may be made of, coated with or comprise polymers and/or biopolymer materials as needed to optimize function(s). For example, the cutting elements may be made of or comprise hardened alloys and may be additionally coated with slippery materials to optimize passage through living tissues of a variety of consistencies and frictions. Some of the components may be purposely surface-treated differentially with respect to adjacent components so as to permit sliding, rotating or other with minimal friction interactions. Also, where referring to energizing of certain components, it is understood that insulating coatings may also be applied to various surfaces as required to maintain electrical integrity and insulation in order to prevent short circuits. The various gears shown and described herein may be made of or comprise any suitable, typically commercially available materials such as brass, steel, aluminum, nylons and or any variety of easily available (commercial) polymers such as moldable plastics and others. If used, the motor powering the various powered functions may be a commercially available electric DC or alternatively, AC motor, (electrically isolated from the patient if AC). The handle of the device may likewise be made of or comprise moldable plastic or other suitable rigid, easily hand held material, which may also be coated with non-slip surface treatments and/or materials or combinations of these and the handle may also be configured in such a way as to make it easily adaptable to one of any number of existing guiding platforms such as stereotactic table stages. The materials used in the device may also be carefully selected from a ferro-magnetic standpoint such that the resulting instrument may be compatible with magnetic resonance imaging (MRI) equipment, which are increasingly commonly used for biopsy procedures.

The vacuum/delivery assembly components may comprise commercially available syringes and tubing, for connecting to the instrument, along with easily available reed valves for switching between suction and emptying of such materials as fluids, which may be suctioned by the vacuum components. The fluids collected by the instrument in this manner may then be ejected into an additional external, yet portable liquid storage vessel connected to the tubing of the instrument for discarding or for safe keeping for laboratory cellular analysis. Fluids delivered may be of a variety of compositions, and for a variety of purposes, including but not limited to, enhancing cutting by transmission of electrolyte charges, cooling purposes, both to minimize harm to body tissues and/or device components, and may be as simple as commercially available saline solutions or other medical grade liquids, and also may include certain gaseous elements such as argon, $CO_2$ and/or others such as are commonly used in radiofrequency type surgical procedures to enhance cutting efficiencies for example.

The power source (for motor driven functions) may be an external commercially available transformer to DC current, approved for medical device use, and plugged into the provided socket in the device, or may be an enclosed battery of any suitable voltage/current, that is readily available commercially. The battery may be of one time use and recyclable or may be of the rechargeable variety. The power source for energized cutting, including electrosurgery, may likewise be selected from any number of external energy generators such as commonly available commercial radiofrequency electrosurgical units, and configurations are provided for both bipolar and mono-polar connections as desired.

According to one embodiment, beam generating, aiming/positioning, attachment/projector 90 may be used to project the real angle of excisional device 10's introducer assembly 11, and any attachments introduced thereby, and will progress along as operator of excisional device 10 advances its introducer in position to properly perform functions for which this instrument and its components, elements, attachments and accessories are designed, according to embodiments. In the same way, additional beams generated as lateral lines may be included to provide additional information as described, and to ensure extreme accuracy. Additionally, sensing strip LS1/LS2 components of sensing strip 91 may comprise light detecting strips and may be modified to custom fit various ultrasound transducers for proper alignment/depth. This strip LS1/LS2 may also be configured to provide the information needed to generate on-screen lines/depth indicators Y1 and Y2, as shown in FIG. 27.

According to embodiments, the mechanical functions powering excisional device 10, FIG. 1 may include electrical, manual or other mechanical structures such as spring actuated. It is to be understood that power for aspects of an embodiment of the excisional device 10 may be obtained from, for example, energy stored by any number of springs, by compressed gas power sources and/or other energy storage configurations, all of which are to be considered within the scope of the present disclosure. The release of spring and/or compression energy may, for example, power various and/or all activities of excisional elements introduced through excisional device 10, FIG. 1. This particular mechanism (wind up spring, and/or compressed air power) may be of particular use in remote areas where battery power is not reliably available. Moreover, in applications such as in an MRI suite, given the powerful magnetic forces in that environment, it may be desirable to limit. Ferro-magnetic components of device 10, and its accessories and introduced elements as embodied herein.

Advantageously, the introducer assembly may be configured to enable an operator to perform essential phases of a procedure without having to re-establish proper positioning once that positioning, including depth from the surface of the organ such as a breast skin surface, alignment and axial penetration depth, is achieved. Also, separately introducing an extremely low profile, streamlined introducer component is also advantageous, relative to achieving a highly accurate positioning of the device. Indeed, the favorable impact of such a profile is greatest in the areas of minimizing the physical and imaging effort required to position the introducer in place, limiting to the greatest possible degree the associated trauma, and maximizing the on-screen clarity of the introducer component from which subsequent phases can be precisely and consistently carried out from this stable base of support. The more gently a biopsy instrument can approach, cut, collect and transport a target lesion, the more meaningful and useful the information gathered by the obtained tissue specimens will be.

Although not immediately apparent, the less the operator's powerful muscles such as triceps and others need be engaged during the approach, cut, collect and target lesion removal phases, the clearer the guiding image will be, especially when using guidance modalities such as handheld ultrasound probe equipment. Furthermore, when a conventional device must utilize a firing mechanism in order to position itself, (which is a defining characteristic of most all existing side cutting instruments for example), the sheer violence of such a mechanism carries several clinical disadvantages, ranging from annoying to potentially dangerous. Unwanted penetration of distal tissues is a real and potentially serious side effect. Injection of potentially dangerous abnormal tissues such as cancerous cells or "seeds" as described in the literature, and/or infectious organisms can occur and has been documented. Embodiments of the excisional device 10, however, enable the use of unique, gentle and far more manageable method for performing the necessary stages of penetration, positioning, cutting, collecting, transport and others, thereby enabling a less violent and potentially less harmful procedure to be carried out.

Embodiments also create an opportunity to perform a biopsy/excisional procedure, along with other pre-excisional and post-excisional phases, that is less traumatic and far more precise, and these elements are also aided by limiting cross-sectional bulk of the elements of the device that must traverse tissues such as 16 and 15, as shown in FIG. 28.

Additionally, where it may not be possible, or at least impractical to completely eliminate cross sectional bulk, embodiments comprise design features and enable methods to minimize the effects of cross sectional hulk. Embodiments comprise narrow, low profile, tapered, streamlining and other elements like slippery surface treatments where necessary, as well as potentially sharpened elements such as tips of introducer assembly 11, cuffing assembly 13 and others such as collection assembly 60, to make room for gentle passage of these components along, the shaft of introducer assembly 11. Embodiments may also negate or minimize the effects of cross-sectional bulk and may also include the ability to gently separate tissues on approach (empty introducer), and controllably coring a path towards and/or underneath target lesion 15, by gentle rotation of cutting assembly 13. Having, multiple functions such as those embodied herein save valuable cross-sectional area in other ways, which, by design, create a device that is as minimal as possible in outer diameter while providing the maximum visibility, stability and capability of excisional device 10 and its introducer assembly 11. This is important front a clinical standpoint, since it has been demonstrated in multiple peer-reviewed journals that the two most important considerations for purposes of prognostication, subsequent treatment planning and overall success of an excision of malignant tissues and to a possibly lesser extent, benign abnormal tissues, include physically measured size of the lesion itself and the ability to ensure that all abnormal tissue is removed with clear margins.

The provisions for precise placement of all elements involved in the various phases of diagnosis, pre- and post-excision treatments, as well as the excision itself, according to embodiments, are significant. The ability to achieve precise, total removal of abnormal tissues must be made available to operators of a wide variety of experience and skill levels in order to maximize the impact of new technology. Accordingly, experience with excisional biopsies has shown that one of the most difficult steps to achieve is identification of the deep, posterior margins of a lesion, as well as the ability to position a cutting instrument a consistent distance away from this critical border. According to embodiments, that step may be performed with the introducer assembly 11 in its maximum visibility, minimal cross-section configuration. Other significant features of embodiments include the capability of interrupting specific stages in the procedure. According to embodiments, the helical cutting system may be used in a variety of ways to maximize cutting efficiency and deliver a variety of elements such as local anesthetics, pro-coagulants, hemostatic agents, and others. Thermal damage in collateral tissues may be minimized as well as in the retrieved abnormal tissues. As a result, the amount of thermal killing effect may be controlled in a far more precise and consistent manner.

The helical cutting elements may also apply gentle, predictable traction on excisional device 10, augmenting placement and stabilization during, introduction and/or excision. Additionally, the helical action can augment the vacuum and removal of liquids, gasses and heat, during cutting, that is optimized by its design, and which also enables constant cleaning/wiping action of coagulum and other tissue elements which may progressively lead to decreased cutting efficiency. As a result, the collected specimen is least likely to be disrupted architecturally, thermally and/or in orientation. Advantageously, embodiments enable the clinician/operator to preselect a pathway, and to precisely place introducer base element 11 in correct position for subsequent operations, easing correlation of image abnormality and histopathological analysis.

Other structures, organizations and modes of operation are possible. One example is the pairing of an aiming positioning projector 90 with a sensor strip component 91, both shown in FIG. 29. For instance, the projector may be used by itself and other methods not requiring a separate sensor strip may be used, instead utilizing reflected signals for all functions described herein. Embodiments combine mechanical and RE cutting mechanisms that are separately effective, and are both strong yet flexible, and thus, may be utilized alone or in the combination disclosed herein. However advantages contemplated and anticipated by the combination include the advantages of each method such as non-thermal cutting of the mechanical method, versus the favorable pro-coagulant effect of thermal cutting, so long as that effect is controlled to prevent unwanted damage to tissues in close proximity to the cut. Thermal cutting also has the ability to deactivate transitional cells, which, if allowed to remain viable, may become abnormal and possibly even dangerous. This effect, again, if controlled consistently, is desirable to a limited extent. The combination of these elements can maximize efficiency of both, can limit the amount of energy needed, maintain clear surfaces of these elements, and may perform several simultaneous functions such as augmenting position stability, minimizing bulk of the elements (since potentially cooler temperatures can permit smaller mass, while some thermal effect may permit thinner mechanical components by creating less cutting resistance), and other advantages not detailed here.

Embodiments comprise a device or piece of equipment designed to do several things not limited in usefulness to medical biopsy/excisional device purposes. Indeed, embodiments make use of and combine principles of precise guidance, simulation, projection, and real time feedback of progress along projected pathways, thereby rendering embodiments potentially suitable to many commercial/industrial applications where precise planning, projection placement and separation of operations is/are desirable, potentially on a much larger scale than needed in medical biopsy procedures. Since embodiments of the present device can function under a variety of image guidance modalities and/or where staged introduction of a conduit/introducer is desirable for example, the excisional device 10 may be made far more compactly than other equipment made for the same purpose. The excisional device 10 may also potentially far more reliably function to excise, collect and transport under extreme conditions that may be difficult to control such as shifting surroundings and other factors. Likewise, it may be apparent from the descriptions herein that attachments and various other components may be designed, added and/or modified for use with the excisional device 10, without loss of any of its functional ability, which may have uses both within the medical field as well as outside it. Additionally, the dimensions of many of the components of the device can be made to order for the given application, and in a variety of shapes such that it may obviously be useful in many remote applications, some of which may require embodiments to traverse multiple materials which may themselves be fixed in nature or moving, again, without adversely affecting the performance of the instrument. Elements of the device can be separately useful, and the description herein is not meant to convey in any way that the separate elements are not useful new concepts in their own right, and separate from any of the other elements shown and/or described herein. For example, elements configured for rotating, cutting, targeting, collecting, delivering and other elements may perform their intended function(s) without the need for other components shown and described herein and should not be assumed to be dependent on some of the other features in order to function as intended.

Significantly, one embodiment of a biopsy, excisional device may comprise features for performing medical excisional biopsy procedures, in multiple stages, by providing a platform instrument and an introducer conduit for a variety of pre and post-excisional procedures. These features may include features for placement simulation, real time monitoring of penetration and positioning along a pre-simulated pathway, excision, part off, collection, transport and preservation of specimens for medical purposes such as diagnosis and treatment of a variety of diseases and abnormalities. The device may also comprise integral, detachable and/or independently useable components designed to perform functions such as enhancing placement, guiding elements, delivery elements for liquids and collecting elements for collection of intact masses of abnormal and normal tissues for histo-pathological analysis as well as for collection of liquids and/or cells and cellular components for cellular analysis, as well as components for delivery and/or aspiration of gases, liquids and/or solids at various selectable stages of the procedure. Some of these components may be used to enhance other functions, such as for enhancing cutting efficiency, minimizing thermal and/or mechanical damage of other favorable functions. According to one embodiment, one of these functions may include implanting materials to enhance healing, provide additional therapeutic agents locally, such as brachytherapy administration, medications delivery for local control, and including cosmetic implants that may enhance the overall aesthetic outcome as well as to promote more rapid and complete healing. The device may be selectable for automatic and/or manual function and may perform its intended uses with or without image guidance. In automatic mode, the instrument may perform its tasks with the great consistency and precision, since many of the automated phases take advantage of the accuracy and stability of the initial positioning of the introducer element(s) of the instrument, as well as the real time monitoring capability of various other components. In automated mode, the device may be used with ease by both right and left handed operators. The device and its components and/or optional accessories may also be compatible with a variety of guidance imaging equipment such as ultrasound, magnetic resonance imaging and X-ray imaging. The device may be disposable and/or recyclable, highly portable, and delivered for use in sterile packaging. The device may be configured to be minimally invasive, and may take maximally preserved tissue specimens in operator-selectable sizes, so as to preserve gross anatomic, cellular and subcellular architectures as well as to maintain integrity of the overall structures and makeup of the samples themselves, as well as their relationships with included normal adjacent segments of tissue, for example in surrounding margins of increasingly normal adjacent, included samples so that transition area can also be used for analysis. The present device and components thereof may be configured to deliver the samples reliably and in correct anatomic orientation, for accurate recording, measurement and analysis there from, so that the information can be as complete and as accurate and as possible. Preserving orientation is highly important in the event that unseen extensions of abnormal tissue are inadvertently left behind. In such a case, knowledge of where to excise, collect and analyze for completeness, additional sections or "peels" of tissue is preserved for the operator, such that accurate completion of the excision is easily possible. Embodiments may comprise several key features that enhance its therapeutic capabilities, or at least the most important therapeutic steps on the pathway to achieving a disease-free state, and these capabilities can be utilized at various stages along the diagnosis/treatment pathway.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions substitutions and changes in the form of the methods and systems described herein may be made without departing from the spirit of the disclosure. The accompanying claims and their equivalents are intended to cover such forms or modifications as may fall within the scope and spirit of the disclosure. For example, those skilled in the art will appreciate that in various embodiments, the actual physical and logical structures may differ from those shown in the figures. Depending on the embodiment, certain steps described in the example above may be removed, and or while others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. An excisional device, comprising:
an introducer comprising a distal trough portion; and
a cutting assembly disposed within the introducer and comprising:
an axial band element comprising an outer circumference and configured to selectively change shape and extend out of and away from the distal trough portion and retract back into the distal trough portion; and
a helical cutting element wound fully around the outer circumference of the axial band element and configured for rotation about the outer circumference of the axial band element, the helical cutting element comprising coils that are spaced apart to define interstitial empty spaces between adjacent coils such that the interstitial empty spaces expose the axial band element between adjacent coils.

2. The excisional device of claim 1, wherein the axial band element comprises at least one opening configured to enable and evacuation and delivery of at least one of smoke and a fluid at least through the interstitial empty spaces between adjacent coils.

3. The excisional device of claim 1, wherein the axial band comprises at least one edge.

4. The excisional device of claim 1, wherein the helical cutting element is configured to be energized with radio frequency (RF) energy.

5. The excisional device of claim 1, wherein the axial band element comprises a first axial band and a second axial band disposed adjacent and coupled to the first axial band.

6. The excisional device of claim 5, further comprising an insulating layer disposed between the first axial band and the second axial band.

7. The excisional device of claim 1, wherein the helical cutting element is configured to rotate while the axial band element extends out of and back into the distal trough portion.

8. The excisional device of claim 1, wherein the interstitial empty spaces between adjacent coils reveals portions of the axial band around which the helical coil element is wound.

9. The excisional device of claim 1, wherein the device is configured for bipolar RF operation.

10. The excisional device of claim 9, wherein the axial band has a same electrical polarity as does the helical cutting element.

11. The excisional device of claim 9, wherein the axial band has a different electrical polarity as does the helical cutting element.

12. A bipolar radio frequency (RF) excisional device, comprising:
an introducer comprising a distal trough portion; and
a cutting assembly disposed within the introducer and comprising:
an axial band element comprising an outer circumference and configured to selectively change shape and extend out of and away from the distal trough portion and retract back into the distal trough portion; and
a helical cutting element wound fully around the outer circumference of the axial band element and configured for rotation about the outer circumference of axial band element,
wherein at least one of the introducer, the axial band element and the helical cutting element is charged with RF energy of a first electrical polarity and at least one other of the introducer, the axial band element and the helical cutting element is charged with RF energy of a second electrical polarity that is opposite the first electrical polarity.

13. The excisional device of claim 12, wherein the axial band element is charged to the first polarity and the helical cutting element is charged to the second polarity.

14. The excisional device of claim 12, wherein the introducer is charged to the first electrical polarity and wherein both the axial band element and the helical cutting element are charged to the second polarity.

15. The excisional device of claim 12, wherein the axial band comprises at least one edge.

16. The excisional device of claim 12, wherein the axial band element comprises a first axial band and a second axial band disposed adjacent and coupled to the first axial band.

17. The excisional device of claim 16, further comprising an insulating layer disposed between the first axial band and the second axial band.

18. The excisional device of claim 12, wherein the helical cutting element is configured to rotate while the axial band element extends out of or retracts back into the distal trough portion.

19. The excisional device of claim 12, wherein the helical cutting element comprises coils that are spaced apart to define interstitial empty spaces between adjacent coils.

20. The excisional device of claim 19, wherein the interstitial empty spaces between adjacent coils reveals portions of the axial band around which the helical coil element is wound.

21. An excisional device, comprising:
an introducer comprising a distal trough portion; and
a cutting assembly disposed within the introducer and comprising:
an axial band assembly comprising an outer circumference and configured to selectively change shape and extend out of and away from the distal trough portion and retract back into the distal trough portion, the axial band assembly comprising a first axial band element and a second, generally co-extensive second axial band element coupled to the first axial band element; and
a helical cutting element wound fully around the outer circumference of the axial band assembly and configured for rotation about the outer circumference of the axial band assembly.

22. The excisional device of claim 21, wherein at least one of the first and second axial band elements defines an edge.

23. The excisional device of claim 21, further comprising an insulating coating disposed on at least a portion of the first and second axial band elements.

24. The excisional device of claim 21, wherein at least one of the first and second axial band elements comprises at least one opening configured to enable and evacuation and delivery of at least one of smoke and a fluid.

25. The excisional device of claim 21, further comprising an insulating layer disposed between the first axial band element and the second axial band element.

26. The excisional device of claim 21, wherein the helical cutting element is configured to be energized with radio frequency (RF) energy.

27. The excisional device of claim 26, wherein the device is configured for bipolar RF operation.

28. The excisional device of claim 27, wherein at least one of the first and second axial bands has a same electrical polarity as does the helical cutting element.

29. The excisional device of claim 27, wherein the first and second axial bands have a different electrical polarity as does the helical cutting element.

30. The excisional device of claim 21, wherein the helical cutting element is configured to rotate while the axial band element extends out of or retracts back into the distal trough portion.

31. The excisional device of claim 21, wherein the helical cutting element comprises coils that are spaced apart to define interstitial empty spaces between adjacent coils that expose portions of the first and second axial bands around which the helical coil element is wound.

32. An excisional device, comprising:
an introducer comprising a distal end, the introducer defining a longitudinal axis; and
a cutting assembly comprising:
an axial band element comprising an outer circumference and configured to selectively change shape and extend away from the longitudinal axis and to retract back towards the longitudinal axis; and
a helical cutting element wound fully around the outer circumference of the axial band element and configured for rotation about the outer circumference of the axial band element.

* * * * *